United States Patent
Dong et al.

(10) Patent No.: US 11,378,541 B1
(45) Date of Patent: Jul. 5, 2022

(54) SELF-CONTAINED, AUTOMATED, LONG-TERM SENSOR SYSTEM FOR MONITORING OF SOIL AND WATER NUTRIENTS IN FIELDS

(71) Applicant: Iowa State University Research Foundation, Inc., Ames, IA (US)

(72) Inventors: Liang Dong, Ames, IA (US); Yueyi Jiao, Ames, IA (US); Yuncong Chen, Ames, IA (US); Azahar Ali, Ames, IA (US); Xinran Wang, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 294 days.

(21) Appl. No.: 16/663,116

(22) Filed: Oct. 24, 2019

Related U.S. Application Data

(60) Provisional application No. 62/750,663, filed on Oct. 25, 2018.

(51) Int. Cl.
*G01N 27/333* (2006.01)
*B08B 9/032* (2006.01)
(Continued)

(52) U.S. Cl.
CPC ....... *G01N 27/3335* (2013.01); *B08B 9/0321* (2013.01); *G01N 1/02* (2013.01);
(Continued)

(58) Field of Classification Search
CPC ............ G01N 27/333; G01N 27/3335; G01N 27/301; G01N 27/414; G01N 2033/245; G01N 1/02; E02D 1/04; E02D 1/06
See application file for complete search history.

(56) References Cited

U.S. PATENT DOCUMENTS 4,409,088 A * 10/1983 Kanno ............... G01N 27/3335
134/25.4
5,033,397 A   7/1991 Colburn, Jr.
(Continued)

OTHER PUBLICATIONS

Khripoun et al., "Nitrate-Selective Solid Contact Electrodes with Poly(3-octy;thiophene) and Poly(aniline) as Ion-to-Electron Transducers Buffered with Electron-Ion-Exchanging Resin," Electroanalysis 18, 2006, No. 13-14, 1322-1328 (Year: 2006).*
(Continued)

*Primary Examiner* — Alexander S Noguerola
(74) *Attorney, Agent, or Firm* — McKee, Voorhees & Sease, PLC

(57) ABSTRACT

An automated, fieldable ion-selective sensor system for frequent detection of nutrients in soils or water is set forth. In one aspect, an integrated small form-factor housing includes a battery, processor, a fluid manipulation unit and reservoirs, and a chemical species detection cell. A flow-through sampling head can be connected to the detection cell and a waste reservoir by flexible tubing sealingly connected at opposite ends of the tube. In one aspect, improved performance of the ion-selective sensor includes adding an ion-to-electron transfer interlayer between an ion-selective membrane and its working electrode. In one aspect, the sensor is solid-state and uses printed polymeric composite of POT-$MoS_2$. The use of a porous tube for a sampling head and fluid connection at opposite ends allows not only fluid to be removed from the head to the detection cell for measurement but also flow in an opposite direction and out to a waste reservoir to clean and reset for a next sample measurement.

22 Claims, 41 Drawing Sheets
(38 of 41 Drawing Sheet(s) Filed in Color)

(51) Int. Cl.
G01N 27/327 (2006.01)
G01N 33/24 (2006.01)
G01N 27/40 (2006.01)
G01N 1/02 (2006.01)
E02D 1/06 (2006.01)
E02D 1/04 (2006.01)

(52) U.S. Cl.
CPC .......... *G01N 27/327* (2013.01); *G01N 27/40* (2013.01); *G01N 33/246* (2013.01); *E02D 1/04* (2013.01); *E02D 1/06* (2013.01); *G01N 2033/245* (2013.01)

(56) References Cited

U.S. PATENT DOCUMENTS

| | | | |
|---|---|---|---|
| 5,526,705 | A | 6/1996 | Skotnikov et al. |
| 5,728,281 | A * | 3/1998 | Holmstrom .............. A61N 1/05 600/347 |
| 5,985,117 | A | 11/1999 | Bachas et al. |
| 6,398,931 | B1 | 6/2002 | Burchette et al. |
| 8,444,937 | B2 | 5/2013 | Tuli et al. |
| 8,767,194 | B2 | 7/2014 | Preiner et al. |
| 2006/0016701 | A1 * | 1/2006 | Qin ................... G01N 27/3335 205/792 |
| 2007/0013908 | A1 | 1/2007 | Lee et al. |
| 2014/0165713 | A1 | 6/2014 | Frey |
| 2014/0345394 | A1 | 11/2014 | Schildroth |
| 2018/0003667 | A1 * | 1/2018 | Dam ..................... B29C 39/003 |

OTHER PUBLICATIONS

Lin et al.."Preparation and characterization of polythiophene/molybdenum disulfide intercalation material," Materials Research Bulletin 44 (2009) 719-723 (Year: 2009).*

Guinovart et al., "A reference electrode based on polyvinyl butyral (PVB) polymer for decentralized chemical measurements," Analytics Chimica Acts 821 (2014) 72-80 (Year: 2014).*

Nolan et al., "Fabrication and Characterization of s Solid State Reference Electrode for Electroanalysis of Natural Waters with Ultrsmicroelectrodes," Anal. Chem. 1997, 69, 1244-1247 (Year: 1997).*

Lobsey et al., "An automated system for rapid in-field soil nutrient testing," 2010 19th World Congress of Soil Science, Soil Solutions fora Changing World Aug. 1-6, 2010, Brisbane Australia (Year: 2010).*

Lund et al., 2004. Managing pH variability with on-the-go pH mapping. In: Proceedings of the Seventh International Conference on Precision Agriculture. Ed. D.J. Mulla, The Precision Agriculture Center, University of Minneapolis, St Paul, MN, USA. (Year: 2004).*

Lehmann et al., "miniature multisensor probe for soil nutrient monitoring," Procedia Engineering 87 (2014) 1420-1432 (Year: 2014).*

Final Report Summary—NUTRI-STAT (Real-time, in-situ, N, P, K, pH and electrical conductivity soil-analysis system to facilitate accurate nutrient management), European Commission Project NUTR-STAT Grant agreement ID: 286489 (Year: 2014).*

Ali et al., "Continuous Monitoring of Soil Nitrate Using a Miniature Sensor with Poly(3-octyl-thiophene) and Molybdenum Disulfide Nanocomposite", Applied Materials & Interfaces, vol. 11, pp. 29195-29206 Jul. 18, 2019.

Ali et al., "Continuous Monitoring of Soil Nitrate Using a Miniature Sensor with Poly(3-octyl-thiophene) and Molybdenum Disulfide Nanocomposite", Applied Materials & Interfaces, Supplemental Information, 5 pages Jul. 18, 2019.

Ali et al., Novel All-Solid-State Soil Nutrient Sensor Using Nanocomposite of Poly(3-Octyl-Thiophene) and Molybdenum Sulfate, Transducers 2019—Eurosensors, pp. 170-174, Jun. 23, 2019.

* cited by examiner

SELF-CONTAINED, AUTOMATED, LONG-TERM SENSOR SYSTEM FOR MONITORING OF SOIL AND WATER NUTRIENTS IN FIELDS

CROSS-REFERENCE TO RELATED APPLICATIONS

This application claims the benefit of Provisional Application U.S. Ser. No. 62/750,663, filed on Oct. 25, 2018, all of which are herein incorporated by reference in their entirety.

GOVERNMENT RIGHTS CLAUSE

This invention was made with Government support under (1) Department of Energy Contract No. DE-AR0000824 and (2) USDA/NIFA Grant No. 2017-67013-26463. The government has certain rights in the invention.

I. BACKGROUND OF THE INVENTION

A. Field of the Invention

The invention is about an automated, fieldable ion-selective sensor system for frequent detection of nutrients (nitrate, phosphate, sulfate, potassium, etc.) in soil and water. One aspect of the invention includes an all-solid-state ion-selective sensing unit using a printed working electrode of, e.g., poly(3-octyl-thiophene)-molybdenum disulfide (or POT-$MoS_2$) nanocomposite as an ion-to-electron transducing layer and a printed or coated sandwiched solid-state reference electrode, e.g., ($S^3RE$) of Nafion-polyvinyl butyral/sodium chloride-silver/silver chloride (or Nafion-PVB/KCl-Ag/AgCl), for high sensitivity and selectivity measurements.

As will be further discussed herein, variations are possible. Non-limiting examples include that POT could be replaced by other polymers which are conducting, provide redox properties, and are lipophilic. $MoS_2$ is a very specific material used with POT as it provides high redox activity, high conductivity, and improved electron conducting property of POT.

B. Problem Statement

As is made clear in the publications cited in the Background References section below, the benefits of measuring soil nutrient levels can be very significant for agricultural crop producers. As such, a variety of attempts at obtaining meaningful soil nutrient measurements have been made over the years. More recently, recognition of benefits of not just soil nutrients for a whole field but rather both at different spatial locations around a field and different depths has become apparent. However, the challenges are substantial.

Currently, farmers take soil samples to a laboratory for assessing contents of important nutrients available in the soil. It is difficult for farmers to know the information on dynamic changes in nutrient availability over time. Existing technologies available today do not provide the capacity to automatically monitor soil nutrients in fields at multiple times.

Problem 1: Currently, existing nutrient sensors, when they operate in the field for frequent measurements of nutrient ions, are not able to automatically reset themselves to their original status after use. For example, after ion-selective membrane-based sensors detect particular ions for multiple times, the ion-selective membranes coated on the working electrodes cannot be automatically cleaned, reconditioned, and recalibrated in the field. The detection accuracy of the sensors for the following measurements are affected. Long-term sensor performance stability and accuracy should be improved. There is a critical need to realize in situ cleaning, reconditioning, and recalibration for ion-selective membrane based potentiometric sensors when they are deployed in the field.

Problem 2: Many types of soil sensors and sensing units of sensor systems have been developed to monitor nutrients in soil and water. Common measurement practices include ion chromatography, spectrophotometry, ion-selective membrane (ISM) based sensors, and electrochemical sensors. Among these, chromatography and spectrophotometry are limited to laboratory settings due to high cost, large size, complex sample preparation and high power consumption, while the goal is design of affordable sensors for site-specific and real-time measurements. Enzymatic electrochemical sensors, using an ion-specific enzyme for molecular recognition, have also been developed to realize detection of a specific ion. This type of sensor, however, has short lifetime, is limited by the availability of the ion-specific enzymes, and is only suitable for laboratory measurement. The ISM based sensors are simple and field deployable and can convert the activity of a specific ion in a solution into an electrical signal. They, however, require specific ion-selective mechanisms and careful design in material, structure and manufacturing to obtain both high performance and low cost. Unfortunately, almost no ISM based sensors are commercially available for long term, real time, continuous monitoring of nitrate in the field with good selectivity and high sensitivity. There is a significant need to address the issues of sensor lifetime, accuracy, and stability of the sensors or the sensing units of sensor systems for field measurements. This can be achieved by improving the quality of both working and reference electrodes of the ISM based sensors or the sensing units of sensor systems.

Problem 3: Conventional porous ceramic capillary based suction heads for soil water extraction have one end opened and the other end closed. For miniaturized capillary tubes, manual removal of the remaining chemicals from the interior of such ceramic tubes is challenging, due to limited space. The smaller the ceramic tubes, the more difficult the operations (rinsing, flushing, etc.) become. Integration of such ceramic tubes with soil water detection units will not lead to field-deployable sensors for long-term use.

It therefore is apparent there is room for improvement in this technological area.

Background References

The following provide background information and detail of the type indicated. Each is incorporated by reference herein in its entirety:

| # | Citation | Background Information About: |
|---|---|---|
| 1 | US 20070013908 A1: Portable Raman Sensor for Soil Nutrient Detection. | Raman based sensor for phosphorus detection Probe in situ Housing with integrated-computer, laser, batteries, fiber optic cable |

-continued

| # | Citation | Background Information About: |
|---|---|---|
| 2 | U.S. Pat. No. 5,033,397: Soil Chemical Sensor and Precision Agricultural Chemical Delivery System and Method. | Pull-through-ground real time soil sensing implement |
| 3 | U.S. Pat. No. 8,444,937 B2: In-Situ Soil Nitrate Ion Concentration Sensor | In situ soil nitrate ISE Porous sleeve in soil probe inserted |
| 4 | U.S. Pat. No. 5,985,117: Ion-Selective Membrane Sensors With Mercuracarborand Ionophore | Ion-selective electrodes membranes |
| 5 | US 20140345394 A1: Portable Soil Testing Apparatus and Method | Portable soil testing unit On-board mixing cup to mix soil and water and then insert detector into mixture in cup. Ion selective sensors [0026] Detect different nutrients [0027] |
| 6 | U.S. Pat. No. 6,398,931 B1: Combination Ion-Selective Electrode With A Replaceable Sensing Membrane. | Ion-Selective Electrodes Replacement sensing membranes |
| 7 | US 20140165713 A1: Systems, Devices, And Methods For Environmental Monitoring In Agriculture | Soil monitoring, including nitrates Ion selective electrodes. In ground water collection Micropumps ISE sensors Porous soil water collection tubes -water in during wetting events Battery Processor In situ |
| 8 | U.S. Pat. No. 5,526,705: Automated Work Station For Analyzing Soil Samples | Automated soil sample processing on bench top. |
| 9 | U.S. Pat. No. 8767194 B2: Automated Soil Measurement | Soil measurement Device Mixing chamber Optical detector |
| 10 | U.S. Ser. No. 62/411,315: Electrophoretic Soil Nutrient Sensor For Agriculture | Ion species detection in soil on the go Variety of species Microchip Electrophoresis Vacuum sucks soil solution into microfluidic circuit. Microfluidics controls |

II. SUMMARY OF THE INVENTION

A. Objects, Features, and Advantages of the Invention

A main object, feature, and advantage of the present invention is to improve over or solve problems and deficiencies in the state-of-the-art related to systems, methods, and apparatus for measuring or estimating soil nutrient levels in agricultural fields.

Further objects, features, and advantages of the invention include one or more of:
  a. Ability for in situ monitoring over extended periods of time.
  b. Robustness over a range of sometimes harsh and extreme environmental conditions.
  c. Minimal disruption to planting, harvesting, and intermediate agricultural production and field tasks.
  d. Self-contained and self-sufficient over a long useful measuring time span, as well as at least semi-automated or fully automated.
  e. Adaptable for different applications and chemical sensing tasks, including ion-selective detection.
  f. Integratable regarding a variety of different components (sensing elements, fluidic circuitry, etc.) and functionalities in a relatively small form factor.
  g. Ability to auto reset, auto recondition and auto calibration for multiple new detection cycles.
  h. Increased performance and accuracy of detection, including higher sensitivity, high selectivity working electrode configuration, and higher stability reference electrode configuration.
  i. Versatile sample collection head.
  j. Can provide sufficiently accurate and precise measurements with quite small sample volume sizes.
  k. Can be integrated with a variety of sensing techniques
  l. Can be used for monitoring of nutrient ions in both soil and water.

B. Aspects of the Invention

The disclosed sensor system can automatically reset, recondition, and recalibrate the sensing unit for long-term, high-precision detection of nutrient ions in the field. In contrast, almost no existing nutrient sensors are able to do so. The ability of the disclosed sensor system to reset, recondition, and recalibrate itself in the field is achieved using multiple simple fluid manipulation units (e.g., in one example each consists of two normally-closed mini peristaltic actuators and a mini vacuum pump) and a unique flow-through suction head with openings at two sides.

The disclosed sensor system uses a new ISM-based sensing unit with an improved sensitivity, selectivity, and reliability. In the ISM-based sensing element, the working electrode contains a novel ion-to-electron transducing layer sandwiched between an ISM and a metallic electrode. In one example, the ion-to-electron transfer layer is a nanocomposite of poly(3-octyl-thiophene) and molybdenum disulfide (POT-$MoS_2$). The use of POT-$MoS_2$ in the working electrode leads to increased redox activity and electron conduction, thus increasing sensitivity and selectivity. Also, because high lipophilicity of the POT-$MoS_2$ nanocomposite helps to minimize formation of an aqueous film (containing interference ions) commonly formed between the ISM and the metallic electrode, and restrict the accumulation of interfering ions in the interface, thus improving selectivity of the sensor to nitrate. In addition, the ISM-based sensing element can use a sandwiched solid-state reference electrode ($S^3RE$) to minimize chloride leaching and signal drifting, thus improving stability of the sensing unit.

The disclosed sensor uses a new flow-through soil water suction head. Ceramic porous capillary tubes have been widely used to extract soil water for analysis. The suction head is unique in that it utilizes a porous ceramic tube with openings at both sides. This design allows not only in situ sampling of soil water, but also in situ cleaning of the interior of the ceramic tube by simply flowing cleaning liquids from one side through the ceramic tube into a waste reservoir connecting on the other side of the tube. Therefore, every time after the soil water is sampled and analyzed, the suction head can be easily washed in situ, without pulling it out of the soil.

In addition, a nutrient sensing unit and a water-level sensor are directly made inside or socketed into a soil solution collector-to-detection cell. This integrated design eliminates the need of transporting extracted soil water from a collector to the sensing unit, thus not only simplifying the cost and footprint of the sensor system, but also reducing the amount of soil water (no more than 200 microliters) required for analysis.

Non-limiting Examples of Applications

1. Soil and water nutrients (N, P, S, K, etc.) detection in field. No substantial changes are required for using the same sensor system to detect nutrient in either soil or water.
2. Pesticide detection in field (by changing the working electrode of the sensor).
3. Water pollution (N, P, S, K, etc.) detection in field.

In addition, the disclosed fluid manipulation unit, the flow-through water extraction unit, and the system integration approach can be applied to many other existing soil and water sensor technologies to move these sensors from the laboratory to the field.

A further aspect of the invention comprises an integrated self-contained system that can include any or all of the above aspects. In one example, the system includes a soil water sampling head comprising a porous tube that is permeable to relevant gas/fluids in the soil but allows fluid flow in either direction through it. A ruggedized housing includes a chemical detection subsystem. In the case of ion-selective membrane (ISM) based detection, a sensing unit includes a reference electrode, a working electrode, an ion-selective membrane at the working electrode and an ion-to-electron interface between the membrane and the working electrode. In one example, the interface comprises $MoS_2$-POT.

Alternatives to POT include but are not limited to, other polymers, such as poly(3,4-ethylenedioxythiophene)-polystyrene sulfonate, polyaniline, and polypyrrole, can also be integrated with $MoS_2$ to form the ion-to-electron transducing layer.

Alternatives to a Nafion coating on top the PVB layer include but are not limited to, polyurethane can be coated to block both interfering anions and cations for minimizing chloride leaching from the PVB layer to surrounding environment.

A fluid manipulation subsystem includes soil water extraction and delivery fluid circuit that can be controlled to draw soil water and air into the sampling head and convey it to the detection cell. A controller can supply electrical power to the electrodes and collect data correlated to detection of a chemical species. Additionally, a reset/reconditioning fluid circuit can be selectively actuated to push cleaning fluid through the detection cell and sampling head after a detection cycle to refresh or recondition the system for a next sample.

In one aspect of the invention, an improved sensitivity sensor comprises a printed, coated, or otherwise applied nanocomposite of POT-$MoS_2$ as the ion-to-electron transfer layer of a working electrode and a printed, coated, or otherwise applied sandwiched solid-state reference electrode ($S^3RE$).

III. BRIEF DESCRIPTION OF THE DRAWINGS

The patent or application file contains at least one drawing or photograph executed in color. Copies of this patent or patent application publication with color drawing(s) will be provided by the Office upon request and payment of the necessary fee.

The appended drawings will be referred to in the detailed description of exemplary embodiments and are summarized as follows.

Figure 1:
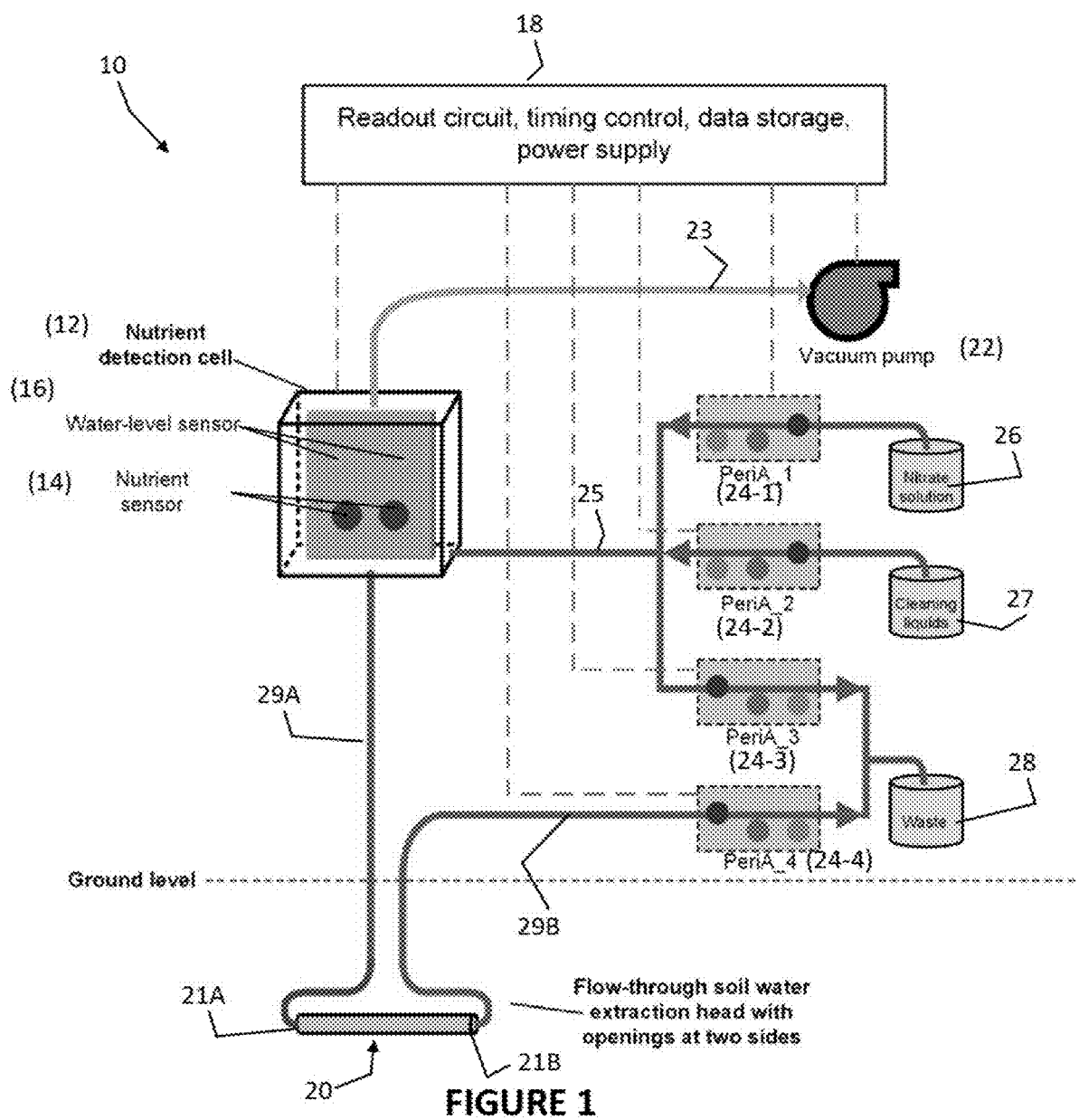
FIG. 1 is a diagrammatic view of certain features of an overall system according to one embodiment of the invention, a self-contained, ion-selective sensor system.
Figure 2:
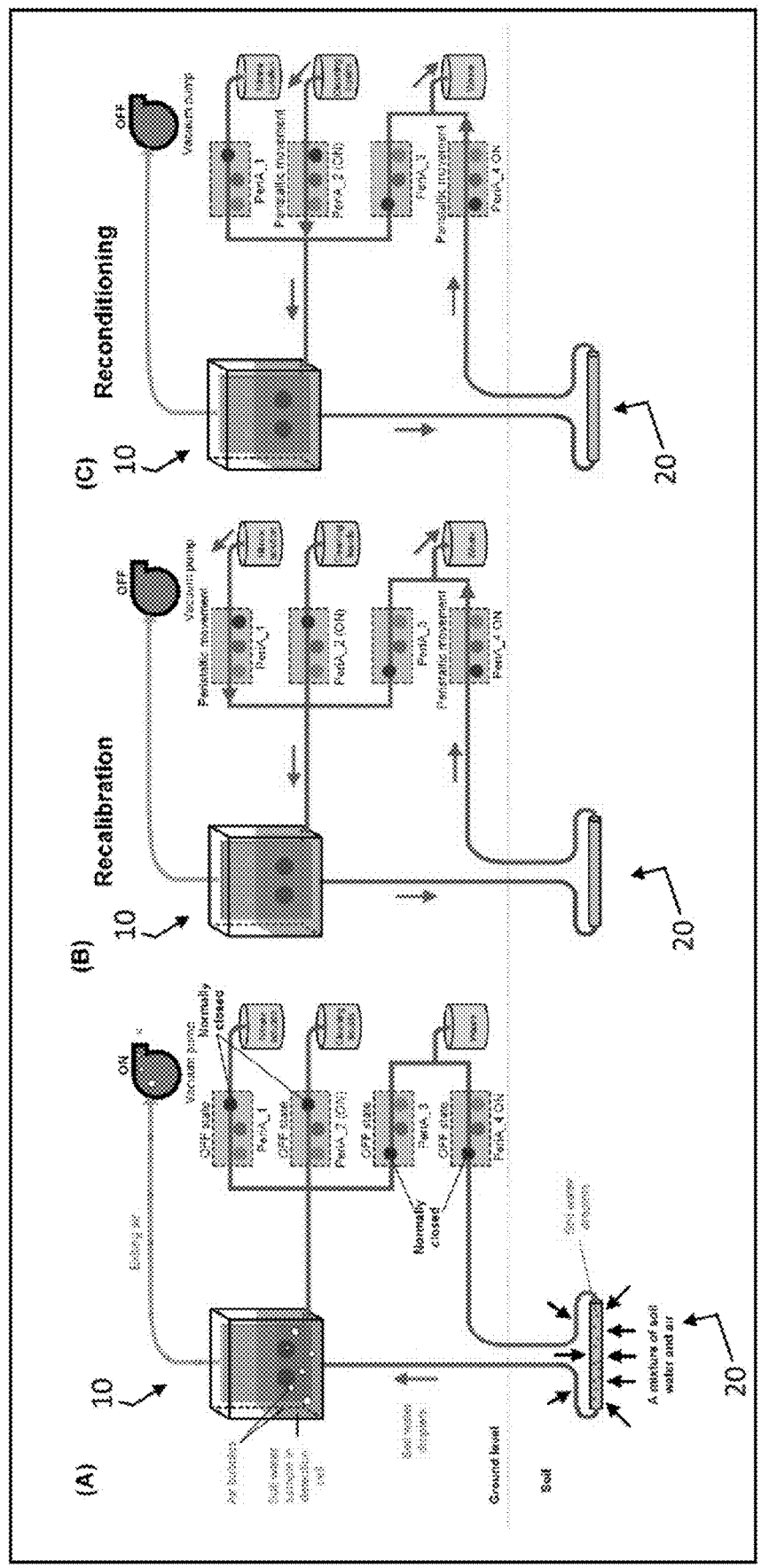
FIG. 2 are similar to FIG. 1 but show a first operational state of fluid manipulation from a fluid collection sampling head to a detection cell for electrochemical sensing (FIG. 2A) and a second state of recalibration after a first measurement (FIG. 2B), and fluid manipulation of cleaning out/reconditioning the system to reset it for a next detection cycle (FIG. 2C).
Figure 3:
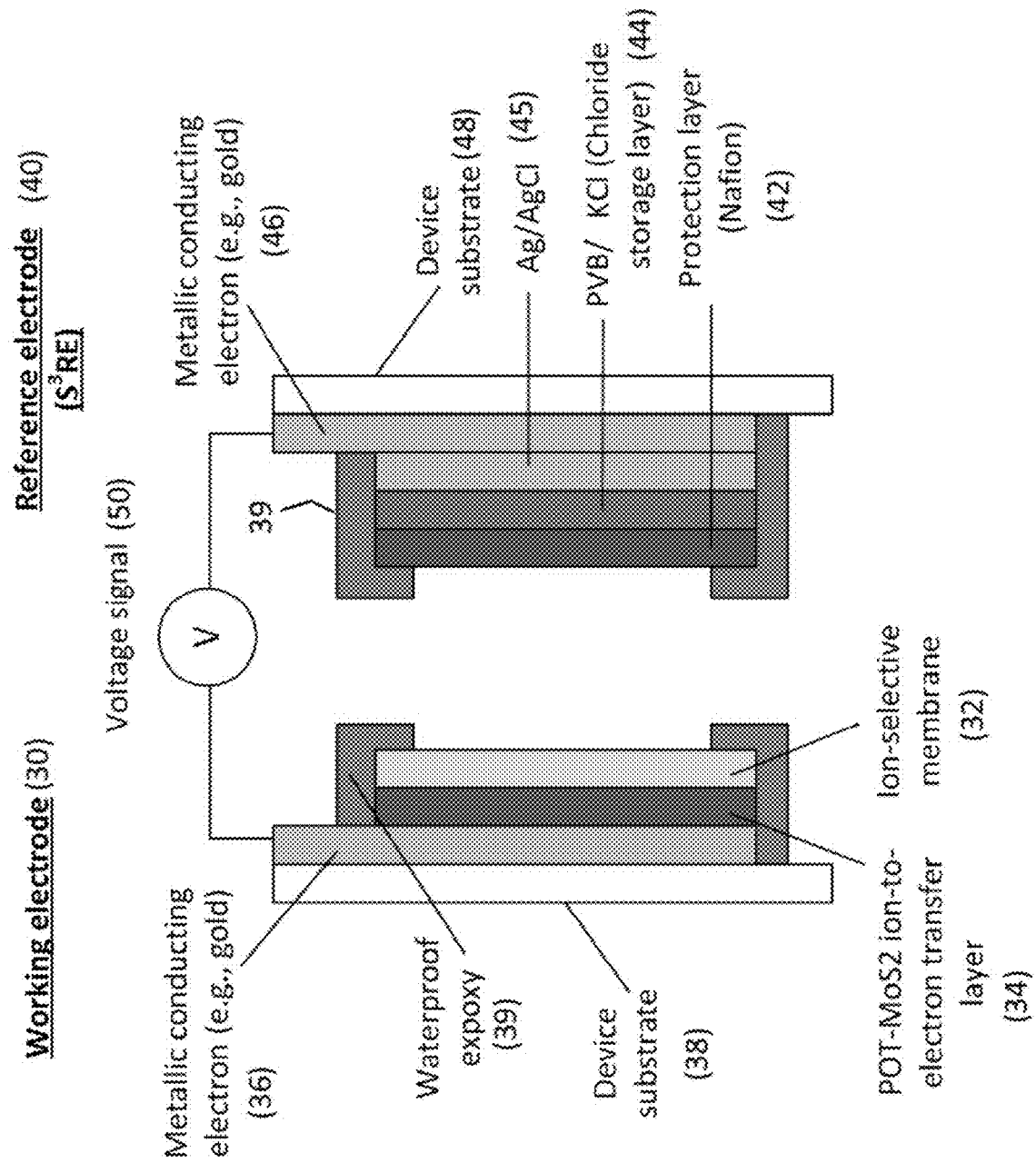
FIG. 3 is an enlarged diagrammatic depiction of a modified electrode-based ion-selective detector including an ion-to-electron transfer layer between ion-selective membrane and metallic conducting electrode according to one aspect of the invention.

FIGS. 4A-E are a collection of photographs showing different features of a complete, field-deployable sensor system such as could be used with the systems of FIGS. 1-3. Each of FIGS. 4A-E is reproduced in enlarged form on succeeding pages of the drawings. Note that the enlargement of FIG. 4E includes an added diagrammatic illustration of the porous ceramic tube of FIG. 4E.

Figure 5:
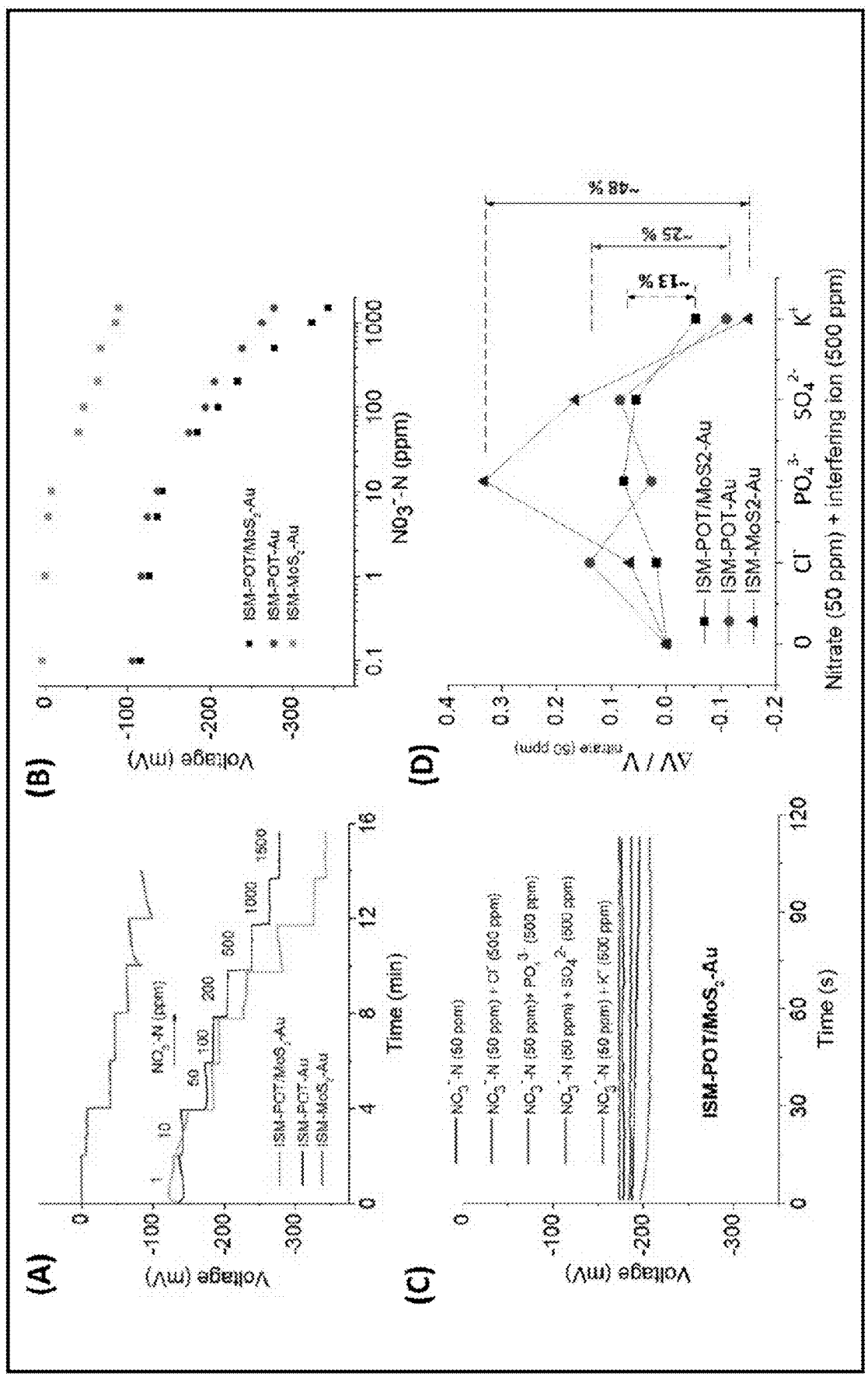

FIG. 5 is a graph illustrating efficacy of improved sensitivity of the sensor of FIG. 3. FIG. 5 shows: (A) (B) Sensitivity test: voltage responses of the sensor to changing nitrate concentrations. The sensors used the POT-$MoS_2$ nanocomposite, POT, and $MoS_2$ in their working electrodes. (C) (D) Selectivity test: voltage responses of the sensor to a mixture of nitrate (50 ppm) and different interfering ions (500 ppm each). The sensor used the POT-MoS2 nanocomposite in its working electrode.

Figure 4A:
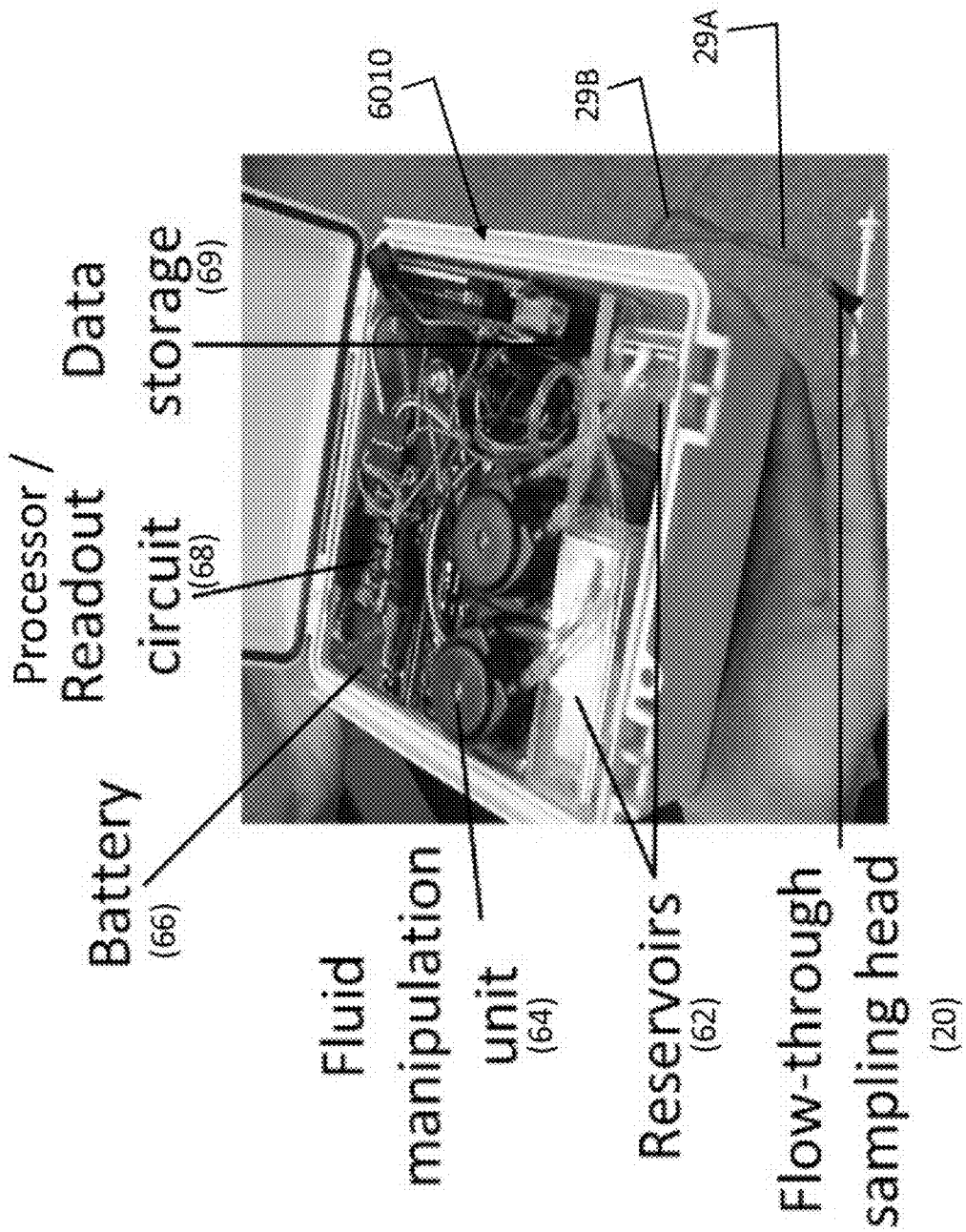
Figure 6:
Figure 7:
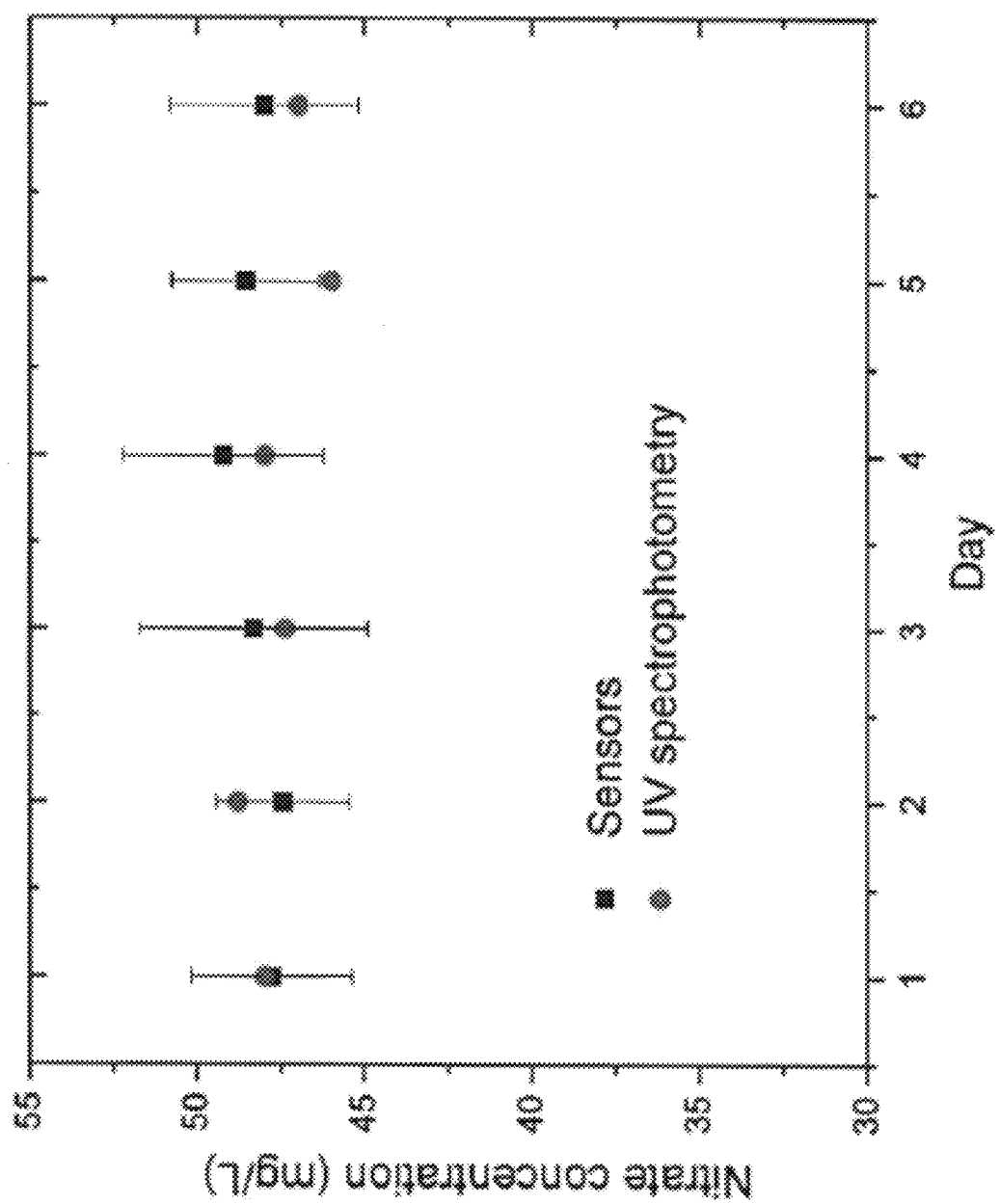

FIG. 6 is a photograph of an overall system such as FIG. 4A packed in a thermally insulated covering and a plurality of which are installed at spatially separated distance in a field for measuring soil nutrient levels at different points in the field. FIG. 6 is illustrations of a field installation of the ion-selective sensor systems according to the invention. Fifty-four sensors have been installed in the field of an initial field testing FIG. 7 is a graph showing measurements throughout several days by a sensor such as FIG. 6 compared to a calibration measurement at the same location and times with a UV spectrophotometry based detector. FIG. 7 are typical measurement data from field deployable sensors according to the invention.

Figure 8:
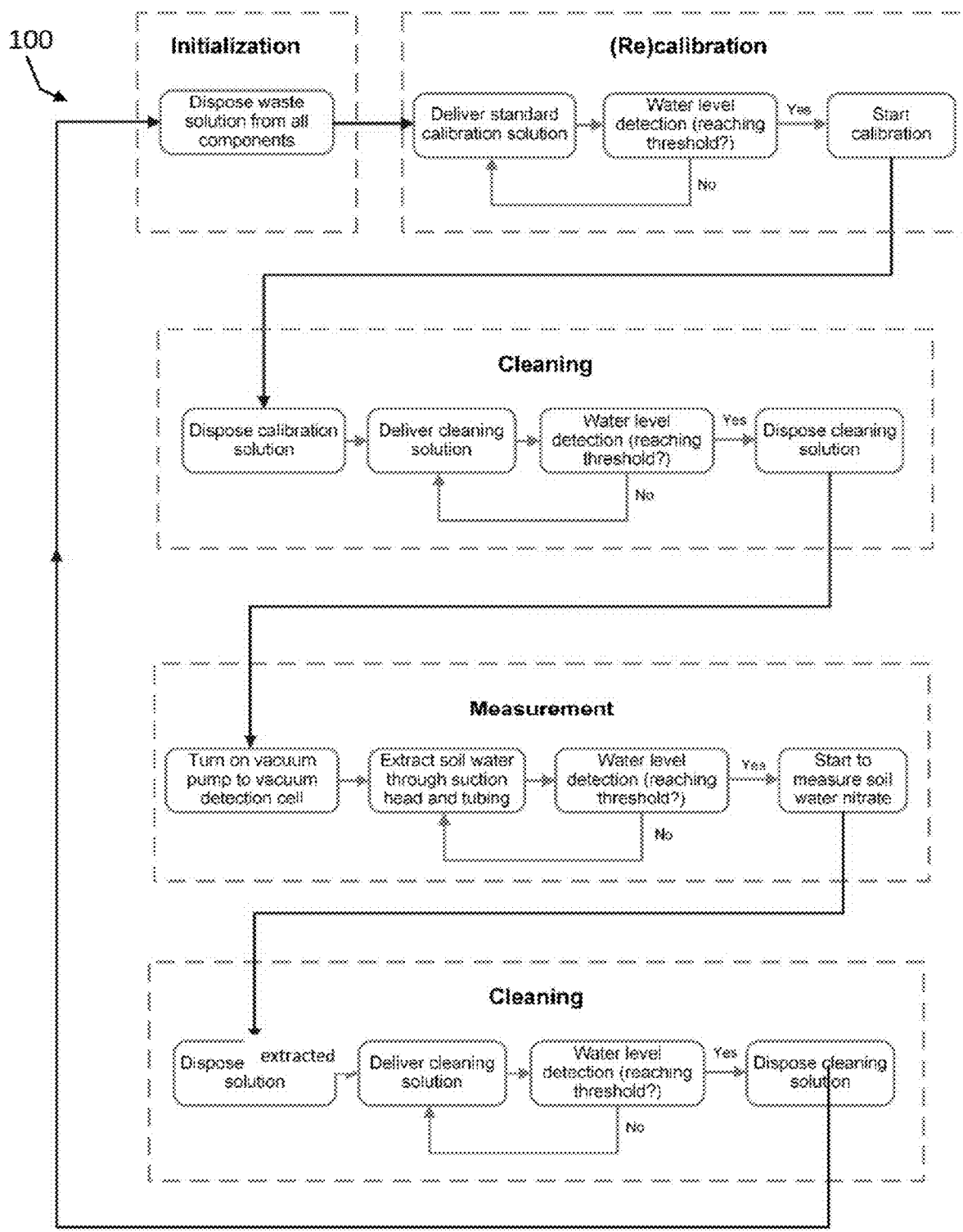

FIG. 8 is a flow chart showing one exemplary methodology of using the sensor system of FIGS. 1-7.

Figure 9:
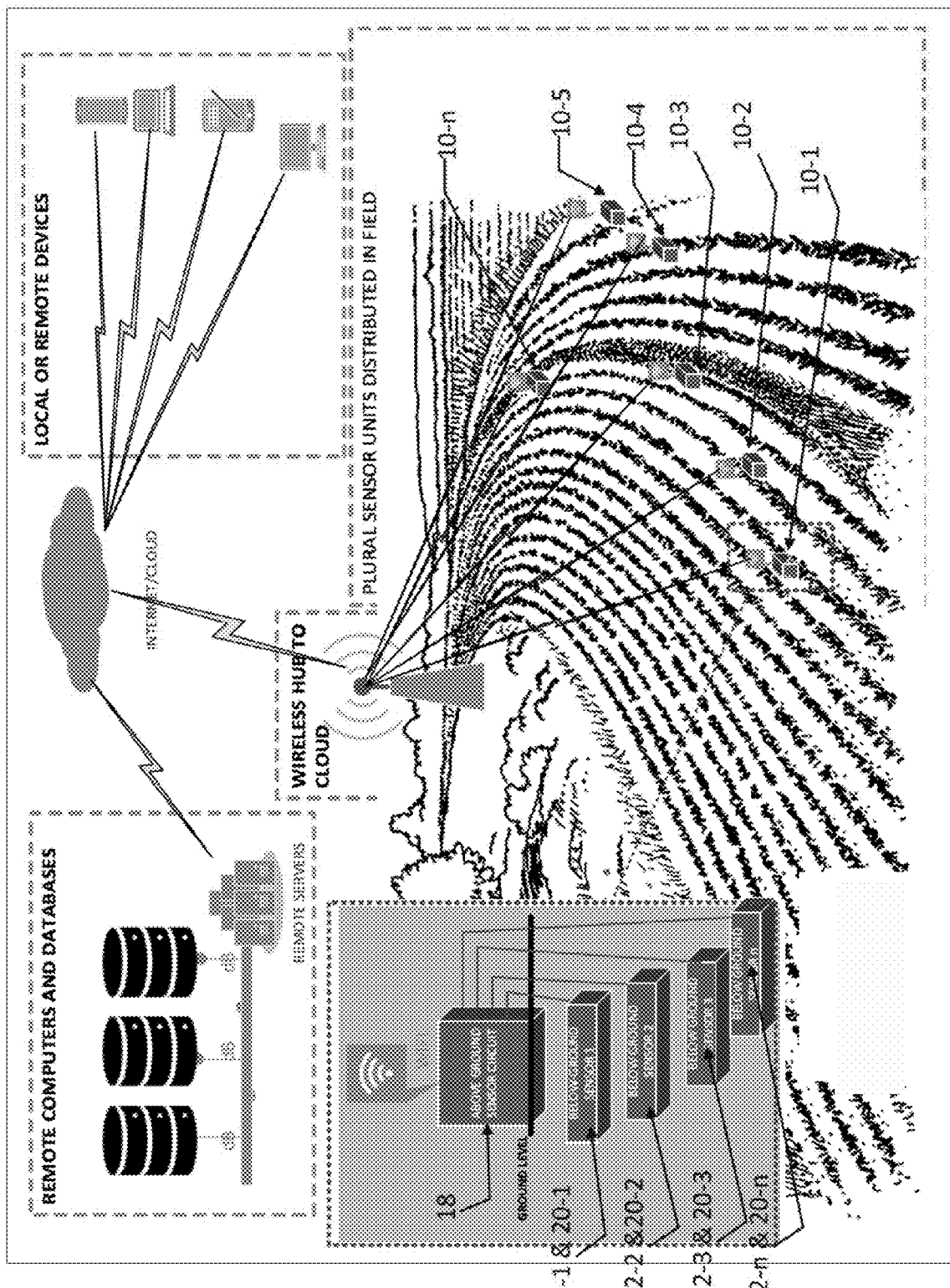

FIG. 9 is a diagrammatic view of a variety of options regarding to sensor unit placement and communications capabilities.

Figure 10:
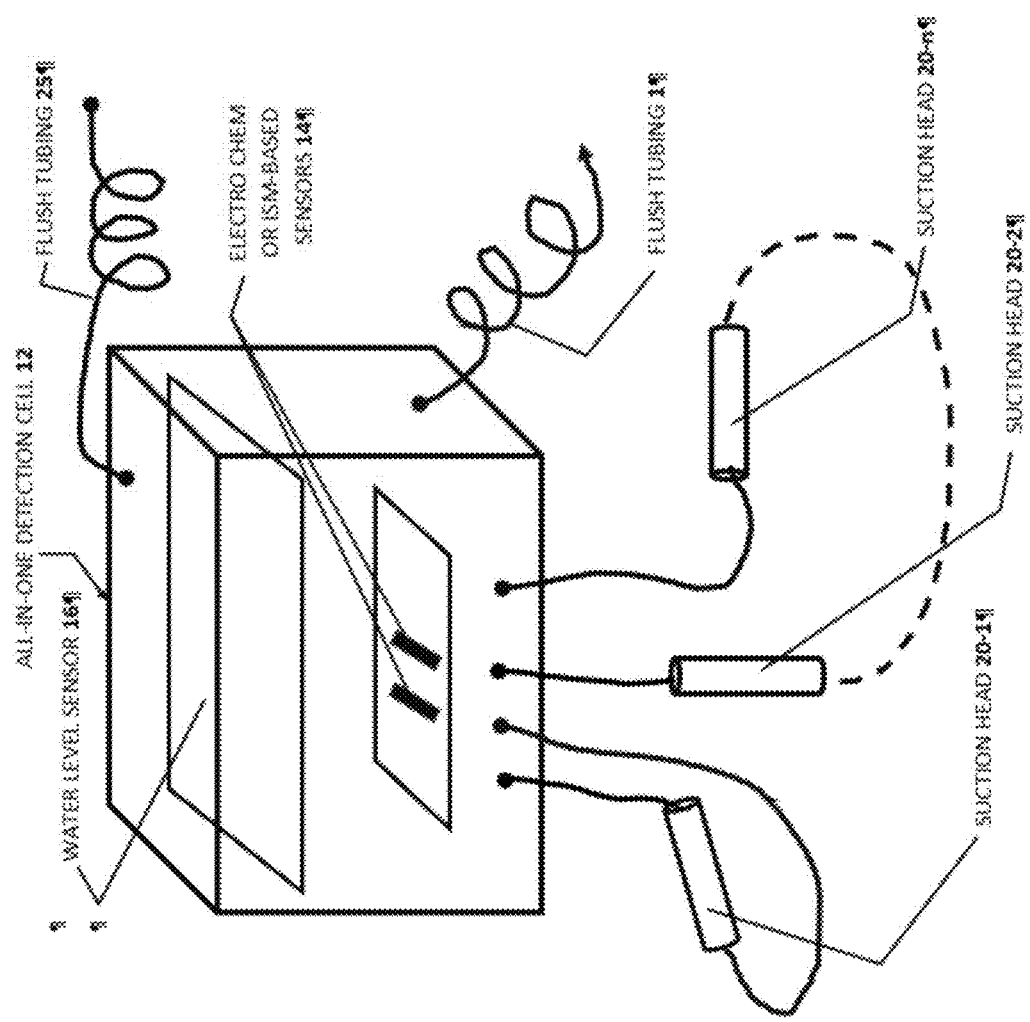

FIG. 10 is a diagrammatic view of a system like FIG. 1 but showing some alternatives. FIG. 10 shows a non-limiting exemplary all in one detector unit including:

Electrochem sensors or ISM-based sensors in detection unit.

Suction head allows permeable infiltration of soil water/air via vacuum and bi-directional flow between ends.

Suction head (single or plural) can be placed in situ at different heights for sensing different depths and allow differentiation detection by varying length of tubing.

Fluid manipulation allows movement of soil water/air from suction head to detection unit.

Water level sensor in detection unit—two electrode sensors—allows automated detection of enough sample loading.

Peristaltic actuation and check valve(s) with flush tubing to opposite ends of suction head allows flushing/cleaning/reset of system. Essentially "artificial rain" to clear out system for next measurement.

FIGS. 11 to 19 are illustrations and graphs relating to a specific embodiment Example 1 discussed herein of a sensor that can be used with the present invention, in particular, to a solid state sensor using a printed nanocomposite of POT-MoS$_2$ as the ion-to-electron transfer layer of a working electrode and a printed sandwiched solid-state reference electrode (S$^3$RE) for measurement of soil or water nutrients.

Figure 11:
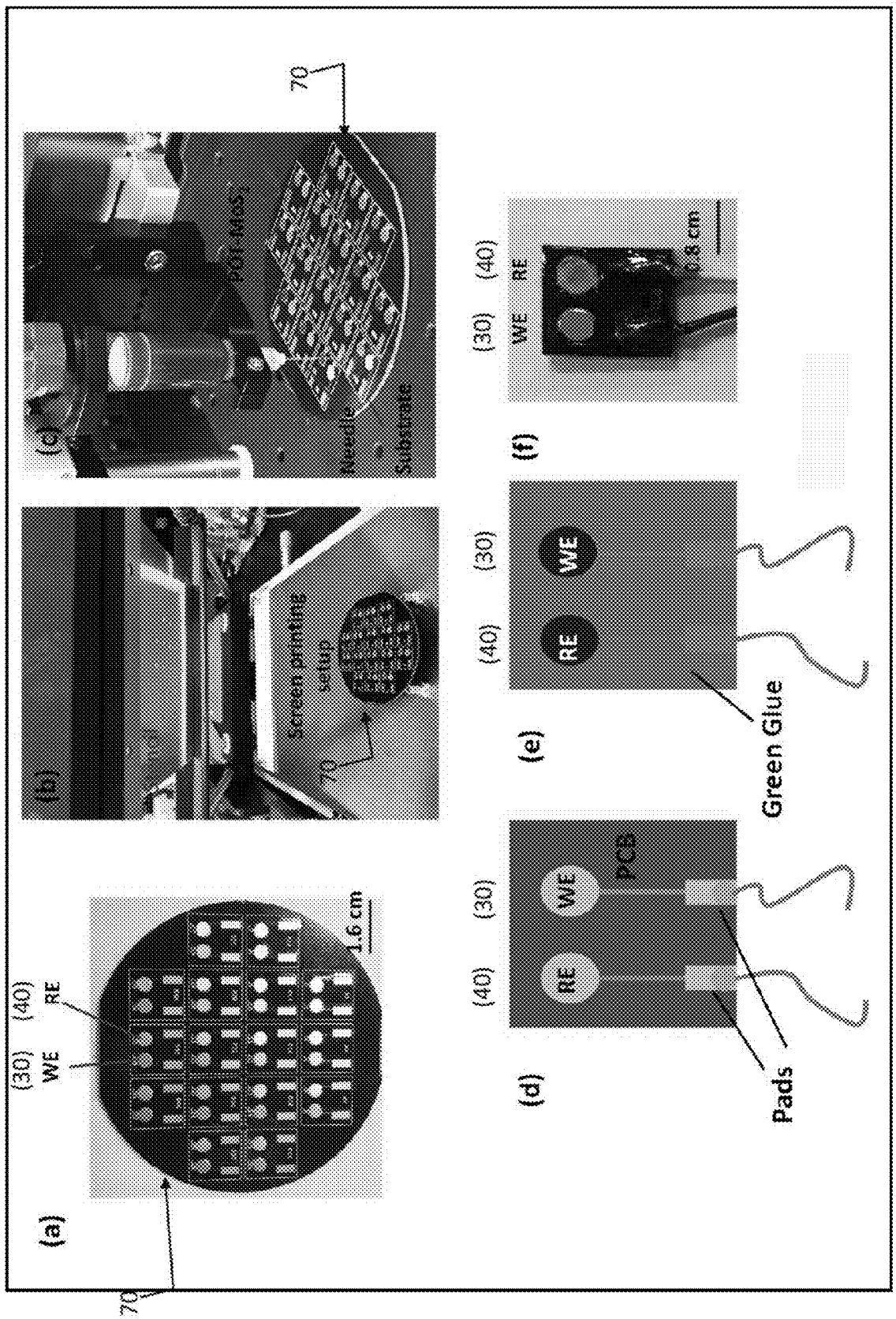

FIG. 11 is a step-wise representation for the fabrication of all-solid-state ion selective sensor. (a) A photograph of wafer-scale PCB containing a series of WE and RE. (b) Stencil-based screen printing setup for printing Ag/AgCl paste on the circular shaped silver (Ag) PCB substrate. (c) A photograph during materials dispensing (POT-MoS$_2$ in THF solvent) on circular-shaped electrodes using high-precision Nordson EFD auto-dispenser at 2 psi pressure. A 100 cc syringe with 0.05 mm diameter of tip is loaded POT-MoS$_2$ material to deposit. (d) Schematic presentation of PCB substrate containing RE and WE with wire connections and (e) both electrodes were modified with electrode materials and green glue covering side-wall coating and connection pads. (f) A photograph of real device.

Figure 12:
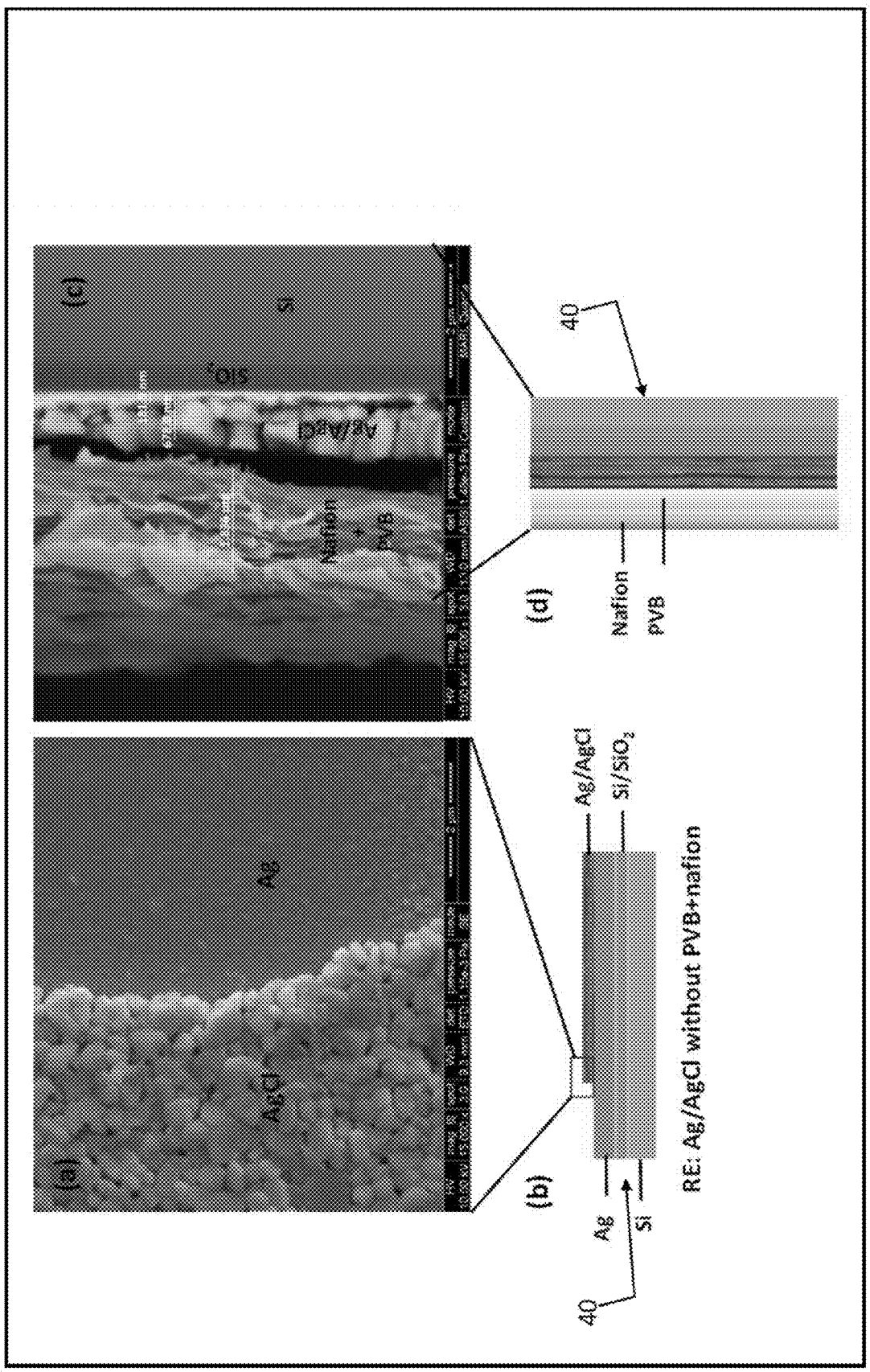

FIG. 12 is (a) Scanning electron microscopic (SEM) image for Ag/AgCl surface on Si needle, (b) schematic for different layers of the home made reference electrode on Si/SiO$_2$. (c) SEM image the cross-sectional view of PVB and Nafion layers on top of the Ag/AgCl substrate. (d) Schematic shows the different layers for the formation of S$^3$RE.

Figure 13:
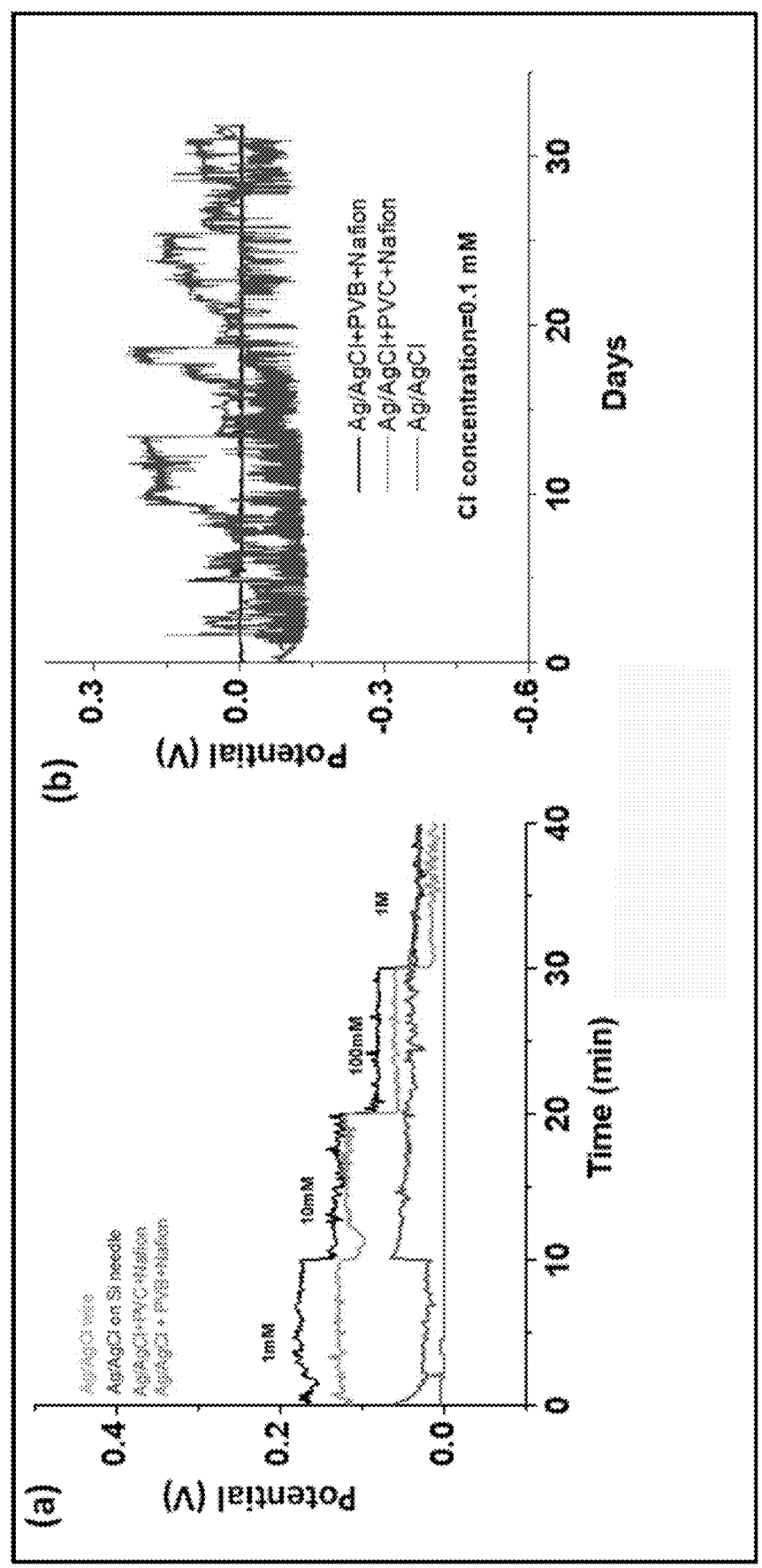

FIG. 13 is (a) Chloride sensitivity studies for different fabricated electrodes by varying Cl$^-$ ions concentration. The measurements were conducted using a commercial RE with respect to fabricated electrodes. (b) Long-term studies for different electrodes at 0.000M Cl$^-$ concentration. The commercial RE is obtained from eDAQ Pty. Ltd. (leak-less miniature Ag/AgCl RE; internal filling solution: 3.4 mol/L KCl; model: ET072).

Figure 14:
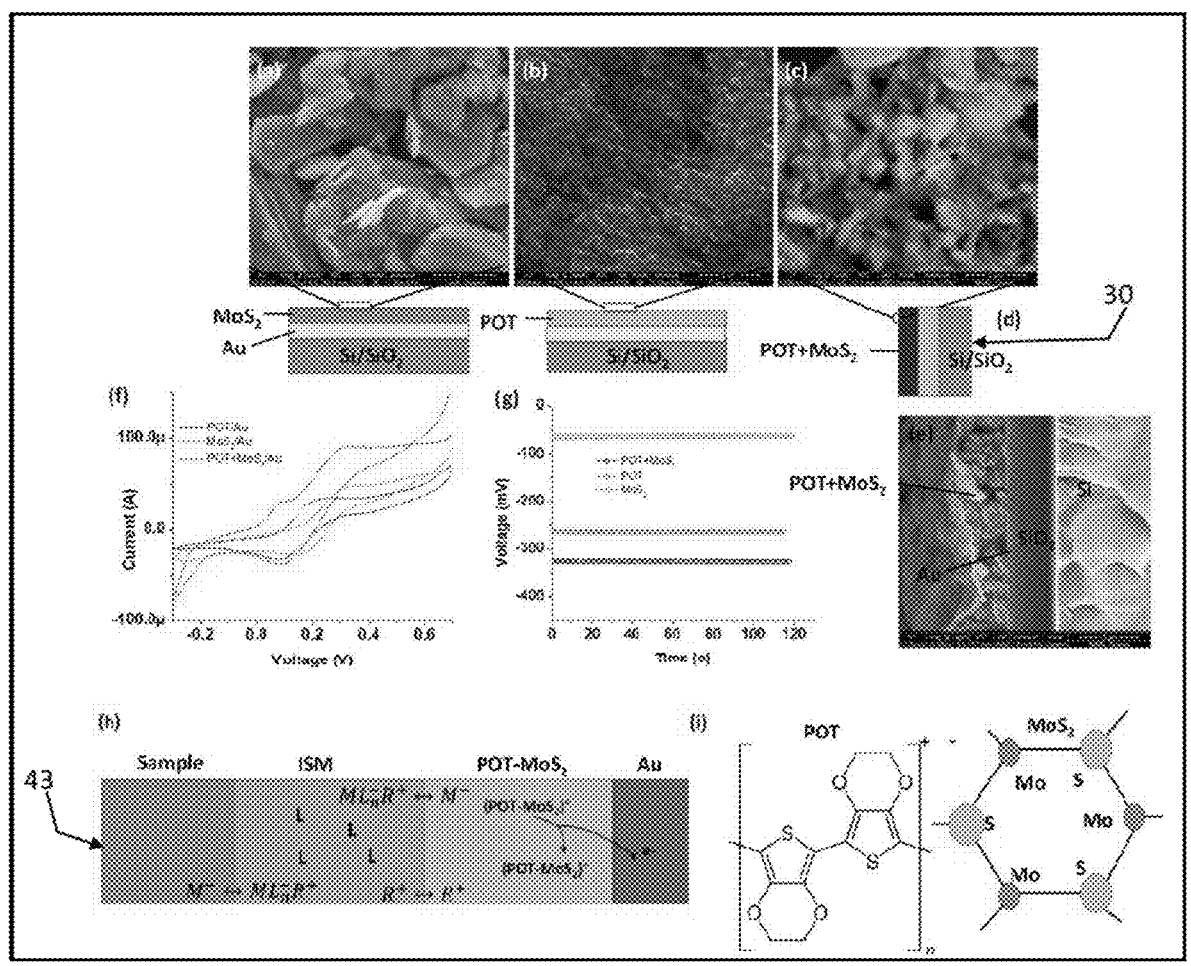

FIG. 14 is SEM images for MoS$_2$ (a), (POT) (b) and POT-MoS$_{2\ (c)}$. (d) Schematic shows the different layers for working electrode (e) cross-sectional view of the working electrode showing the different layers, (f) cyclic voltammetry of MoS$_2$, POT and POT-MoS$_2$ electrodes in presence of buffer solution (containing 2 mM of ferro/ferricyanide redox species) and (g) voltage measurements of all three electrodes in presence of 1000 ppm NO$_3$—N. In this measurements (g), all electrodes were coated with nitrate ions selective membrane and was carried out in nitrate solution. (h) A pictorial presentation for the formation of all relevant interfaces in the fabricated all-solid-state sensor. Anion (M) selective membranes contains an electrically neutral ionophore (L) and cationic sites (R$^+$). (i) Molecular structure of POT and MoS$_2$ for composite formation in this sensor.

Figure 15:
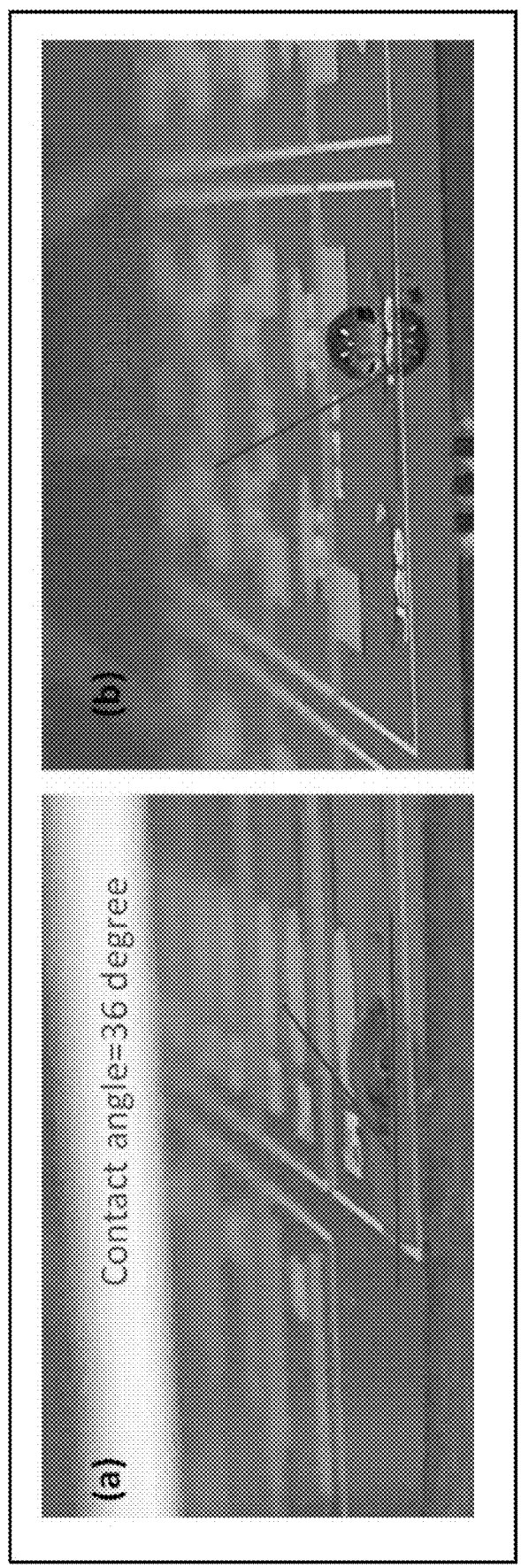

FIG. 15 is the contact angle studies for the investigation of hydrophobicity of the working electrode materials. A syringe was used to drop 3 µL volume of DI water on the Au/PCB substrate coated with different working electrode materials including POT (a) and POT-MoS$_2$ (b).

Figure 16:
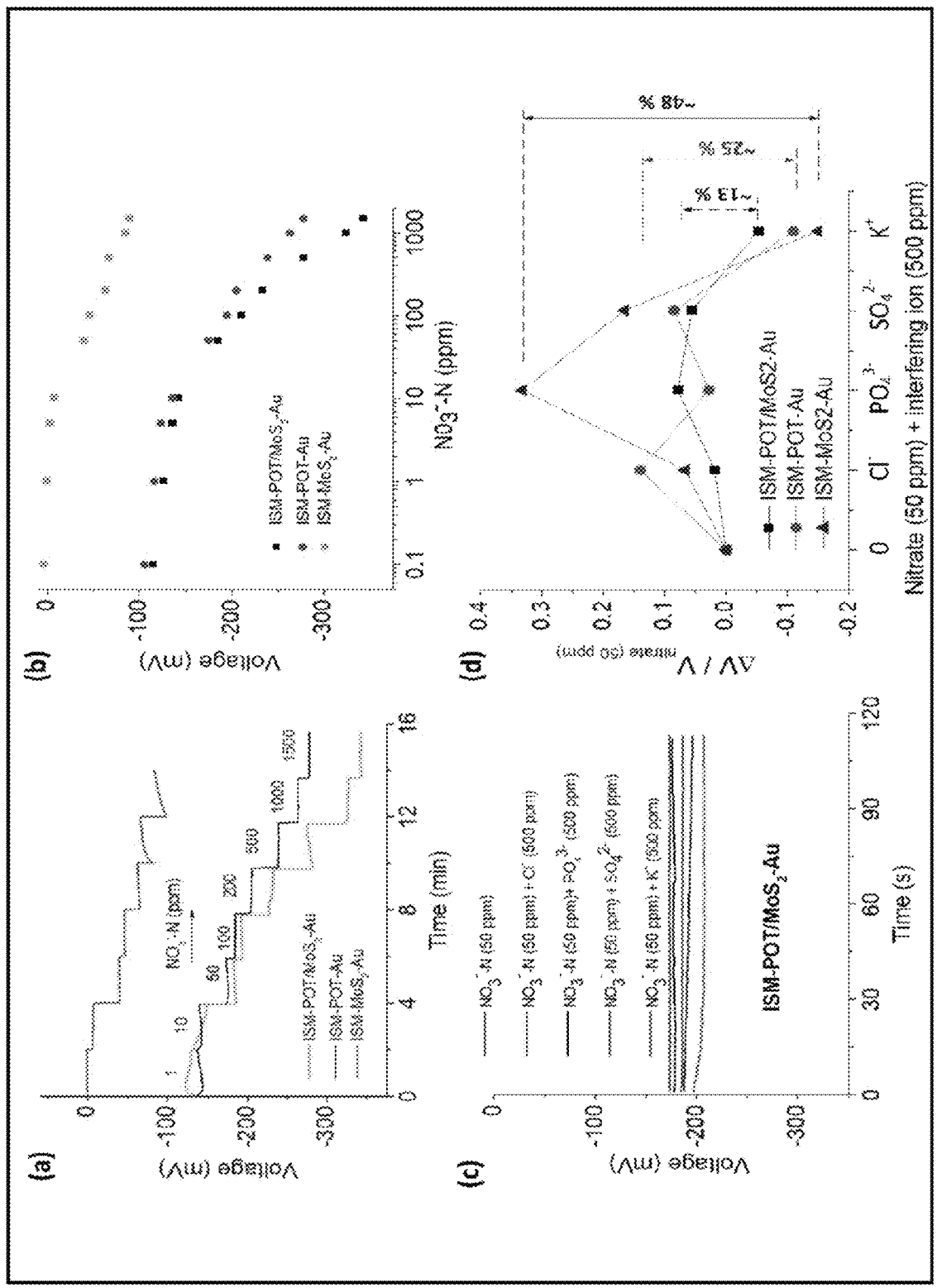

FIG. 16 is (a)-(b) Sensitivity test: voltage responses of the sensor to changing nitrate concentrations. The sensors used the POT-MoS2 nanocomposite, POT, and MoS$_2$ in their working electrodes. (c)-(d) Selectivity test: voltage responses of the sensor to a mixture of nitrate (50 ppm) and different interfering ions (500 ppm each). The sensor used the POT-MoS2 nanocomposite in its working electrode.

Figure 17:
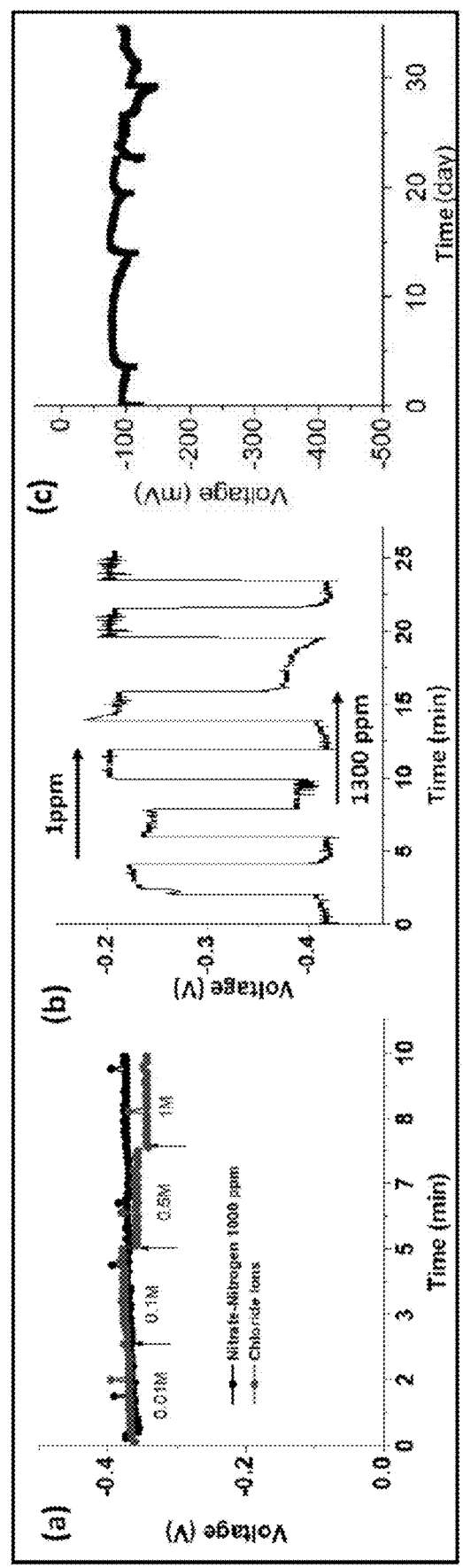

FIG. 17 is (a) and (b) repeatability test for the fabricated sensor made of ISM/POT-MoS$_2$/Au in presence of 1 ppm and 1300 ppm of nitrate-nitrogen solution. (c) Long-term stability test of the sensor in presence of 5 ppm of nitrate-nitrogen.

Figure 18:
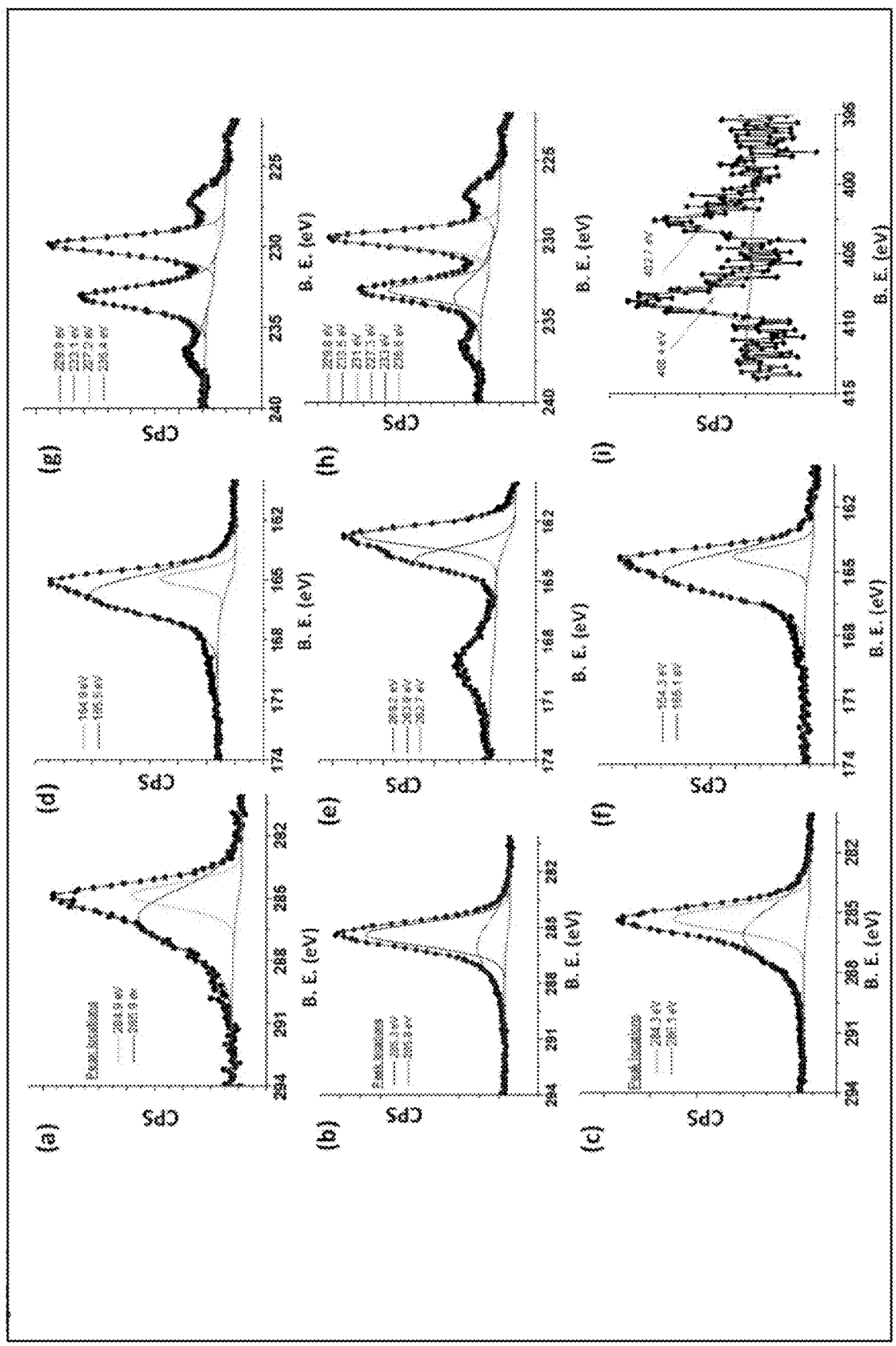

FIG. 18 is XPS analysis for the printed electrodes made by POT, MoS$_2$, POT-MoS$_2$ and ISM/POT-MoS$_2$ materials. For this study, these materials were printed on the surface of silicon. The XPS spectra of the carbon is region of MoS$_2$ (a), POT-MoS$_2$ (b) and ISM/POT-MoS$_2$ (c). Sulphur (S 2p) peaks for the MoS$_2$ (d), POT-MoS$_2$ (e) and ISM/POT-MoS$_2$ (f) electrodes. XPS peaks for molybdenum (Mo) 3d found for the MoS$_2$ (g) film and POT-MoS$_2$ (h) film. XPS spectra for the nitrogen is peaks region of ISM/POT-MoS$_2$ film (i).

Figure 19:
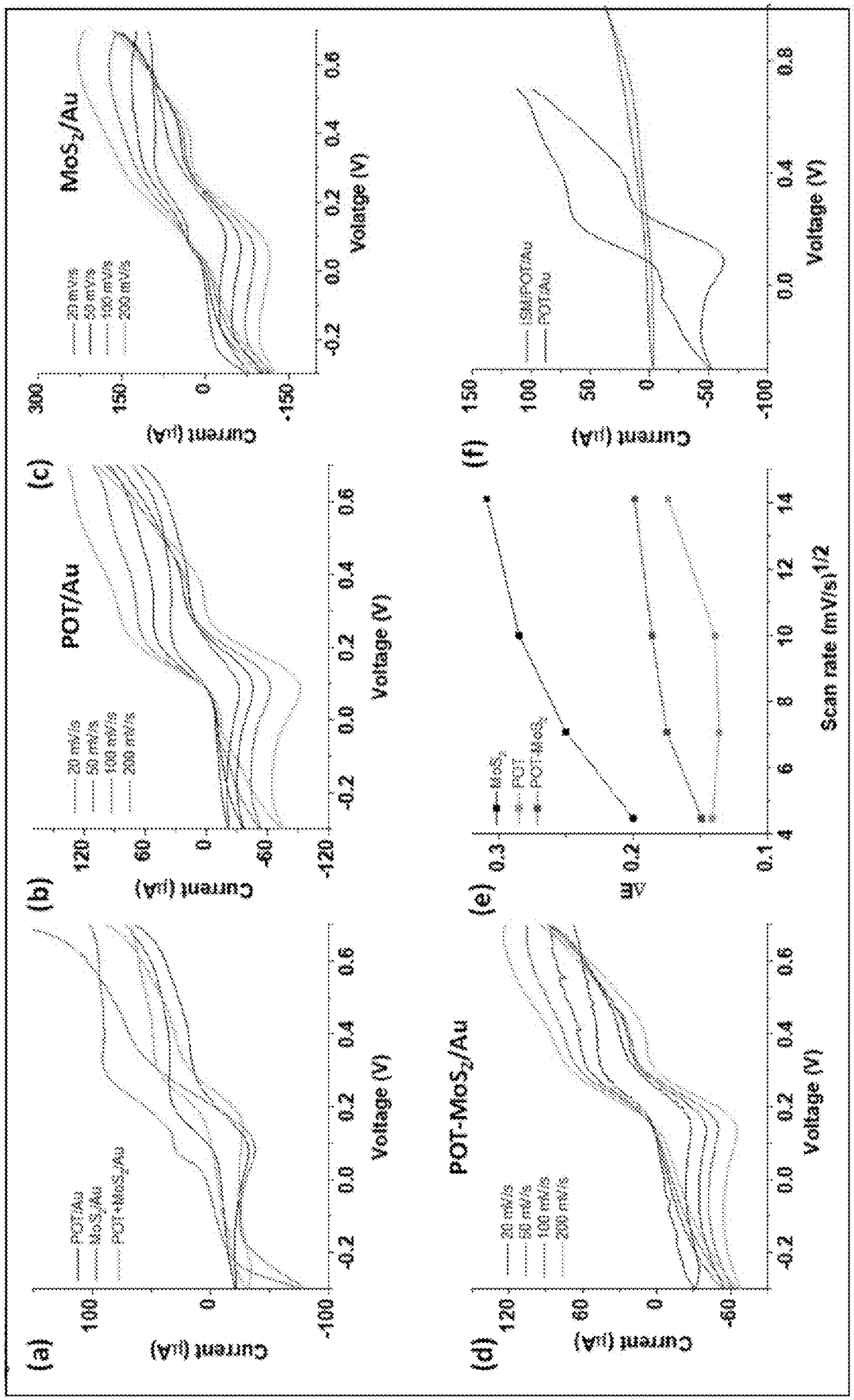

FIG. 19 is at graph (a) cyclic voltammetry (CV) studies of MoS$_2$, POT and POT-MoS$_2$ electrodes. These experiments were conducted using phosphate buffered saline (PBS) solution mixed with a 2 mM concentration of ferro/ferricyanide ([Fe(CN)$_6$]$^{3-/4-}$. CV responses for the POT/Au (graph (b)), MoS$_2$/Au (graph (c)) and POT-MoS$_2$ (graph (d)) by varying scan rate from 20 mV/s to 200 mV/s. Potential differences versus root square of scan rates for all fabricated electrodes are at graph (e). CV responses of POT/Au electrode with and without ion selective membrane are at graph (f).

FIGS. 20 to 29A-C relate to a second Specific Example 2 according to aspects of the present invention.

Figure 20:
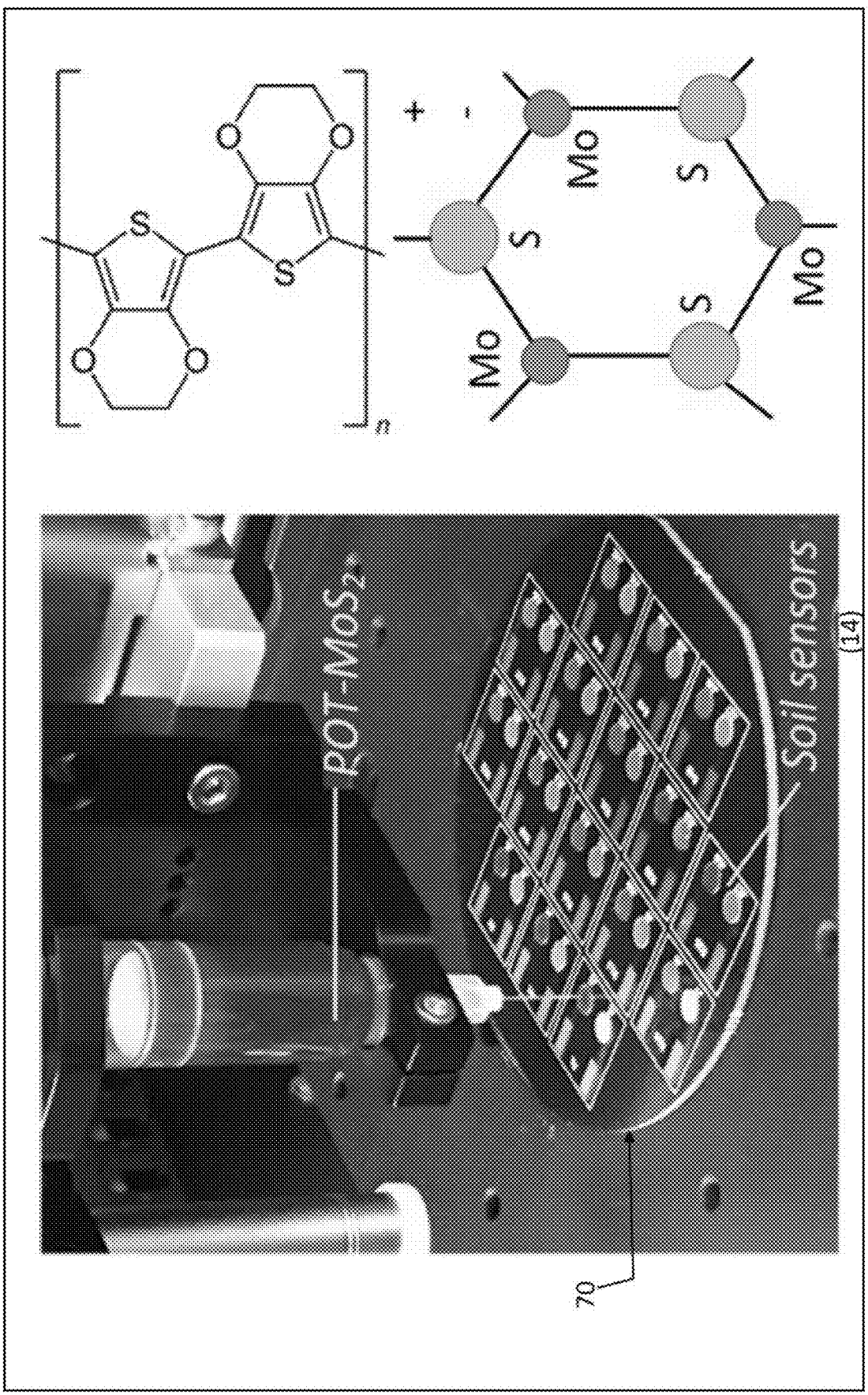

FIG. 20 is a diagrammatic depiction of concepts from the Example 2 according to aspects of the present invention.

Figure 21:
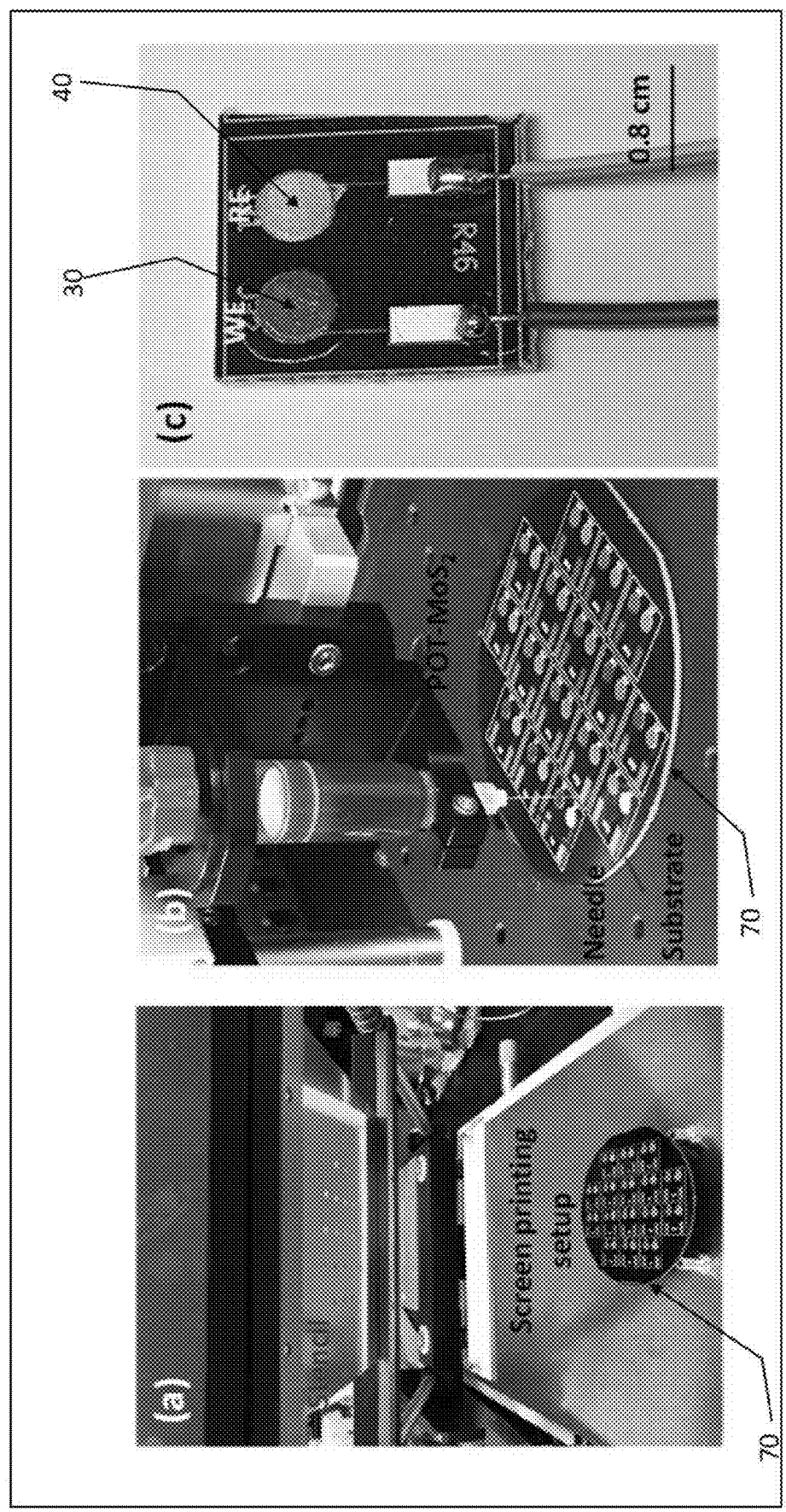

FIG. 21 relates to the Example 2 and is a stepwise representation of the fabrication of all-solid-state soil nitrate sensor. (a) Photograph taken during printing Ag/AgCl paste on circular-shaped silver (Ag) electrodes using a stencil printer. (b) Photograph taken during materials dispensing (POT-MoS$_2$ in THF solvent) on circular-shaped Au electrodes using a programmable high-precision automated fluid-dispensing robot. (c) Photograph of the device.

Figure 22:
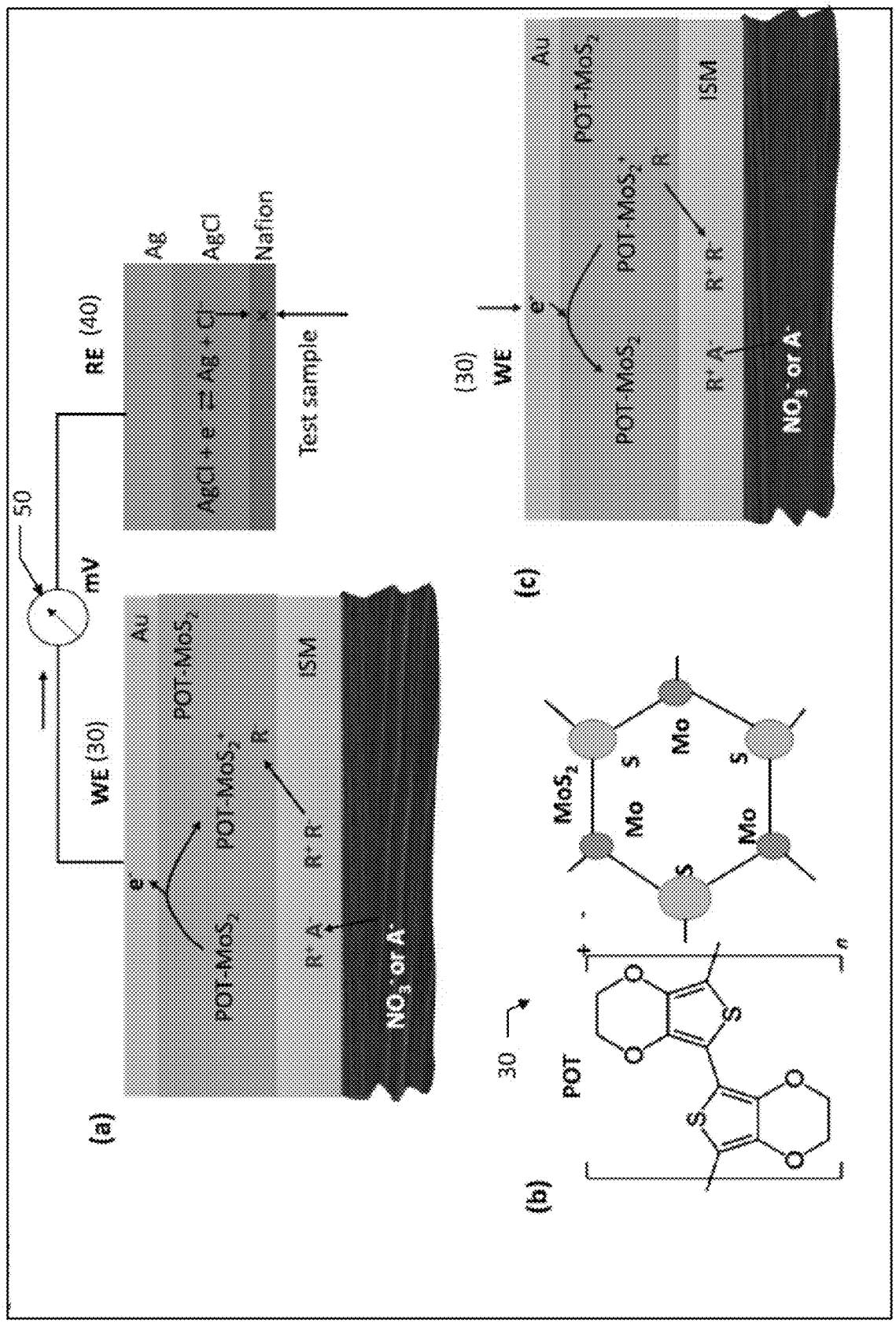

FIG. 22 relates to the Example 2 and is a schematic of the working principle of the soil sensor. (a) Oxidation process for the WE (ISM/POT-MoS$_2$/Au) in the presence of soil solution NO$_3^-$ ions. R$^+$ and R$^-$ represent the anion and cation exchangers at the organic membrane, and M$^+$ and A$^-$ are the hydrophilic ions in soil water. POT-MoS$_2$ and POT-MoS$_2{}^+$ indicate neutral and oxidized POT-MoS$_2$ units. Oxidation/reduction is shown for the Ag/AgCl RE. (b) Molecular structure of POT and MoS$_2$ for composite formation in this sensor. (c) Mechanism of the reduction process for the WE (ISM/POT-MoS$_2$/Au).

Figure 23:
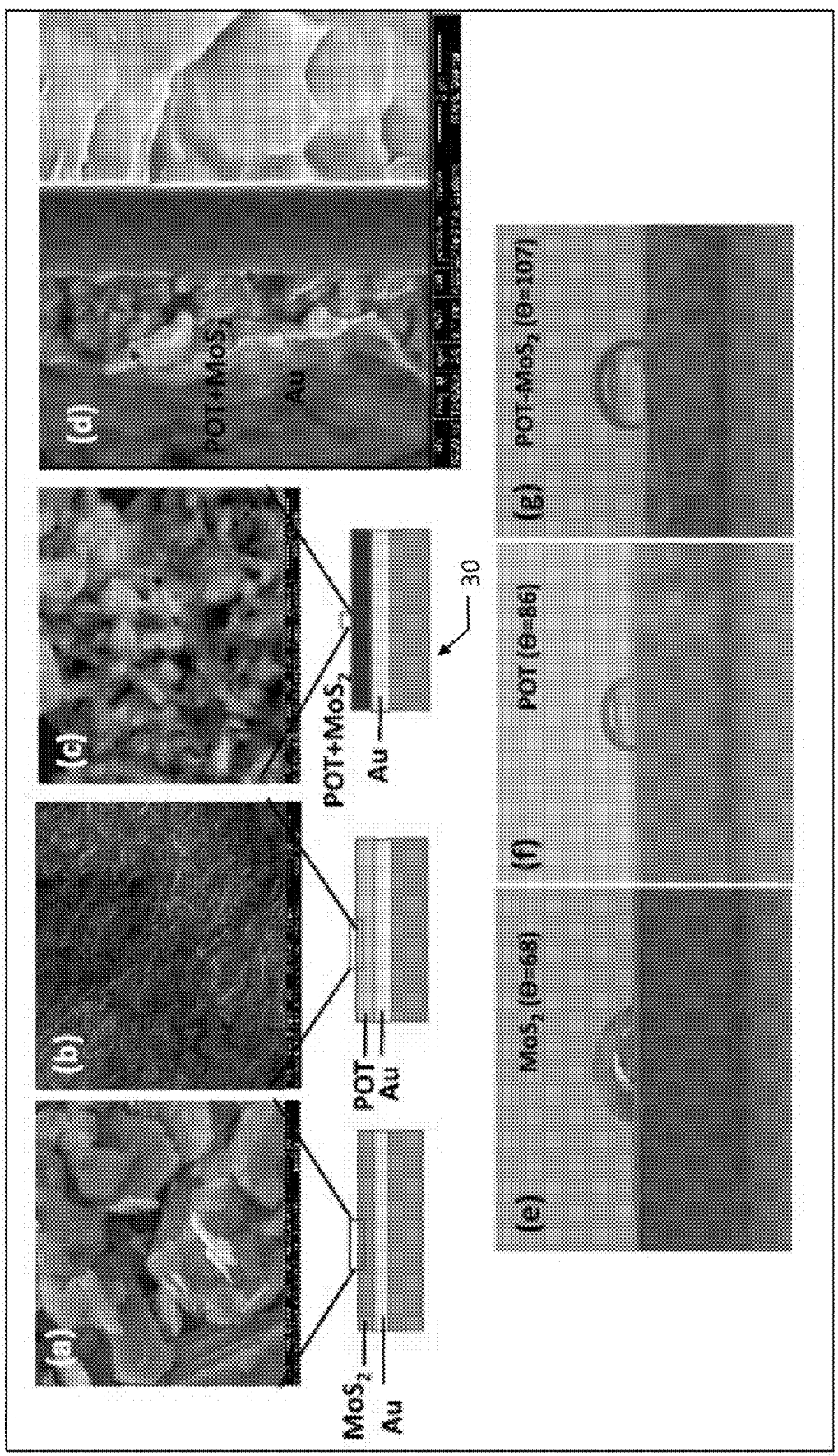

FIG. 23 relates to the Example 2 and is a scanning electron micrographs for MoS$_2$ sheets (a), POT (b), and POT-MoS$_2$ materials (c) with schematic representation of various layers. (d) Cross-sectional view of the SEM image for the POT-MoS$_2$ composite on Au. Contact angle (CA or Θ) studies for the investigation of the hydrophobicity of the WE materials. A syringe was used to drop 3 µL volume of deionized water on the Au/PCB substrate coated with different WE materials, including MoS$_2$ (e), POT (f), and POT-MoS$_2$ (g). Images were analyzed using image J plugin software.

Figure 24:
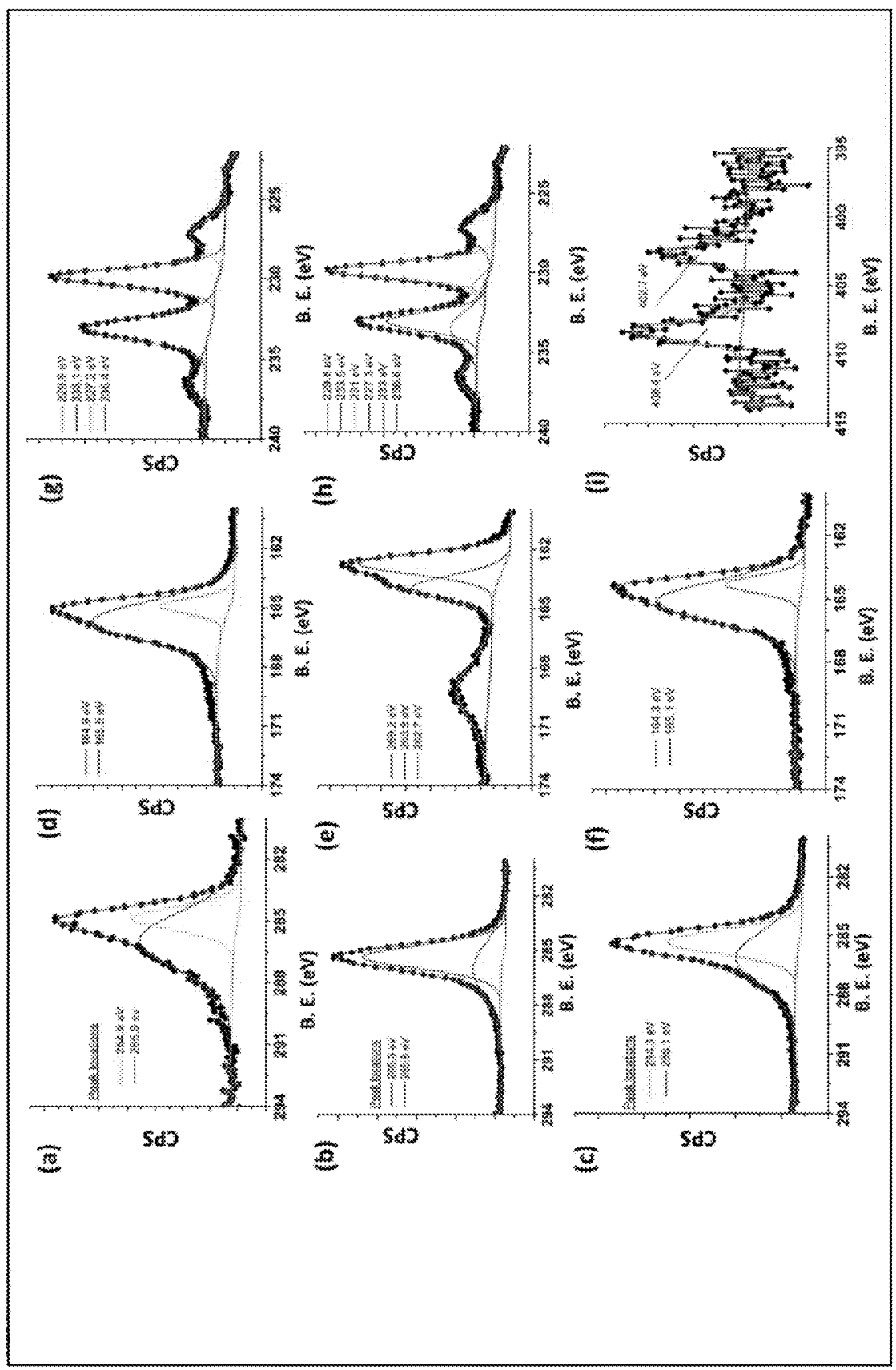

FIG. 24 relates to the Example 2 and is an XPS analysis for the WEs using MoS$_2$, POT-MoS$_2$, and ISM/POT-MoS$_2$ materials. XPS spectra of the carbon is region of MoS$_2$ (a), POT-MoS$_2$ (b), and ISM/POT-MoS$_2$ (c). Sulfur (S 2p) peaks for the MoS$_2$ (d), POT-MoS$_2$ (e), and ISM/POT-MoS$_2$ (f) electrodes. XPS peaks for molybdenum (Mo) 3d found for the MoS$_2$ (g) film and POT-MoS$_2$ (h) film. XPS spectra for the nitrogen 1 s peak region of the ISM/POT-MoS$_2$ (i) film.

Figure 25:
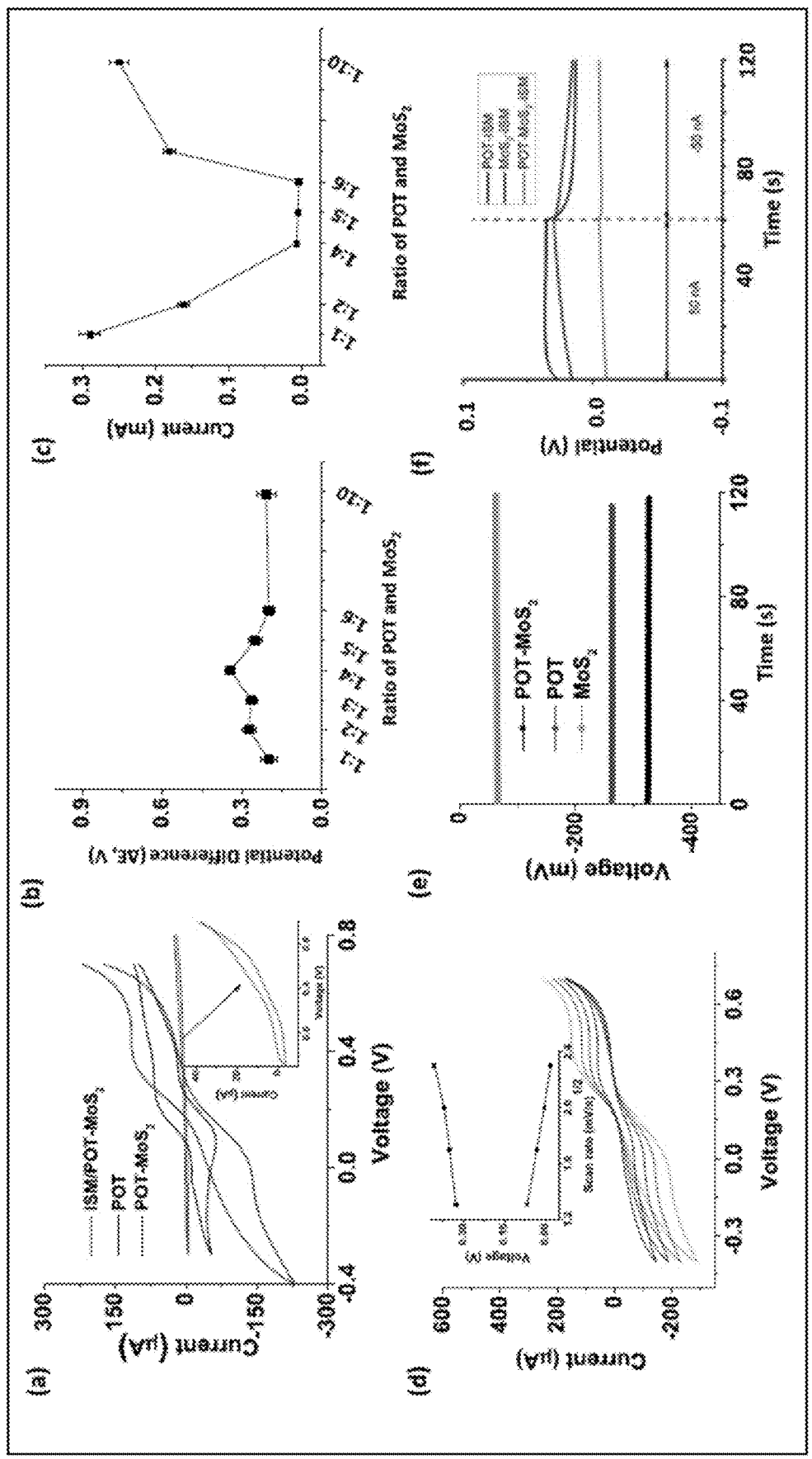

FIG. 25 relates to the Example 2 and is a (a) CV for different electrodes: MoS$_2$, POT, POT-MoS$_2$, and ISM/POT-MoS$_2$. These experiments were conducted using a phosphate buffered saline solution mixed with a ferro-/ferricyanide species ([Fe(CN)$_6$]$^{3-/4-}$) of concentration 2 mM. Inset shows the zoomed CV curve of ISM/POT-MoS$_2$. (b) Potential differences (ΔE) obtained from the CV curves plotted against the ratio of POT-MoS$_2$-based electrodes. In the composite formation, the ratio of POT to MoS$_2$ was varied from 1:1 to 1:10 by weight percentage. (c) Oxidation current obtained from the CV curves vs the ratio of POT to MoS$_2$ (1:1 to 1:10). (d) CV graphs for the optimized electrode based on POT-MoS$_2$ (at a ratio of 1:4) in the presence of [Fe(CN)$_6$]$^{3-/4-}$. (e) Voltage measurements (OCP) for three electrodes, such as MoS$_2$-, POT-, and POT-MoS$_2$-based sensors, after coating with a nitrate ion-selective membrane in the presence of 1000 ppm NO$_3^-$—N. (f) Chronopotentiometry measurements for three nitrate sensors using POT, MoS$_2$, and POT-MoS$_2$ as the ion-to-electron transducing layers. Constant 50 nA anodic and cathodic currents were applied uninterruptedly for 60 s each, and the respective potential responses over time were recorded.

Figure 26:
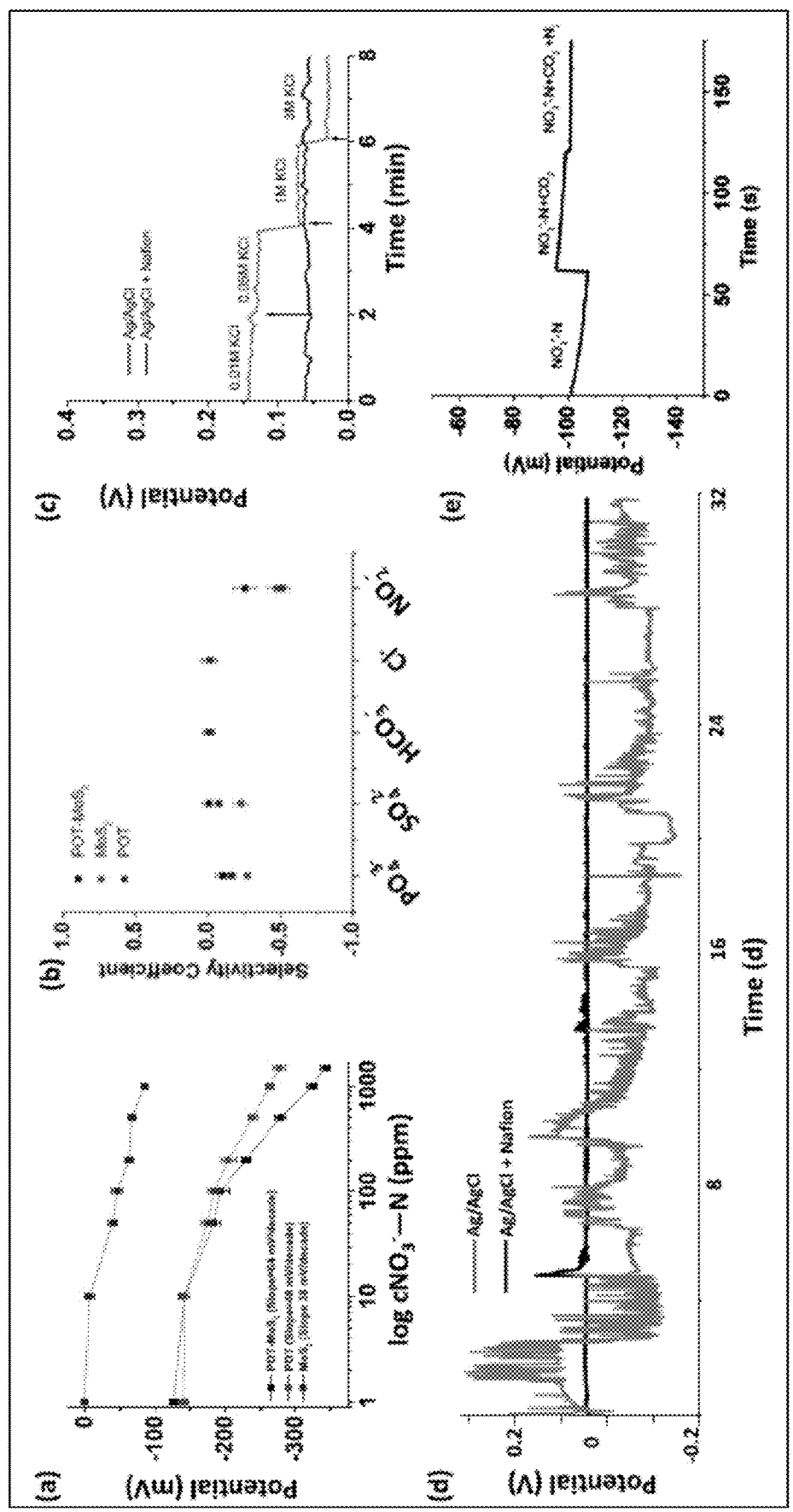

FIG. 26 relates to the Example 2 and is a (a) Sensor responses in millivolts (mV) made by MoS$_2$, POT, and POT-MoS$_2$ electrodes modified with ISM. A stock solution of 1500 ppm of nitrate-nitrogen was made in DI water and diluted from 1500 to 1 ppm. Sensor measurements were conducted for 2 min at each concentration. The corresponding average voltages for all the sensors (MoS$_2$, POT, and POT-MoS$_2$) were plotted against the logarithm of nitrate-nitrogen in ppm. Error bars were calculated using three consecutive measurements for each concentration. (b) For the selectivity studies, the NO$_3^-$—N concentration was set to 100 ppm, and the hydrophilic interfering ions were set to 400 ppm. The selectivity coefficients were calculated for MoS$_2$-, POT-, and POT-MoS$_2$-based ISM sensors using SSM. (c) Stability of the fabricated RE (Ag/AgCl) with and without Nafion coating was tested separately by varying the concentration of KCl from 0.01 to 3 M. For the stability test, the OCP of the fabricated RE was measured with respect to a leakless miniature Ag/AgCl RE having an internal electrolyte of 3.4 M KCl (obtained from EDAQ, ET072-1). (d) Long-term stability measurement of the Ag/AgCl electrodes with and without Nafion coating: plot of the OCP of the electrodes vs time in the presence of 0.01 M KCl solution. (e) Interference studies of the POT-MoS$_2$-based sensor in the presence of CO$_2$ and N$_2$ gases purging into a nitrate solution. After the nitrate measurement, the sensor was tested in a closed chamber where CO$_2$ and N$_2$ gases continuously flowed for 15 min before the measurement.

Figure 27:
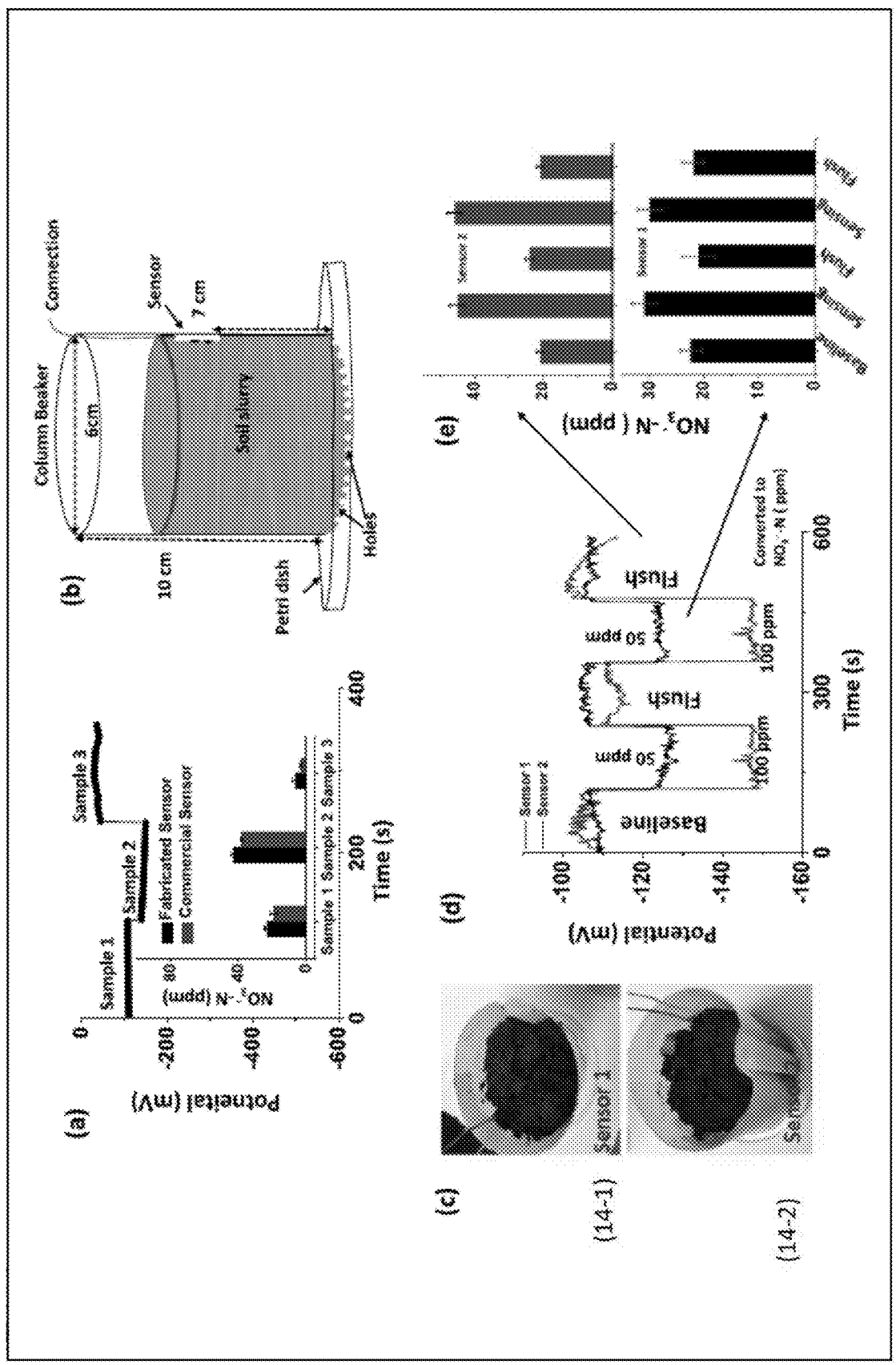

FIG. 27 relates to Example 2 and is: Graph (a) Sensor responses (commercial and fabricated) for real soil extracted solutions collected directly from Ames, Iowa, with a suction lysimeter. Graph (b) Schematic presentation of soil-column setup for nitrate-nitrogen measurement. Graph (c) Photographs of soil column beakers with soil slurries wherein the sensors were hung on the wall of the column. Graph (d) Short-term soil nitrate-nitrogen sensing in the soil column, where the baseline was set in the presence of DI water (baseline), and the column was flushed with DI water after the soil was treated with 100 and 50 ppm of NO$_3$—N, and Graph (e) plot for corresponding sensor readings.

Figure 28:
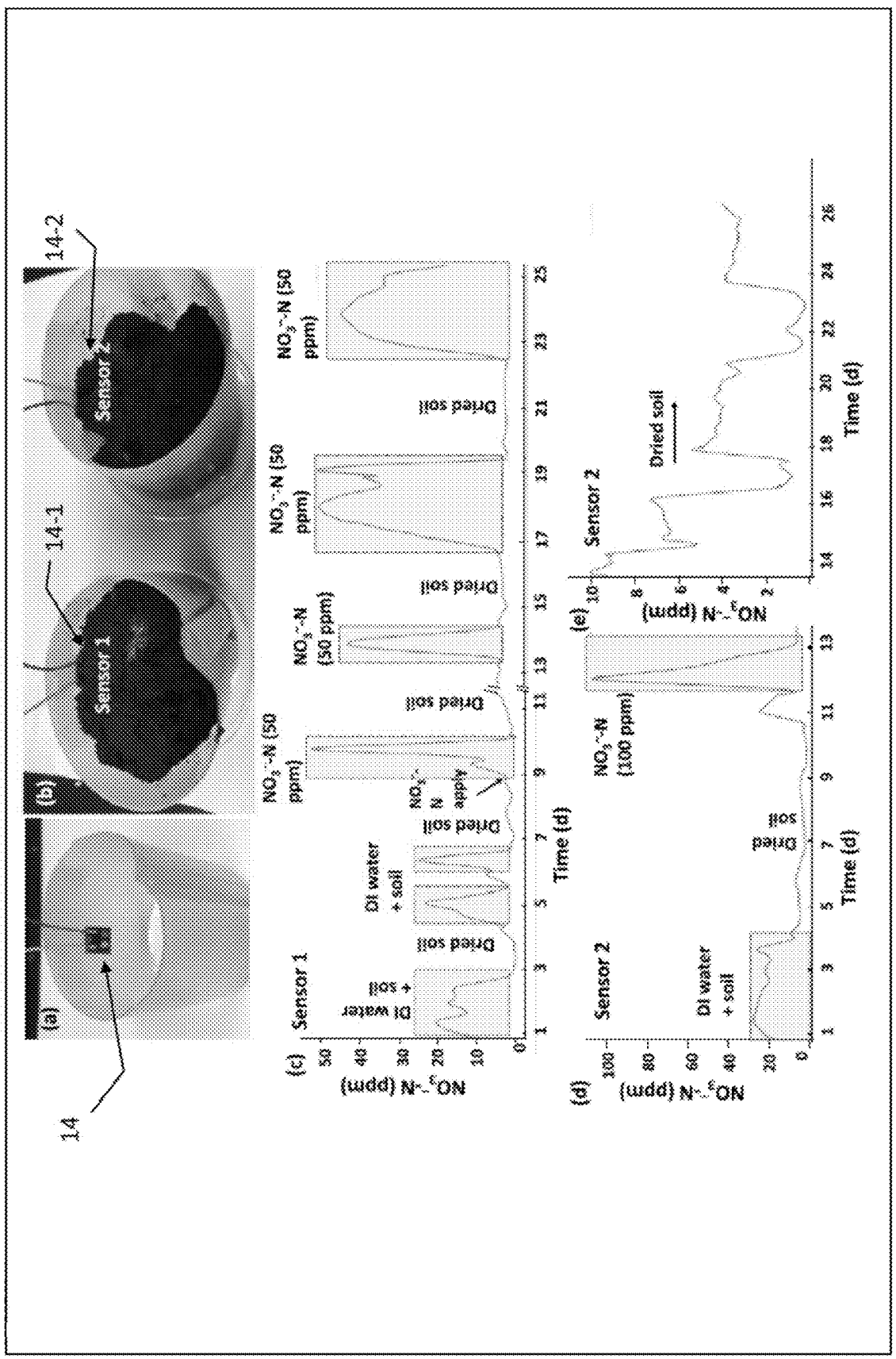

FIG. 28 relates to Example 2 and is a long-term measurements (approximately 4 weeks) using two different individual sensors (made with POT-MoS$_2$ material), wherein sensor 1 and sensor 2 were deployed in beakers containing soil slurries. Photographs of column beakers without soil slurries (a) and with soil slurries and sensors 1 and 2 (b). For sensor 1 (c), the soil beaker was filled with DI water and then left to dry, and the soil slurry was again treated with water multiple times and then parched. Finally, DI water mixed with nitrate-nitrogen (50 ppm) was poured into the soil slurry in the column beaker with sensor 1 and left to dry. The process was repeated multiple times (for approximately 4 weeks) for sensor 1. For sensor 2, the soil slurry was initially filled with DI water, parched, and flushed with 100 ppm nitrate-nitrogen (d). After drying, sensor 2 was kept in the parched condition for about 2 weeks (e).

Figure 29A:
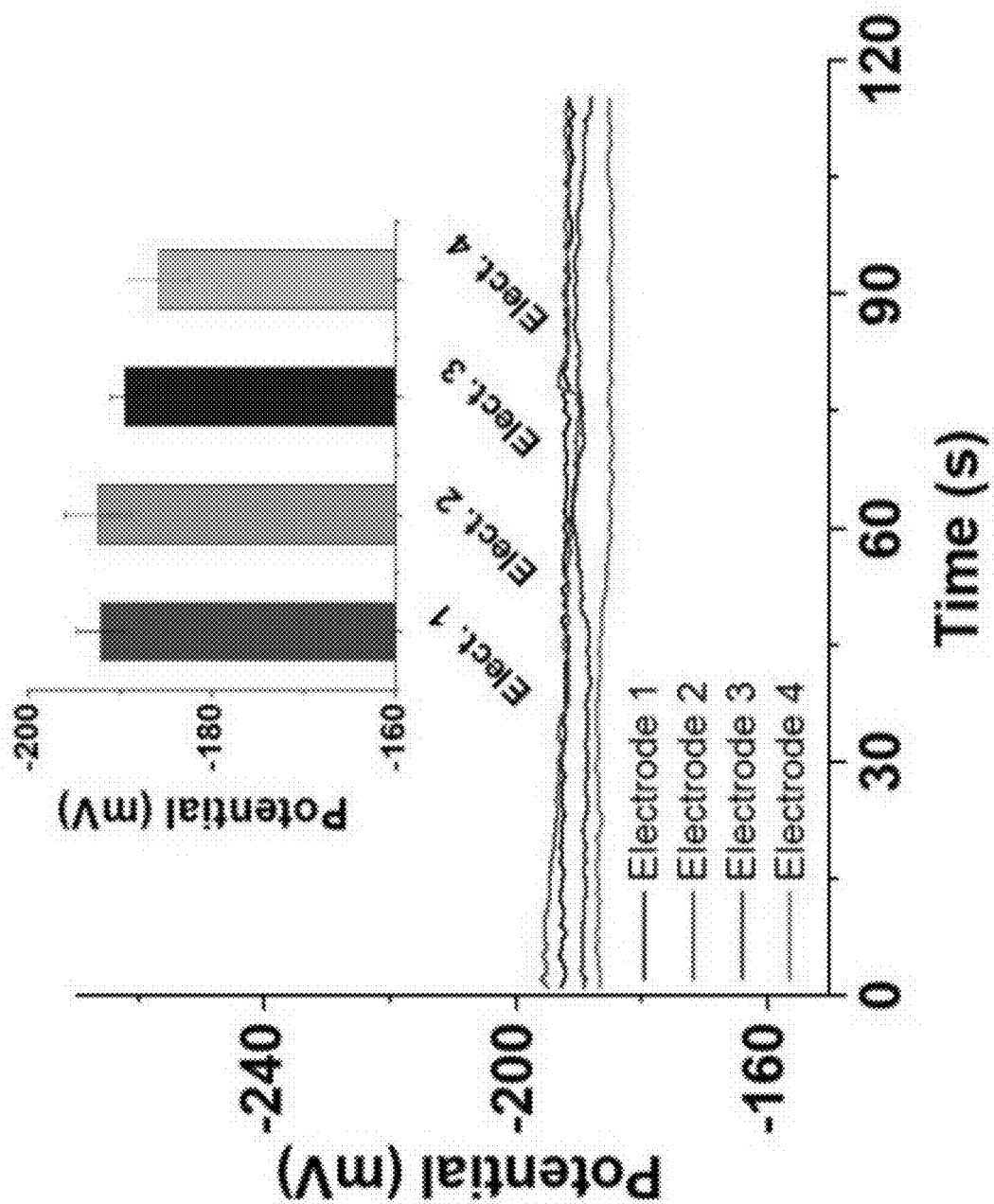

FIG. 29A relates to Example 2 and is a reproducibility studies for POT-MoS$_2$ based sensor with individual identical copies of the electrode.

Figure 29B:
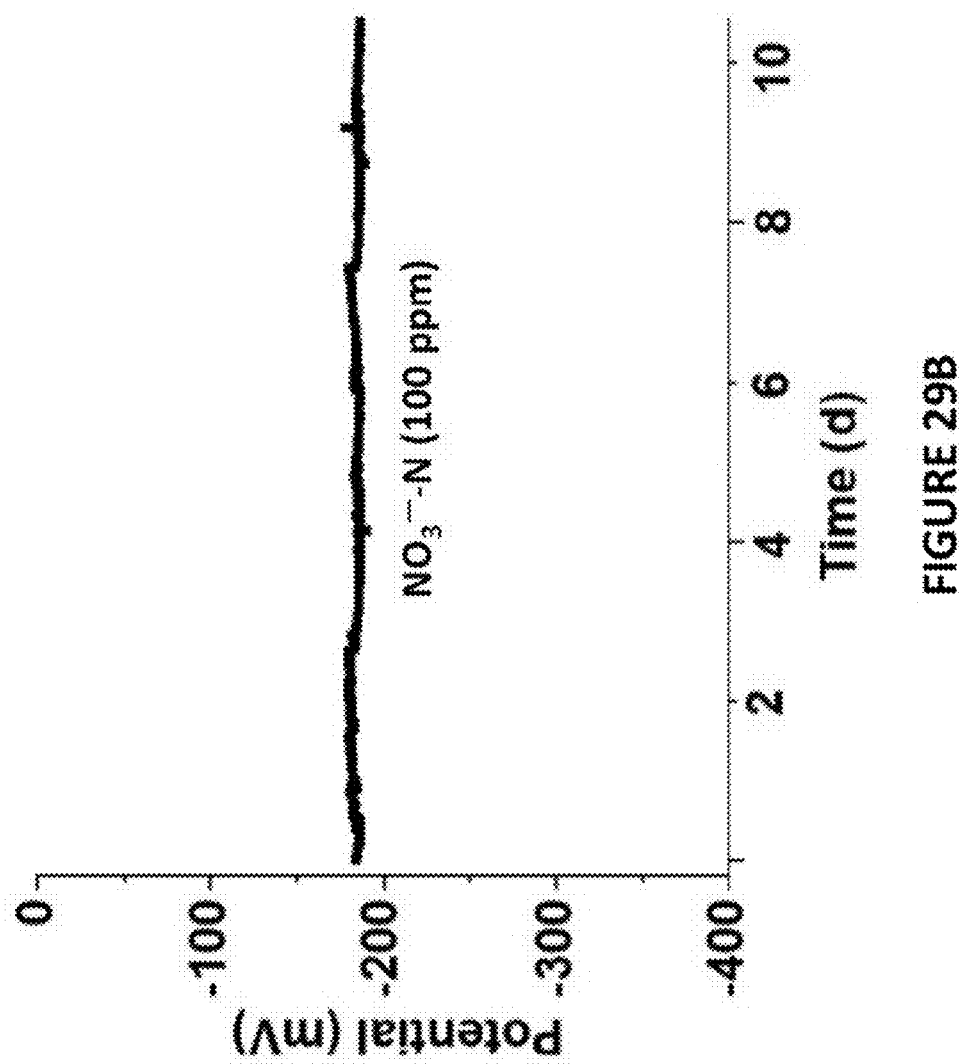

FIG. 29B relates to Example 2 and is the potential stability of the sensor (ISM/POT-MoS$_2$) for nitrate-nitrogen detection. In this measurement, the ISM/POT-MoS$_2$ electrode was conditioned for 3 d at high concentration of nitrate-nitrogen (1500 ppm) and inserted an open vial filled with 100 ppm of nitrate-nitrogen for long-term stability measurement. Results show the initial potential (starting potential ∼−184 mV) is almost matched after 10 days of potential measurement (end potential ∼−186 mV). However, it has been seen the there is a potential variation of 0.2 mV per day during continuous measurement.

Figure 29C:
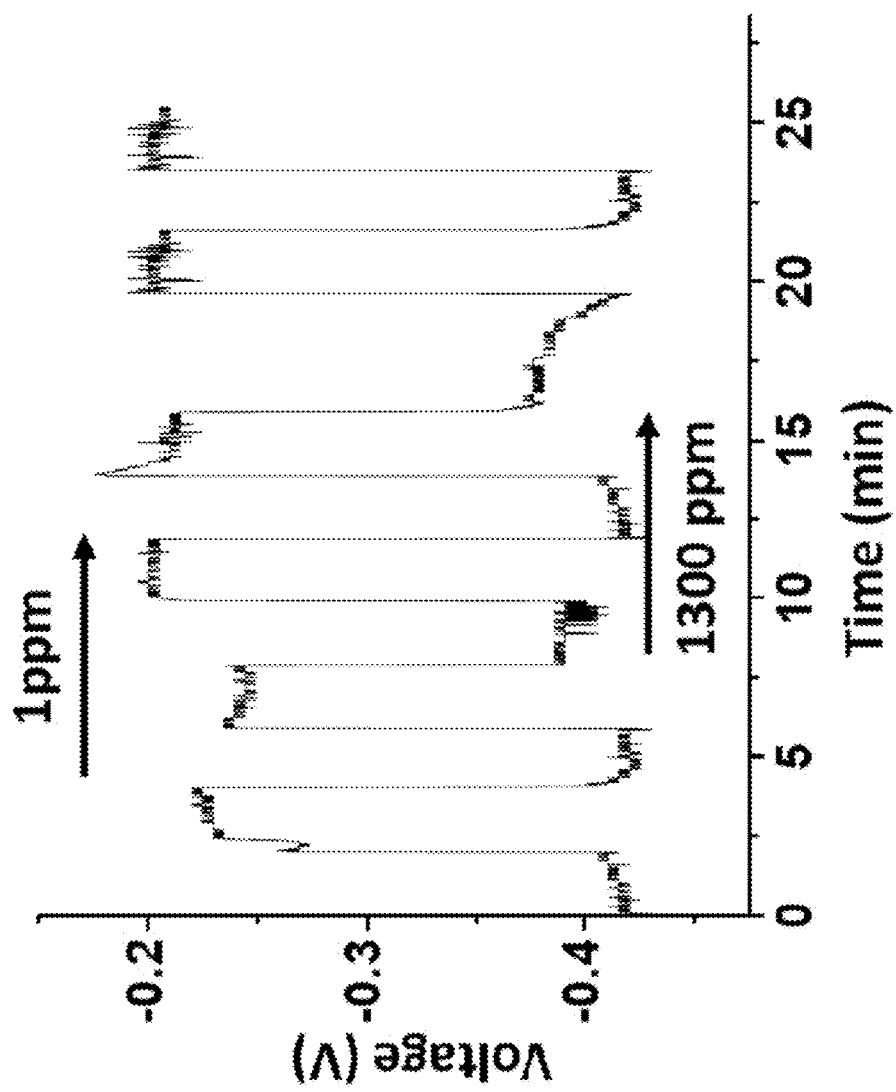

FIG. 29C relates to Example 2 and is an activity of high (1300 ppm) and low (1 ppm) concentration nitrate-nitrogen was performed to investigate the repeatability of the electrode.

FIGS. 30-35 relate to a Specific Example 3 according to aspects of the present invention.

Figure 30:
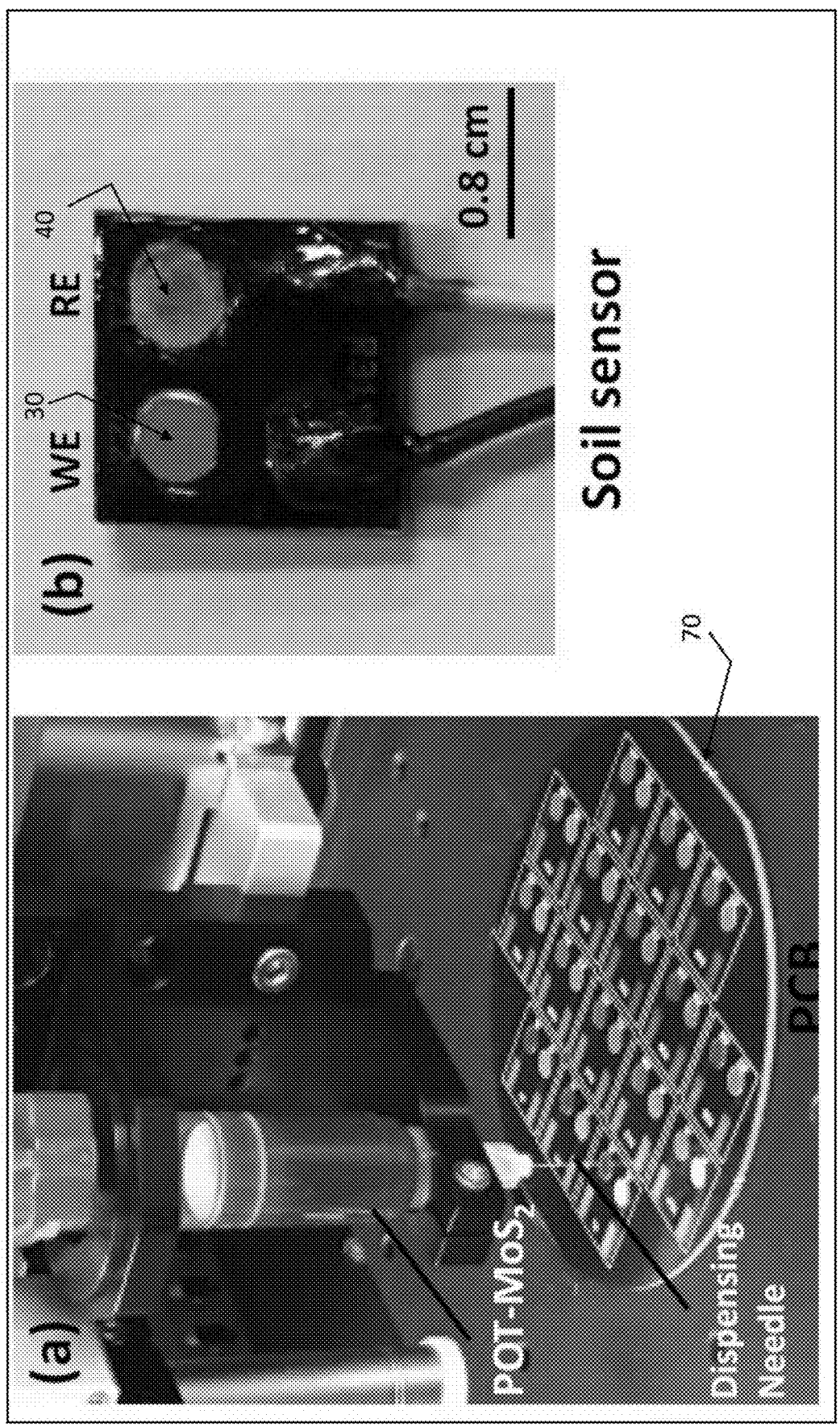

FIG. 30 is a diagrammatic view of an Example 3 according to the present Invention, including a method of manufacturing small-scale solid sensors according to aspects of the present Invention. FIG. 30 shows: (a) Coating POT-MoS$_2$ nanocomposite on the surface of substrate using a programmable robotic dispensing system. (b) Photo of a fabricated nitrate sensing unit.

Figure 31:
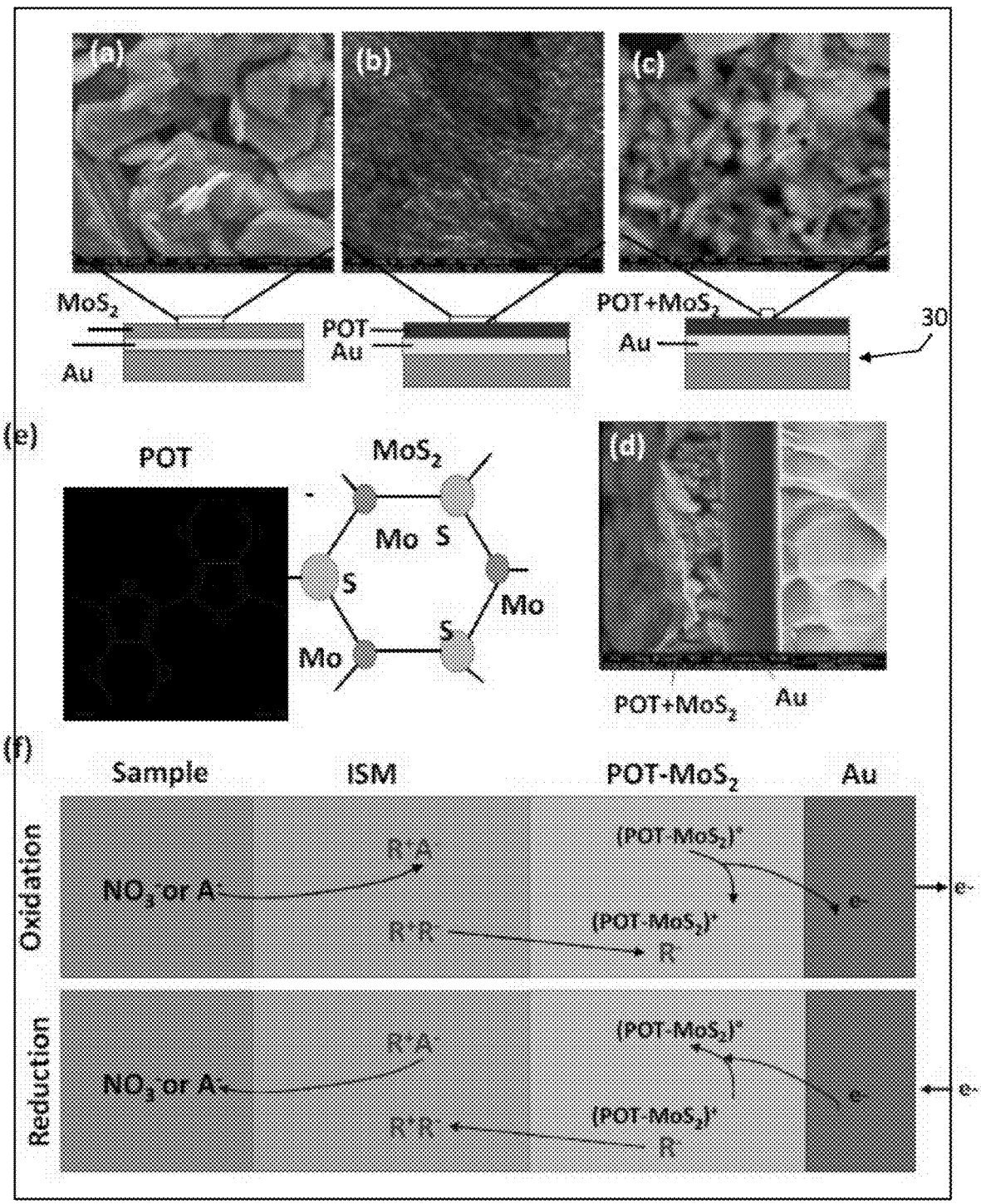

FIG. 31 relates to Example 3 and shows: SEM for MoS$_2$ sheets (a), POT (b), and POT-MoS$_2$ materials (c) with schematic of various layers. (d) A cross-sectional view of POT-MoS$_2$/Au. (e) Molecular structure of POT and MoS$_2$. (f) The oxidation and reduction for printed WE (ISM/POT-MoS$_2$/Au) in presence of soil NO$_3^-$ ions. R$^+$ and R$^-$ represent anion and cation exchangers at organic membrane, and A are hydrophilic ions.

Figure 32:
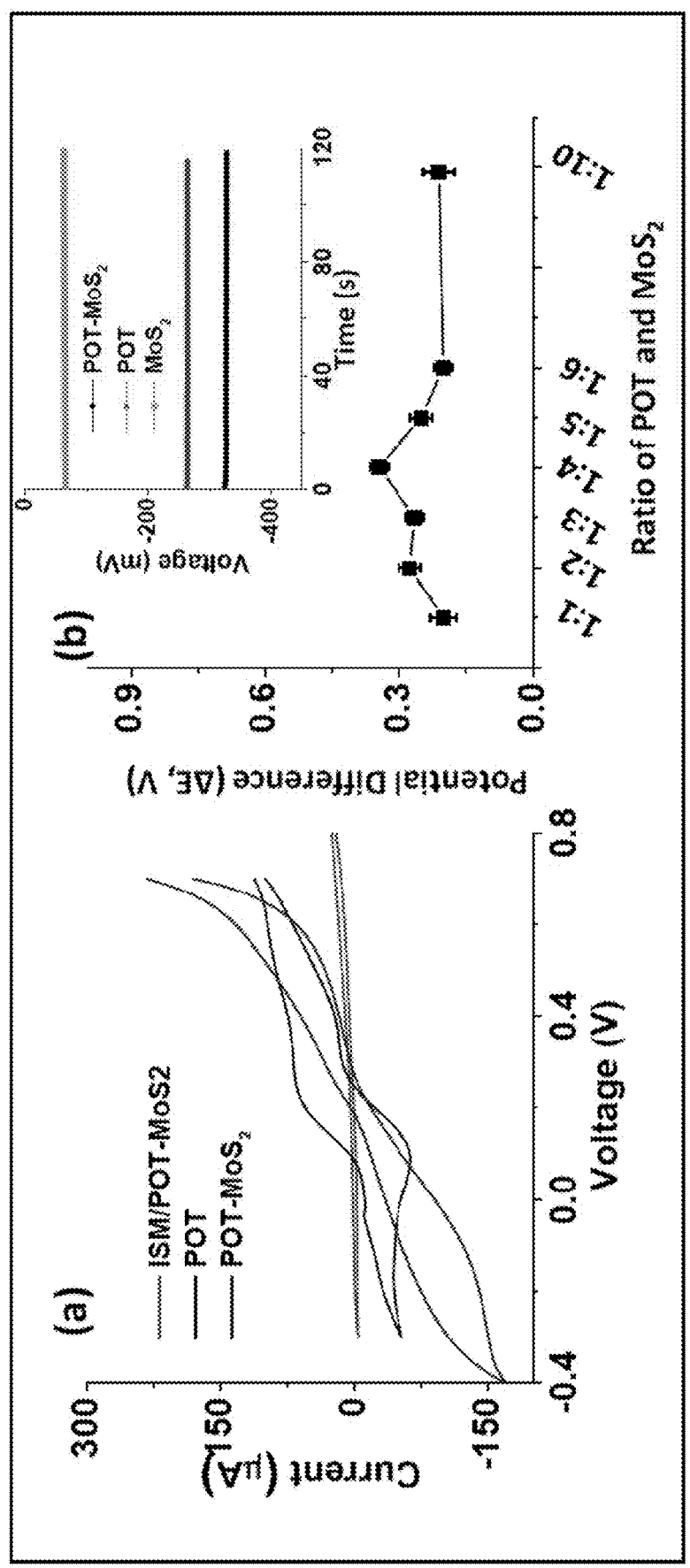

FIG. 32 relates to Example 3 and shows: (a) Cyclic voltagramms for various electrodes in presence of standard PBS solution. (b) Ratio optimization for POT and MoS$_2$. Inset shows the voltages of all three electrodes after coated with nitrate-selective membrane in presence of 1000 ppm NO$_3^-$—N.

Figure 33:
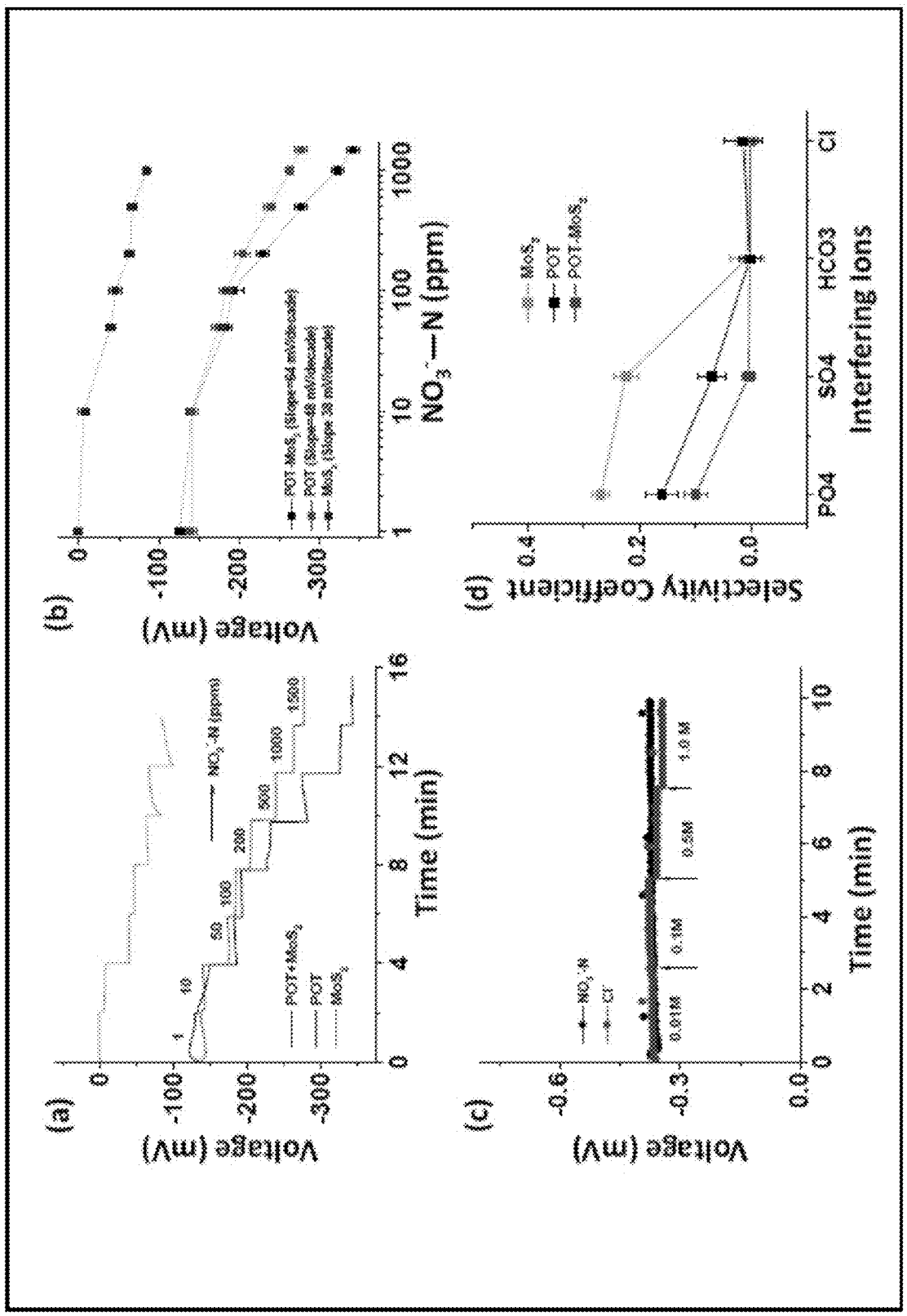

FIG. 33 relates to Example 4 and shows: Responses to varying nitrate concentrations of standard nitrate solutions for MoS$_2$-, POT- and POT-MoS$_2$-based sensors (a) and corresponding calibration curves (b). (c) Effect of Cl$^-$ ions on voltage output of the POT-MoS$_2$-based sensor. (d) Selectivity studies. The nitrate concentration was set to 100 ppm NO$_3^-$—N and the interfering ions were set to 400 ppm. The selectivity coefficients were calculated using separate solution method.

Figure 34:
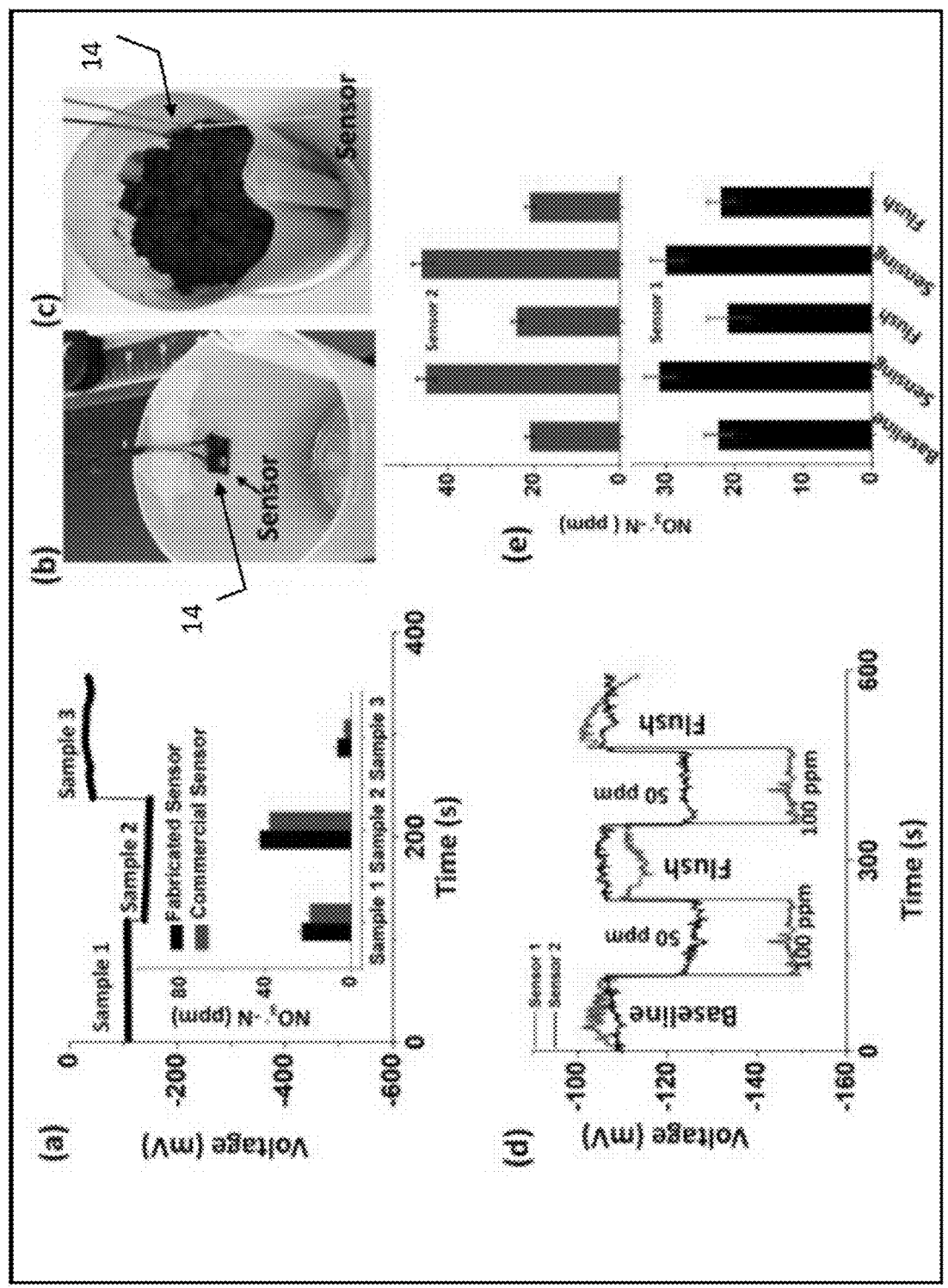

FIG. 34 relates to Example 3 and shows: (a) Nitrate sensing for extracted soil solutions and validated using a commercial sensor. (b-c) Experimental setup. (d) Short-term soil nitrogen sensing in the soil column, where the baseline was set in the presence of water (baseline), and the column was flushed with DI water after the soil was treated with 100 and 50 ppm of NO$_3^-$—N, and (e) Plot for corresponding sensor readings.

Figure 35:
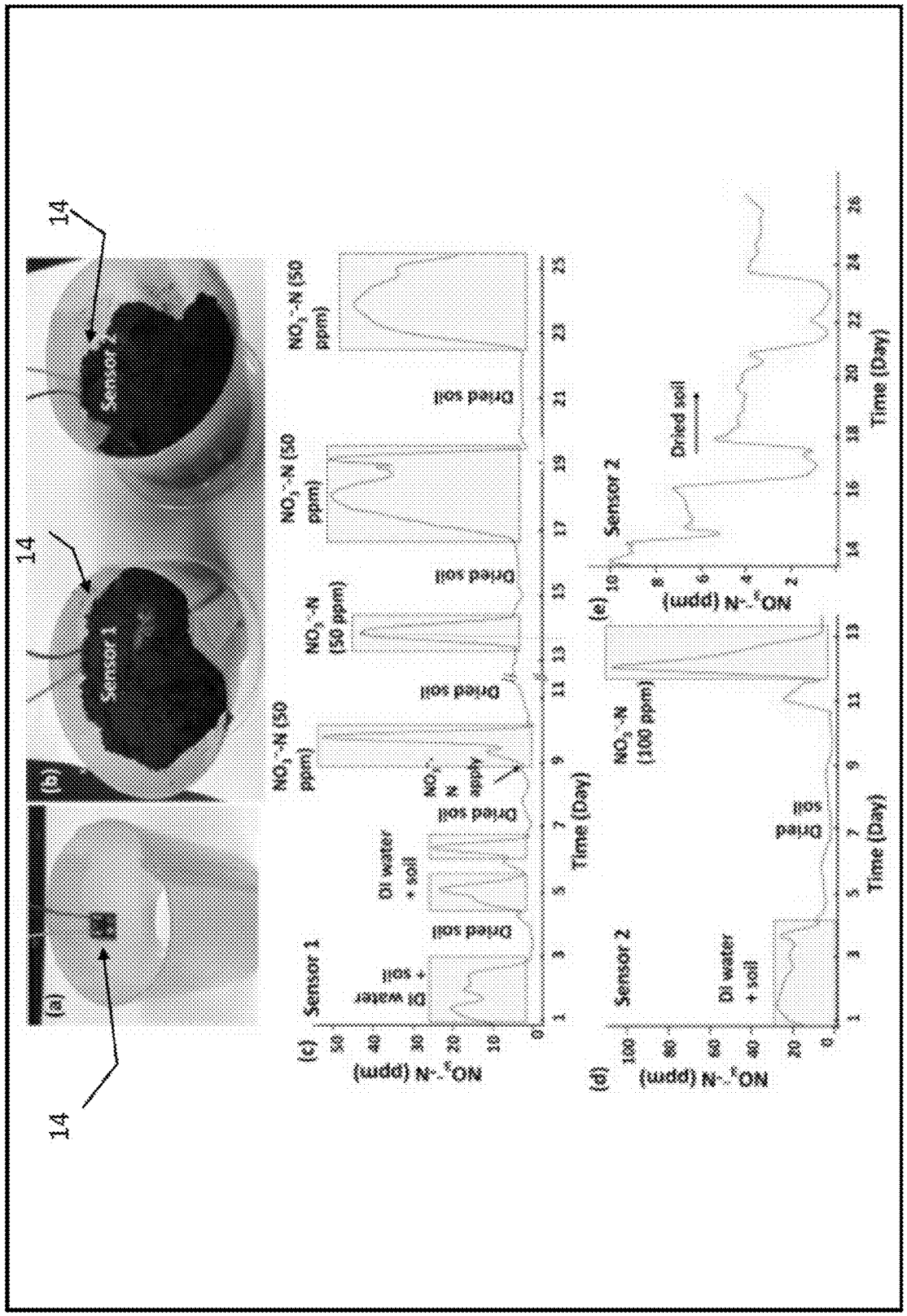

FIG. 35 relates to Example 3 and shows. Long-term measurement with two sensors. Photographs of column beakers without soil slurries (a), and with soil slurries and sensor 1 and sensor 2 (b). For sensor 1 (c), the soil beaker was filled with DI water and then left to dry, and the soil slurry was again treated with water multiple times and then parched. Finally, DI water mixed with nitrate-nitrogen (50 ppm) was poured into the soil slurry in the column beaker with sensor 1 and left to dry. The process was repeated multiple times (for approximately 4 weeks) for sensor 1. For sensor 2, the soil slurry was initially filled with DI water, parched, and flushed with 100 ppm nitrate-nitrogen (d). After drying, sensor 2 was kept in the parched condition for about 2 w (e).

IV. DETAILED DESCRIPTION OF EXEMPLARY EMBODIMENTS OF THE INVENTION

A. Overview

As will be appreciated by those skilled in the art, the invention can take many forms and embodiments. For a better understanding of the invention, examples of non-limiting specific embodiments will now be set forth. It is to be understood these are neither inclusive nor exclusive of all forms the invention can take.

As will be appreciated, the examples focus on in situ, long term detection of nutrients in soil and water in an agricultural field. A particular example is soil nitrate. As indicated, however, the invention is not limited to those specifics.

B. Apparatus/System

With reference to FIGS. 1-7, a first exemplary embodiment according to the invention will now be described. As will be appreciated with reference to the brief description of the appendices, background information on such things as how ion-selective detection works for soil nutrient measurement, how porous sampling heads can be used to collect a soil water sample, and how onboard, integrated fluid, electrical, and electronic subsystems can be powered by a battery and controlled by a processor are set forth. The main features and aspects of the invention will now be discussed.

The main features of the disclosed soil or water nutrient sensor system are as follows:

1. The disclosed sensor system 10 can automatically reset, recondition, and recalibrate for long-term, high-precision detection of nutrient in soil and water (e.g., tile drainage water) in crop fields (FIG. 1): Currently, there are several soil nutrient sensor technologies, including ion selective electrodes, ion selective field-effect transistors, enzyme-based electrochemical sensors, and electrochemical sensors. However, none of these sensors are able to automatically reset themselves after long term use. Manual reconditioning and recalibration are required for high-accuracy measurement over a period of time (e.g., >30 days). Therefore, existing nutrient sensors are usually used in laboratory. The disclosed sensor system is designed as a novel self-contained system to realize automated sampling, detection, reconditioning, and recalibration, without any manual interferences. A simple fluid manipulation unit (consisting of two normally-closed peristaltic actuators and a vacuum pump), in incorporation with a unique flow-through soil water suction head (see #3 below), allows sampling, conditioning and reconditioning, and calibration and recalibration, through manipulation of liquid fluids within the sensor system 10 (FIGS. 2A-C). The reconditioning liquids can be delivered to and from an embedded nutrient detection unit to wash the sensing surface and the interior of the sampling head.

2. A new ion-to-electron interface for ion-selective membrane to improve both sensitivity and selectivity of ion-selective membrane-based sensing unit used in the system: (1) The working electrode 30 of the sensing unit 10 contains an ion-to-electron transfer layer 34 between the ion-selective membrane 32 and the metallic (e.g., gold, Ag/AgCl) conducting layer 36. This ion-to-electron transfer layer 34 can be a nanocomposite of poly(3-octyl-thiophene) and molybdenum disulfide (or POT-$MoS_2$) that can improve sensitivity, selectivity and long-term stability of the sensor 14 (FIG. 3). The POT-$MoS_2$ is a first-ever nanocomposite introduced to the ion-selective membrane-based sensor and provides high redox activity and electron conduction ability to improve sensitivity, where POT helps increase redox activity and $MoS_2$ nanoflakes help increase electron conductance. Also, the incorporation of the POT-$MoS_2$ into the working electrode can minimize formation of a thin aqueous film between the ion-selective membrane and the metallic conducting layer. This can help increase selectivity and reduce signal drifting because the POT-$MoS_2$ exhibits a high lipophilicity inhibiting the formation of aqueous film that contains other interfering ions. Also, the aqueous film is a main source for substantial potential instabilities because the electrolyte composition of this layer may slowly change leading to drifting potentials. Therefore, minimizing or eliminating this aqueous layer using the POT-$MoS_2$ can reduce potential drifting at the working electrode, thus increasing stability of the sensing unit. (2) The sensing unit used in the disclosed sensor system 10 uses a novel integrated, low-cost, high-performance reference electrode 40, i.e., $S^3RE$ or sandwiched solid-state reference electrode. The $S^3RE$ 40 allows immobilizing a chloride reservoir on top of a base electrode 45 of Ag/AgCl to stabilize potential at the reference electrode 40. Generally, conventional ion-selective membrane based sensors use Ag/AgCl reference electrodes alone surrounded by high concentration $Cl^-$ ions with a porous glass/plastic frit tip. But, these simple reference electrodes undergo a redox reaction and leaching of chloride ions, which, in turn, alters the chloride equilibrium at the electrode surface, resulting in drifting of reference potential. On contrary, in the $S^3RE$ 40, a polymeric membrane 44 of polyvinyl butyral (PVB) contains a saturated concentration of chloride and a proton exchange membrane (PEM) 42 such as Nafion serves as a protection coating to minimize or even prevent leaching of chloride, thus stabilizing the reference potential of the sensing unit 10. See infra., and FIGS. 11 to 19 for more details. An appropriate voltage signal 50 is established between electrodes 30 and 40 during operation via an appropriate processor/control circuit/power source 18. Mounting surfaces or substrates 38 and 48, and waterproof mountings 39 and 49 can be used to support the metallic conducting layers 36 and 46, and other layers, respectively, on the substrates 38 and 48. Other techniques are possible.

Figure 4B:
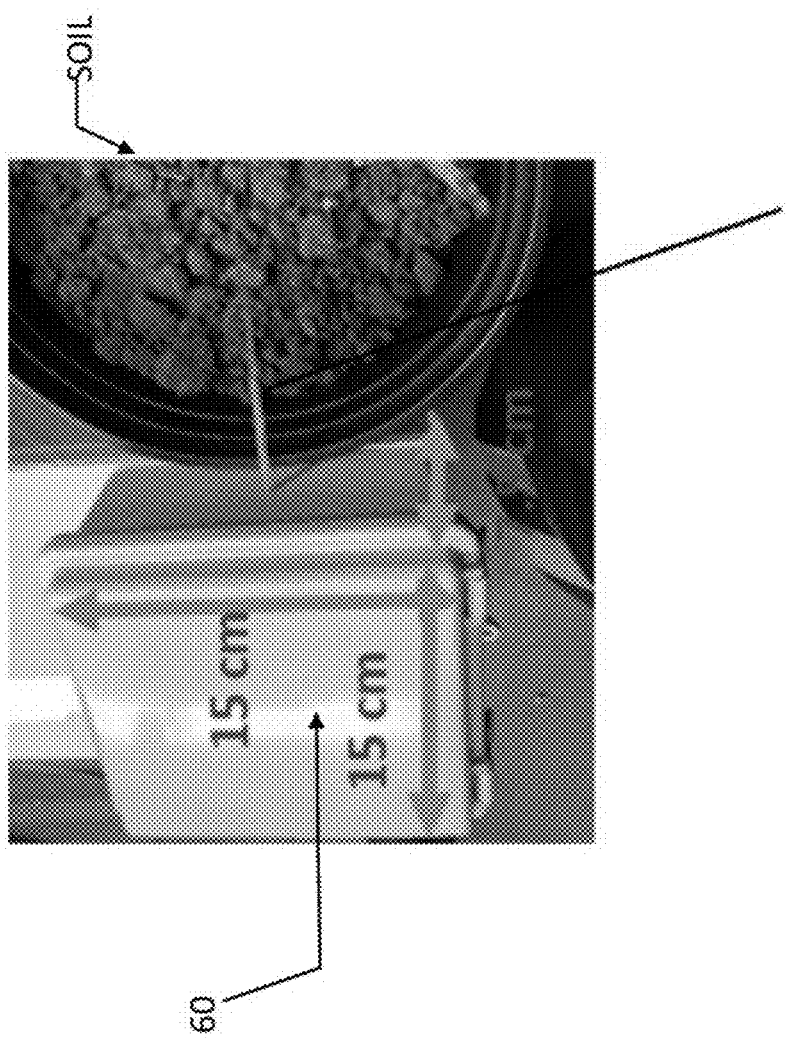
Figure 4C:
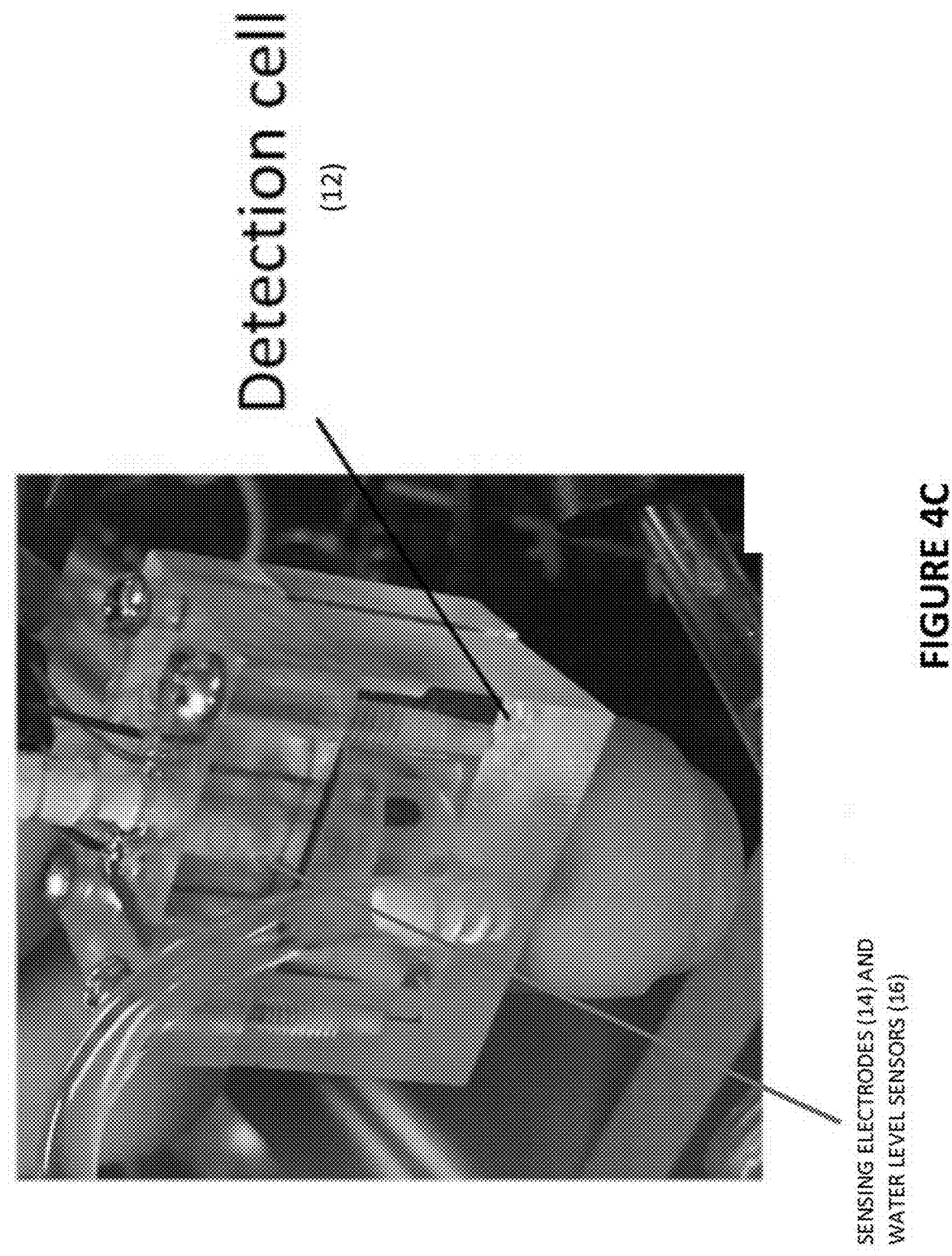
Figure 4D:
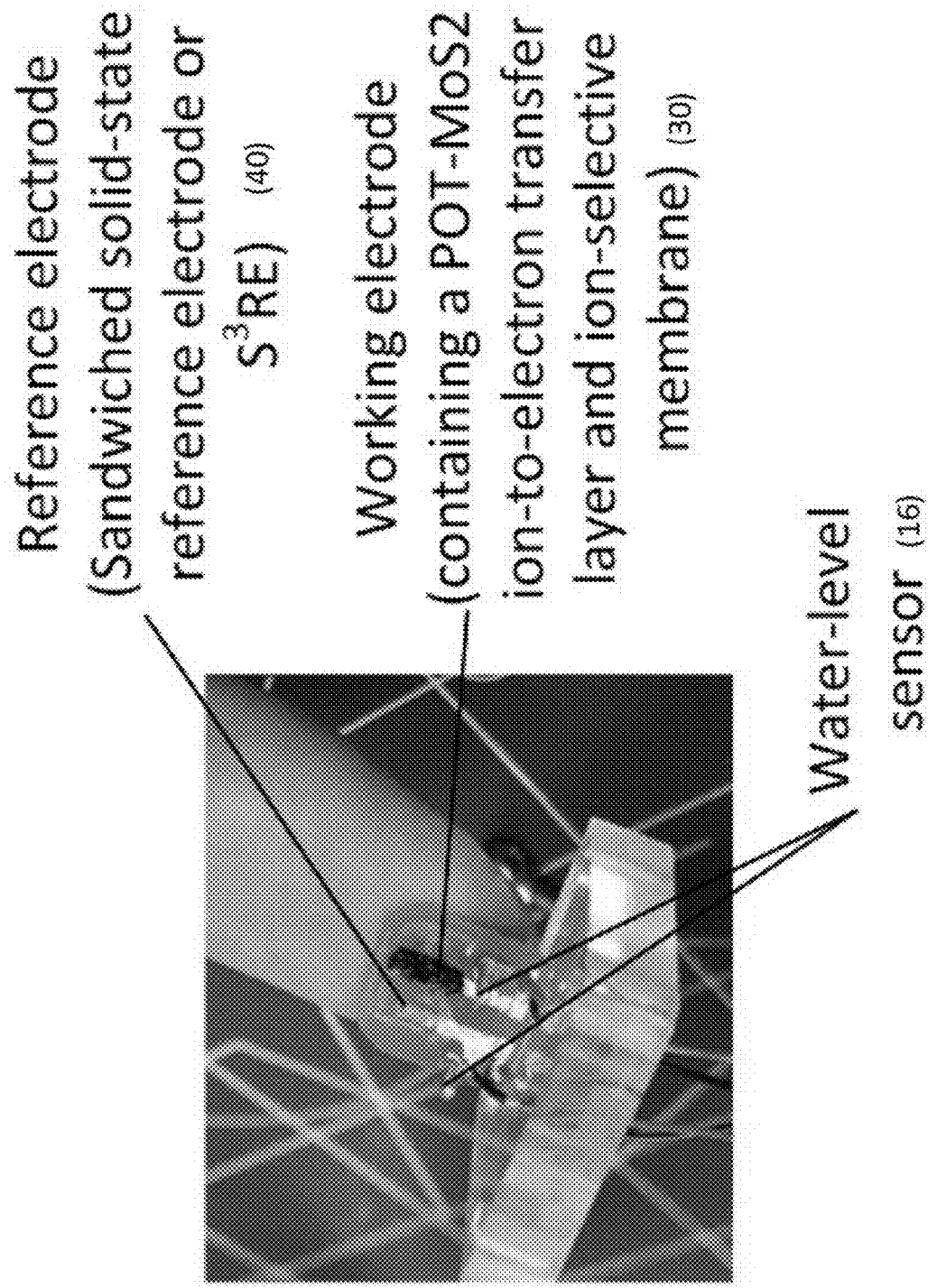
Figure 4E:
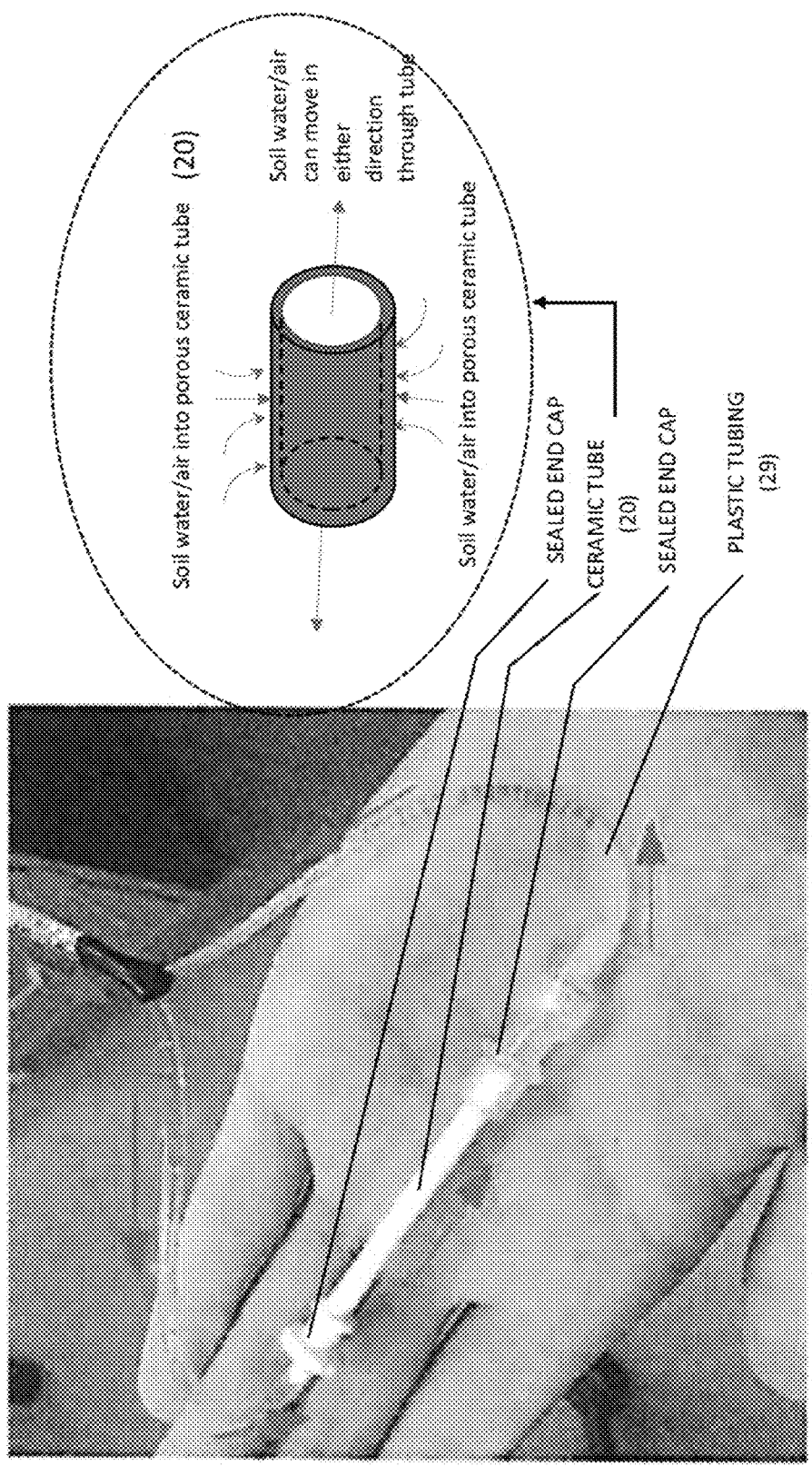

3. A flow-through soil water suction head: Ceramic porous capillary tubes have been widely used to extract soil water for analysis, and test soil water potentials for irrigation management. See, e.g., Di Bonito, Marcello, et al. "Overview of selected soil pore water extraction methods for the determination of potentially toxic elements in contaminated soils: operational and technical aspects." Environmental Geochemistry. 2008. 213-249, incorporated by reference herein. The disclosed water suction head 20 is unique in that it utilizes a porous ceramic tube with openings at both sides (see openings 21A and B). This design allows not only in situ sampling of soil water; but also in situ cleaning of the interior of the ceramic tube 20 by flowing a cleaning solution 27 from one side through the ceramic tube 20 into a waste reservoir 28 connecting on the other side of the tube 20 (FIG. 2 and FIG. 4E). This design also allows reconditioning and recalibration of the sensing unit 10 by flowing the calibration solutions to a detection cell 12. Therefore, after the soil water is sampled and analyzed, the suction head 20 can be easily washed and recalibrated in situ, without pulling it out of the soil. In contrast, a traditional soil water suction head has a closed end, making it difficult to clean the interior of the ceramic tube and to recalibrate the sensors.

4. Integration of a nutrient detection unit 14 and a water-level sensor 16 into a soil water collector or detection cell 12: The nutrient detection unit 14 is made inside or socketed into the soil water collector (or detection cell 12). A conductivity measurement unit 16 is designed to serve as a water-level sensor to control ON/OFF states of a vacuum pump 22. Soil water solutions cannot be extracted continuously; instead, they appear a mixture of tiny water droplets and air in the ceramic suction head 20. Vacuum pumping via tubing or conduit 23 directs the water droplet-air mixture along a plastic channel 29A into the detection cell 12 for analysis. The disclosed integration method reduces the amount of soil water required for analysis (e.g., less than 200 microliters).

5. In the disclosed sensor system 10, a single sensing unit 14 can be used for nutrient detection at least several dozens of times in the field. The sensing unit 14 is replaceable. Replacing is simple: simply sliding a new sensing unit 14 into the detection cell 12 (i.e., soil water collector). Without the disclosed fluid manipulation/control unit and the suction head with opening at two sides, the device 12 could work only for once in the field. The sensitivity, selectivity, and stability of the disclosed sensor 12 are increased (FIG. 5) due to the use of the improved sensing unit 14. See infra., and FIGS. 11 to 19 for more details.

C. Operation

Device Structure, Working Principle, and Operation

The disclosed sensor system 10 consists of three main units, i.e., (1) a special flow-through porous ceramic suction head 20 with openings 21 at both sides, (2) a vertically placed nutrient detection cell 12 embedded with an improved ion-selective membrane-based sensing unit 14 and a water-level detection unit 16, and (3) a novel fluid control unit with only two normally-closed peristaltic actuators (PeriA-3 and -4) and one vacuum pump (VacP). Also, please refer to the flow chart of FIG. 8.

Step 1: Initialization (FIG. 2A): PeriA_3 (ref. no. 24-3) and PeriA_4 (ref. no. 24-4) are turned ON. PeriA_1 (ref. no. 24-1), PeriA_2 (ref. no. 24-2) and VacP (ref. no. 22) are OFF. Liquids in the detection cell 12, plastic tubing 29A and 29B, and suction head 20 are pumped into the waste reservoir 28.

Step 2: Recalibration (FIG. 2B): PeriA_1 (ref no. 24-1) is turned ON. PeriA_2 (ref. no. 24-2), PeriA_3 (ref no. 24-3), PeriA_4 (ref no. 24-4) and VacP (ref. no. 22) are OFF. The standard calibration nitrate solution 26 is delivered through tubing 25 into the detection cell 12.

Step 3: When the standard calibration nitrate solution 26 reaches a preset volume (e.g., 200 microliters) in the detection cell 12, the water level sensor 16 is triggered to turn off the peristaltic actuators. Here, the water level sensor 16 is formed by two electrode elements. When the standard calibration nitrate solution (or extracted soil water solution) contacts the two electrode elements, the electrical impedance between the two electrode elements is changed, providing a signal to turn off the peristaltic actuators.

Step 4: The nutrient sensing element 14 in the detection cell 12 quantifies a specific ion species (e.g., nitrate).

Step 5: Cleaning (FIG. 2C): After the detection is done, PeriA_2 (ref. no. 24-2) and PeriA_4 (ref. no. 24-4) are turned ON to direct the standard calibration nitrate solution 26 from the detection cell 12 into the waste reservoir 28, and then flow the cleaning water from the water reservoir 27 through both the detection cell 12 and the suction head 20 into the waste reservoir 28. Flushing and cleaning by deionized water can reset and recondition the sensing element 14.

Step 6: Empty tubing: PeriA_3 (ref no. 24-3) and PeriA_4 (ref. no. 24-4) are turned ON, other peristaltic actuators 24-1 and 24-2 and vacuum pump 22 are OFF. Liquids in the detection cell 12, plastic tubing 29A and 29B, and suction head 20 are pumped into the waste reservoir 28. Here, liquid in the tubing 25 between the detection cell 12 and peristaltic actuators 24 must be pumped into the waste reservoir 28. Otherwise when the vacuum pump 22 is turned ON to extract the soil water, air dissolved in this liquid in the tubing 25 will expand on vacuum environment and push the liquid into the detection cell 12, dilutes the soil water and affects the soil water analyzing.

Step 7: Analyzing: All peristaltic actuators 24-1 to 24-4 are turned OFF. VacP 22 is turned ON. A mixture of soil water and air is sucked into the ceramic tube 20 through the pores embedded in the wall of the ceramic tube 20, and further, is driven into the vertically placed detection cell 12. Here, the uniqueness is that the use of the normally closed peristaltic actuators 24-3 and 24-4 eliminates the need of any valves (e.g., solenoid valves), to avoid directly pumping the cleaning (water or buffer solutions), standard nitrate solution and waste liquids from three reservoirs 26, 27, and 28 into the detection cell 12. This saves space and cost of the system (note: solenoid valves with sufficient holding pressure are costly and have large dimensions).

Step 8: When the soil water reaches a preset volume (e.g., 200 microliters) in the detection cell 12, the water level sensor 16 is triggered to turn off the vacuum pump 22 and start analyzing the soil water with the selective sensor 14 embedded in the detection cell 12.

Step 9: Cleaning: After the detection is done, PeriA_2 (ref. no. 24-2) and PeriA_4 (ref. no. 24-4) are turned ON, directing the tested soil water sample solution from the detection cell 12 into the waste reservoir 28, and flowing the washing water from the water reservoir 27 through both the detection cell 12 and the ceramic suction head 20 into the waste reservoir 28.

To conduct new measurements, go and repeat Step 1-9. FIG. 8 gives one non-limiting example of methodology 100 for these different stages/modes of operation possible with a unit 10.

D. Non-limiting Options and Alternatives

As mentioned earlier, the foregoing examples are not limiting to the invention. Variations obvious to those skilled in the art will be included.

For example, some of the Appendices mention different ion-selective membranes or detectors that can be configured for different ionic species and in different applications. See infra., and FIGS. 11 to 19 for a specific example.

A few other nonlimiting examples relevant to the foregoing are set forth below.

1. Integration

As indicated above, an overall system 10 can be created which includes or integrates one or more of the features and aspects of the invention described herein. It can be an all-in-one system, including a housing, power source, detection cell (e.g. electrodes and membrane), a sampling suction head (e.g. flow through) and built-in water level sensing; refresh/flushing operation, fluid manipulation components and reservoir, data storage, a readout, and a data interface (e.g. communication including wireless). This description includes other non-limiting options and alternatives.

FIGS. 1-8 and 10 illustrate an all-in-one unit 10 including a ruggedized (e.g. metal or plastic) housing 60 with internal onboard power supply 66. Subsystems allow collection of soil water and then transport over a variable length fluid conduit to the housing 60 and a detector cell 12 in the housing. A miniaturized or micronized electrode based detection cell 12 can sense when enough soil water sample is present and then conduct the electrochemical sensing to measure a chemical species of interest related to the selected ion-selective membrane used. In this first measurement cycle state, the integrated system can derive from the electrodes electrical measurements that are converted to data that can be processed and stored as a measurement of interest. The onboard battery 66 can supply needed electrical power for these functions to both electrical and electronic systems as well as actuators 24 for fluid manipulation unit 64 and reservoirs 62.

In a second state, electrical power managed by the processor 68 can control fluid manipulation components 64 for a flushing of the system to recondition it in preparation for a next sampling and detection cycle. The onboard system can include other components such as data storage 69 and a readout circuit associated with processor 68. There can be data ports or interfaces for downloading data to another device. As indicated in certain Appendices, an option would be to include electrical communication whether wired or wireless. See, e.g., FIG. 9.

FIG. 10 illustrates a variation on an all-in-one cell 12 with sensor unit 14 and water level sensor 16. Multiple suction heads 10-2, 20-2, to 20-n could be used with one cell 12. By programming and control of actuation, all sampling heads could simultaneously by suction retrieve soil water samples for collective chemical sensing in cell 12. A read-out based on the collective samplings could be used. Alternatively, by appropriate set-up and control, sampling could be done seriatim one sampling head 20 at a time and measurements made and stored/communicated. Still further, each cell 12 could have one sensor unit 14 for all heads 20, or one unit 14 for each head 20, or other arrangements. Still further, tubing to each head 20 can vary in length or be selected in length allowing each head 20 to be placed to different sub-soil depths or different locations relative to cell 12. This can allow either a collective average measurement if all samples are collectively retrieved and one measurement taken, or individual measurements made for each head to gain information about variation of the measurement per head location.

2. Form Factor

The integrated example is at centimeter scale or less. One example as indicated at FIG. 4B is a housing 15×15×7.5 cm with an approximate 8 cm long by 2 cm outside diameter ceramic porous tube 20 as the sampling head. Tubing to the sampling head can be selected based on the ability to place the housing at ground level and extend the sampling head into the ground around it to various steps. References cited in the Background section above suggest sampling depths from 6 to 60 cm might be of interest.

That general form factor is not materially disruptive to planting and other field events. If desired, the housing could be buried to further protect it. Some sort of GPS waypoint or physical visible aboveground indication might be used to locate and remove it if buried. The system can be ruggedized and sealed.

3. Power

Electrical connections can be conventional. Some are indicated in the figures.

4. Fluid Manipulation

FIGS. 1-8 and 10 show a vacuum pump 22 as the primary fluid manipulation source for state one of the system 10. Such a vacuum pump can be small and inside the housing 60 and provide sufficient pressure difference to effectively collect soil water at the sampling head 20 and move it to the detection cell 12 repeated times over a battery life for the system. An example of such a pump 22 is model number D2028 from vendor Karlsson Robotics, FL, USA. Alternatives are, of course, possible.

State two system flushing is shown using peristaltic type pumps 24 and fluid conduits between cleaning liquid reservoirs 27 and waste reservoirs 28. Examples are model 1150 from vendor ZJchao Inc., China. They too could operate over repeated flushing cycles for the intended normal operating life of the battery and system.

As can be appreciated, water level sensors in the detection cell can stop fluid accumulation above the sensed maximum level. This can avoid having to use valves or fluid gates which could have actuators and use additional power and resources.

Similarly, the peristaltic actuators function both as a pump and as a check valve.

5. Suction Head

One suction head 20 is shown in most of the systems in the drawings. As indicated at FIG. 10, it can be possible to attach multiple heads 20-1, 20-2, 20-n to a single detection cell 12. Other variations are indicated.

It is to be appreciated that the relatively small form factor ceramic tube 20 in the drawings could be placed at various depths in the soil for different data acquisitions based on depth. Different lengths can be used/selected to sample to different soil water depths in the Z-direction relative to the ground.

Measurements from different spatial locations, depths at or near the same spatial location, or otherwise from different detections can be acquired and compared. Measurements can be compared for differences.

One example of a sampling head is a ceramic tube having open ends. Permeability can be selected by the designer according to need or desire. Other porous tubular structures are possible. Non-limiting examples are plastic or metallic tubing with selected permeability.

Similarly, the fluid conduits connecting the head to the detection cell, the vacuum pump to the detection cell, and the reservoirs to other components can be plastic of a substantially robust grade for the environmental extremes of an agricultural field over various seasons of the year. Other non-limiting examples are possible.

6. Water Level

FIGS. 1 and 2 show a water level sensor 16 at each electrode of the electrode-based ion-selective detector 14. In this non-limiting example, use of two sensors 16 can detect/determine water level by the following technique: impedance measurement.

7. Electrochem Detection

Both types of detector 14 and parameters related to the novel ion-to-electron transfer layer 34 at the working electrode 30 and the novel sandwiched solid-state reference electrode 40 are set forth above. Variations obvious to those skilled in the art are included.

Non-limiting examples of alternatives are: ion selective field-effect transistor-based sensors (e.g. extended gate), enzymatic electrochemical sensors, optical chemical sensors, microwave based chemical sensors.

Alternatives to POT and Nafion have been mentioned elsewhere.

8. Flushing Subsystem

The flushing subsystem not only can move out of the detection cell 12 any fluid as well as out of the sampling head 20, variations as to the type of fluid that can be inserted into the system are possible. Additionally, the flushing system might be activated to try to unplug a blocked conduit or blocked suction head. The vacuum pump 22 could be operated for that purpose also. Both the vacuum and the peristaltic pumps could be operated in a toggling mode for such purpose.

Essentially the flushing can be artificial rain to rinse soil water for the next measurement. The unit can be cycled by vacuum if not working to try to unplug it.

9. Applications

A few non-limiting examples of applications and variations of the system are set forth above. Variations obvious to those skilled in the art will be included. Some additional examples are: monitoring of nutrient in water (e.g., agricultural subsurface water, drainage water, sewage pipe water).

A primary use is as in situ soil nutrient sensors (e.g. housed on the ground or at ground level with sampling head 20 buried to a desired depth or depth(s)). Other non-limiting examples are indicated herein.

10. Distributed System with Multiple Detectors in Field and Optional Communication Capability to Remote Sites.

With reference to FIG. 9, as will be appreciated by those skilled in this technical area, the following types of variations and options with the system of FIGS. 1-8 are possible.

Multiple Spatially-distributed Sensors. A plurality of sensor systems 10-1, 10-2, 10-3, 10-$n$ as in FIGS. 1-8 (particularly FIG. 6) could be placed at spaced apart positions, individually monitor and take measurements at its position over time, and store or communicate those measurements for further use. They could be in the same or separate crop fields. They could be relatively closely spaced or more widely spaced. They could be individually readable at selected times or collectively report each of their readings. The designer could select these and other parameters based on need or desire, as well as practicality. A benefit of this arrangement is that each sensor 10 is relatively inexpensive to make and operate, and could generate measurements over extended periods of time. This allows collection of a lot of data specific to each sensor location over an extended time in situ and without disruption of normal agricultural activities in the field. But it also allows collection of data from multiple sensors 10 for collective analysis. Such collective analysis can be used in a number of advantageous ways by agricultural producers, as is well-known. To have not only data resolved to individual spatial locations, but also over relatively long periods of time can lead to insights that can be very helpful to the producers.

As indicated in FIG. 9, one way to communicate results automatically or semi-automatically is via wireless communications from each sensor unit 10. Of course, other ways of data collection for each is possible, including but not limited to a reader that can be moved across the field and wirelessly interrogate stored measurement data from each sensor. Still further, a hard-wire connection could be made to each sensor unit 10 to read the data. But with current Blue-tooth and other wireless relatively low power reading techniques, a worker could walk or move by in a vehicle each of the sensor units 10-1 to 10-$n$ and get wireless data transfer of measurements.

One or More Sensor Cells at Each Spatial Location. As indicated in the enlarged diagram at the lower left hand of FIG. 9, another optional feature is that there could be either a single sensing head 20 or cell 12 embedded into soil or water at a pre-selected depth and in electrical communication (e.g. via hardwire or possible wireless) with a separated Readout Circuit/Timing Control/Data Storage/Power Supply (or collectively Control Circuit 18) as indicated diagrammatically in FIG. 1. This could allow the Control Circuit 18 to be placed above-ground level or above water level with the sensor cell 12 or sampling head 20 at a selected depth in the soil or water. This can allow for easy access for, inter alia, maintenance, repair, programming, battery replacement, and the like. It would also allow, if desired, recovery and reuse. The form factor of such Control Circuits 18 can be relatively small, robust, and low profile so as to not disrupt plant growth or vehicle travel by or even over them. However, it is to be understood that any housing and components of the Control Circuit 18 could be made to allow it also to be embedded into the soil or water and operate from that position, if desired or needed. As mentioned, wireless technologies like Bluetooth allow wireless reading of embedded Control Circuits at least if sufficiently close in distance.

But there could be multiple such heads 20 and/or cells 12 for each Control Circuit 18 (see ref. nos. 12-1, 12-2, to 12-$n$ and 20-1, 20-2, to 20-$n$ in FIG. 9, lower left hand enlargement). This could, for example, allow measurements at the same geospatial location from plural depths. Each sensor cell/sampling head combination 12/20 could report this information and allow further differentiated analysis of measurements from such different depths, for a single Control Circuit 18.

Communication Options. As further indicated diagrammatically in FIG. 9, by techniques and components well-known to those of skill in this technical area, collection of data from each measurement cell can be individually, but also collectively. In one non-limiting example, all cells and Control Circuits in a field could wirelessly communicate to a wireless collection point within wireless communication range of each Control Circuit. In one example it could be within perhaps tens to hundreds of feet to each collection tower. The collection tower (labelled wireless hub in FIG. 9) could then have components with sufficient power and capabilities to communication wireless or otherwise to a LAN, WAN, or the Internet. By appropriate software, the measurement data from all the sensor cells can be collected, with registration to the geospatial position of each cell, and communicated from further use. Examples are to cloud storage for later access and use by any of remote computers, servers, or databases, or access and use by any of a number of digital devices (e.g. smart phones, tablets, lap tops, desk tops, etc.)

This collection of big data can be from a single field for use by a landowner/producer. But it could be from multiple fields, multiple farms, multiple landowners/producers, multiple counties, states, and even countries. Having this big data can lead to understandings or insights that can be helpful to not only individual producers but researchers, scientists, governments, seed companies, and others.

E. Specific Example 1 of Solid State Nutrient Sensor

With particular reference to FIGS. 10-19, details about a specific solid-state sensor configuration useable according to aspects of the invention are as follows.

All-Solid-State Nutrient Sensors Using Printed Polymeric Composite of POT-MoS$_2$ as an Ion-to-Electron Transfer Layer and Sandwiched Solid-State Reference Electrode (S$^3$RE) for Detection of Nitrate in Soil and Water Unlike conventional ion-sensitive sensor, the main motivation was to construct a novel, deployable, miniature, mass production and stable all-solid state nitrate sensor. Selection of appropriate materials is crucial for the better performance of the sensor. The potential issues with conventional ion selective devices are signal drifting, instability, bulky and not miniaturize. The internal filling solutions (such as nitrate for nitrate selective sensor) is commonly used for the development of ion selective sensors. Our approach was to replace the internal filling solution by introducing an ion-to-electron transfer layer in between ion selective membrane (ISM) and conductive layer and reducing potential drift at output signal. The potential drift occurred not only in the working electrode but also happened in the reference electrode of the device. For working electrode issues, we introduced a composite material of poly(3-octyl-thiophene) and molybdenum disulfide (POT-MoS$_2$) as ion-to-electron transfer layer. POT-MoS$_2$ material can also replace the internal nitrate solution between the conductive electrode and ISM. The POT is an attractive material for the construction of all-solid-state ion selective sensors due to their high redox property and prevent the formation of water layer due to its high lipophilicity. However, the POT is found to be not significantly conductive material, thus we introduced MoS$_2$ into POT polymer to enhance the device performance. The incorporation of MoS$_2$ can increase the redox property, amplify the voltage signal, lowering the limit of detection and reduced the potential drift of the sensor. For the all-solid-state Ag/AgCl reference electrode (RE), there are several issues such as constant supply of Cl— ions to compensate Cl— equilibrium in the redox reaction of Ag/AgCl surface, sensitive to Cl— and other ions and potential drift over time. A three layered sandwiched type solid-state structure can be a potential solution by reducing the chloride leaching over time, holding the chloride ions in a polymeric membrane and blocking other ions. The polymeric membrane of polyvinyl butyral (PVB) can hold KCl crystal on Ag/AgCl layer to supply Cl— ions constantly due to its nanoporous feature. A proton exchange membrane such as Nafion can block the leaching of Cl— from the RE surface and block the other interfering ions.

Our work is to make portable and miniaturize nitrate sensor, we have constructed both electrodes by using silicon needle via microfabrication technique and coated these materials using liquid auto-dispensing unit for mass fabrication. Combining both solid-state electrodes containing all the materials on the surface of Si needle, the needles were placed in 3D printed case as silicon needles are fragile. Affordability, portability, all-solid-state electrode with ion-to-electron transducer and mass fabrication are the attractive features of this nitrate sensor. The fabrication process is shown in FIG. 11.

A main feature of the reference electrode is to make a sandwiched solid-state reference electrode (S$^3$RE) to provide a stable voltage for both long and long term measurements (FIG. 12c). The Ag/AgCl RE electrode 40 surface undergoes redox reactions and leaching of chloride ions (Cl$^-$) which alters the chloride equilibrium resulting in voltage drifting chloride equilibrium. To compensate Cl$^-$ ions for the redox reactions and to isolate the electrode 40 from other interfering ions, we introduced a low-cost and rugged polymeric material 44 (polyvinyl butyral or PVB) with pore size ranging from 50-200 nm. PVB can hold Cl$^-$ ions in its membrane form and supply Cl$^-$ ions when needed. Unlike the conventional RE which contains a reference internal solution of KCl (3M) separated with Ag/AgCl wire, the S$^3$RE electrode 40 is free from internal reference solution by replacing solid-state membrane with solid KCl crystals in order miniaturize the sensor system.

The S$^3$RE was made on a silicon with grown oxide (FIG. 12c). The S$^3$RE has three layers such as Ag/AgCl, PVB and Nafion. The 1 µm thick of silver was deposited on Si/SiO$_2$ needle and further treated with FeCl$_3$ (0.1M) plus HCl (0.001 mM) solution for 30 s to form Ag/AgCl on Ag/SiO$_2$/Si surface and then dried at 100° C. for 2 hr. The formation of Ag/AgCl is shows in FIG. 12a. The formation of Ag/AgCl layer (first layer) provides a constant half-cell potential by enabling a reverse-redox reaction in the nitrate sensor device. Another polymeric layer (thickness: 1.7 µm) made of polyvinyl butyral (PVB) containing KCl was deposited on the surface of AgCl layer (second layer). FIG. 12b shows a cross-sectional scanning electron microscopic image for the formation of S$^3$RE. To prepare this PVB solution, 395 mg of PVB and 250 mg of KCl salt were dissolved in 5 mL in tetrahydrofuran solvent (THF) or methanol and sonicated for 24 hrs and then deposited using a liquid auto-dispenser. The PVB stock solution was stored at 4° C. to avoid the evaporation. The PVB is useful for dispense casting as it is fully dissolvable material in THF solvent resulting in a uniform coating on the substrate without using any surfactants, an important advantage to develop uniform films without the need for using surfactants which may deteriorate the performance of the electrode. Finally, a perfluorinated polymer, Nafion (thickness ~10-20 nm) was deposited on PVB layer using auto-dispenser machine. The role for incorporating the third layer of this reference electrode is to prevent chloride ions leaving resulting from an enormous redox reactions of Ag/AgCl layer and to prevent the potential drift at RE. In addition, this proton exchange membrane also avoids other anions to enter into the membrane.

To investigate the chloride sensitivity, we have measured potentials for the fabricated electrodes such as Ag/AgCl wire, Ag/AgCl on Si needle, Ag/AgCl+PVC+Nafion and Ag/AgCl+PVB+Nafion with respect to commercial RE by varying Cl$^-$ concentration from 1 mM to 1M in DI water. Without coating of PVC, PVB and Nafion, the Ag/AgCl electrodes are highly sensitive to Cl$^-$ ions (FIG. 13a). Interestingly, with PVB and Nafion coating on Ag/AgCl electrode, S$^3$RE (Nafion/PVB/Ag/AgCl) do not show a potential change for different Cl$^-$ concentration (1 mM to 1M Cl$^-$). However, the S$^3$RE with PVC is showed a minute change of potential with different Cl$^-$ ionic solution. The higher polarity of PVB compared to PVC makes it less prone to fouling the membrane. This result suggests that the stable potential with PVC may be due to the formation of nanopores on the surface, which supply and control the flow of Cl—. To investigate the long-term stability, the fabricated electrodes were conducted to measure voltage for 30 days continuously. The voltage measurements were performed in a chamber filled with 0.1 mM Cl$^-$ solution with respect to commercial RE. Within 30 days of voltage measurements, the S$^3$RE with PVC incorporating does not change its potential (FIG. 13b). However, with PVC and without coating the Ag/AgCl showed a significant drift of potential. This new S$^3$RE can not only simplify the sensor structure by eliminating Cl$^-$ solutions, and but also reduce a potential drift of the sensor in response to different ionic strengths and for long-term measurement. With the long-term stability testing results, it can be concluded that the Nafion acted as a protection layer for S³RE to prevent the leakage of Cl⁻ ions.

In our design of working electrode or WE 30 (FIG. 14d), an 80 nm-thick Au was coated on Si/SiO$_2$ needle. The POT-MoS$_2$, a composite material (1 μm-thick) was deposited on the Au surface of the needle via liquid auto-dispenser machine and dried at room temperature. The POT-MoS$_2$ composite material was used to dissolve into THF solvent for a uniform coating on Au substrate. The main rationale for this composite material is boost the electrochemical signal (voltage) for the detection of nitrate ions and to act as ion-to-electron transfer in between Au and ion selective membrane (ISM). Finally, a ~4-5 μm-thick nitrate ion selective membrane was coated using auto-dispensing machine and the ISM is covered the entire surface of POT-MoS$_2$ material. SEM images (FIG. 14a-4c) show the morphological structure of MoS$_2$ sheets, porous structures of POT and full coverage of MoS$_2$ sheets by POT layers. FIG. 14d shows the pictorial representation of all layers with SEM images and FIG. 14e shows the cross-sectional of POT-MoS$_2$ layer.

Cyclic voltammetry studies of the fabricated sensors by incorporating different materials such as POT, MoS$_2$ and POT-MoS$_2$ showed the redox behavior in buffer solution (FIG. 14f). Oxidation current for MoS$_2$ electrode is obtained as higher (85 μA) compared to POT electrode (~28 μA). As we are interested in the voltage monitoring for our sensor system, when incorporated the MoS$_2$ into POT, the change of current is found to be slight (~5 μA) compared to POT electrode, however, the voltage shifted to higher value (85 mV). The inherent conducting feature of MoS$_2$ material is responsible to boost the voltage signal. A similar observation also found in FIG. 14g wherein the voltage between two electrodes during nitrate sensing wherein the magnitude of potential for POT-MoS$_2$ electrode exhibited a maximum value of 325 mV compared other electrodes such as POT (255 mV) and MoS$_2$ (66 mV).

FIG. 15 shows the contact angle studies to investigate the amphiphilic property of POT and POT-MoS$_2$ surface. The POT-MoS$_2$ has a high lipophilicity, indicating this has high capability to repel water molecules. Thus, this POT-MoS$_2$ acts as an ion-to-electron transfer layer and prevent the formation of water layer.

FIG. 16a-6c shows the output voltage of the nitrate sensor using the combined S³RE and POT-MoS$_2$ based electrodes when the sensor responded to varying nitrate-nitrogen ($NO_3^-$—N) concentrations from 1 ppm to 1500 ppm ($NO_3^-$—N). As the concentration increases, the output voltage of the sensor becomes more negative. The sensor with the S³RE and POT-MoS$_2$ exhibited a higher sensitivity, compared to the other two counterpart devices in which the POT or MoS$_2$ alone was combined with the ISM to form the WE, and the S³RE was used to provide a reference potential.

FIG. 16d shows the selectivity of the nitrate sensor and its comparison with the other two counterpart devices. It is shown that by incorporating the POT-MoS$_2$ nanocomposite in the working electrode, the sensor provided the highest selectivity in presence of the main interfering ions ($SO_4^{2-}$, $PO_4^{3-}$, Cl⁻, and K⁺) in the soil and water as evident by its low relative voltage change of ~13% compared to MoS$_2$ (~48%) and POT (~25%) electrodes.

FIG. 17 shows the repeatability (a) and long-term stability (b) test results for the fabricated sensor. In the repeatability test, the sensor was tested in presence of high and low concentration of nitrate-nitrogen solution. At high concentration of nitrate-nitrogen is found to be not stable with repeated time. This may be due to the water layer formation for the side-wall for the electrode. For long-term stability test of the sensor, it has found that the sensor has a potential drift in its output signal again due to the water layer formation at interface between ISM and POT-MoS2 or due to the leaching of Cl— ion at reference electrode.

XPS analysis: To confirm the chemical structures of POT-MoS$_2$ and ISM, XPS spectra were investigated. The XPS spectra shows the carbon is of MoS$_2$, POT-MoS$_2$ and ISM/POT-MoS$_2$ films (FIG. 18a-8c). After deconvolution into characteristic peaks, the C is peaks found to be at 284.9 eV, 285.9 and 289.5 eV indicating in the presence of C—C, C—OH and O—C═O groups. The presence of carbon may be due to the treatment of THF solution during their exfoliation. With incorporation of MoS$_2$ into POT solution, the peak found at 284.9 eV is changed to 0.4 eV with lower a full-width half maximum of 2.5 eV (FIG. 18b). After coating with ion-selective membrane (ISM), the peak location due to C—C is found to be at 284.3 eV (FIG. 18c). Another peak is obtained on the surface of ISM at 286.1 eV due to the C—O groups present in the membrane. FIG. 18d shows XPS two S 2p peaks of MoS$_2$ due to $2p_{1/2}$ and $2p_{3/2}$ at 165.5 eV and 164.9 eV, respectively. For the composite material of POT-MoS$_2$, S 2p peaks are found at 262.7 eV and 263.9 eV due to S*—Mo groups and C—S*—C groups [Ref: Wang et al., Polymer Journal, 38, 484-489, 2006] and the peak found at 269.2 eV is due to S—O groups. In the XPS peaks for Mo 3d, it shows a peak at 227.2 eV due to S 2s, and other peaks at 229.9 eV, 233.1 eV and 236.4 eV are due to the $Mo^{4+}3d_{5/2}$, $Mo^{4+}3d_{3/2}$ and $Mo^{6+}3d_{3/2}$ (FIG. 18g). However, additional two found at 233.1 eV and 231 eV are because of $Mo^{6+}3d_{5/2}$ and $Mo^{5+}3d$ after incorporating of POT (FIG. 18h). These studies can confirm that for the composite material between POT and MoS$_2$ due to their electrostatic interactions. N is peaks in the XPS spectra of ISM on POT-MoS$_2$ are obtained at 402.7 eV and 408.4 eV indicate —NH$_2$ and nitrooxy (—N—NO$_2$) groups due to presence of nitrocellulose in the membrane.

Electrochemical Characterization: Cyclic voltammetry studies of the fabricated sensors by incorporating different materials such as POT, MoS$_2$ and POT-MoS$_2$ showed the redox behavior in phosphate buffered saline (PBS) solution (FIG. 19a) containing ferro-ferri cyanide redox probe. Oxidation current for MoS$_2$ electrode is obtained as higher (91 μA) compared to POT electrode (32 μA). With composite, the oxidation current is increased to 47 μA due to high conductive nature of MoS$_2$ sheets. As we are interested in the voltage monitoring for our sensor system, when incorporated the MoS$_2$ into POT, the change of current is found to be slight (15 μA) compared to POT electrode, however, the voltage shifted to higher value (95 mV). Thus, inherent conducting feature of MoS$_2$ material is responsible to boost the voltage signal which may result higher sensing ability of the device. All the three electrode were conducted to investigate the redox properties by varying the scan rate from 20 to 200 mV/s (FIG. 19b-9c). The electrodes showed the surface-controlled process, quasi-reversible and the potential differences due to oxidation and reduction of redox molecules are found to shift towards higher values with increase scan rates (FIG. 19d). The lower peak-to-peak potential difference of the POT-MoS$_2$ electrode is found to less compare to bare MoS$_2$ electrode due to fast electron transfer between the solution and electrode (FIG. 19e). With ion-selective membrane coating on POT surface, the electrodes do not show the redox reaction of ferro-ferry cyanide molecules due to non-conducting behavior of ion-selective membrane (FIG. 19f).

E. Specific Example 2

With particular reference to FIGS. 20 to 29A-C, a second example of apparatus, methods, and systems according to the invention is set forth. This is taken from Md. Azahar Ali, Xinran Wang, Yuncong Chen, Yueyi Jiao, Navreet K. Mahal, Satyanarayana Mom, Michael J. Castellano, James C. Schnable, Patrick S. Schnable, and Liang Dong, ACS Appl. Mater. Interfaces 2019, 11, 29195-29206, which is incorporated by reference herein in its entirety, including Supporting Information available free of charge on the ACS Publications website at DOI: 10.1021/acsami.9b07120. FIG. 20 shows the basic concepts, as further described below.

Continuous Monitoring of Soil Nitrate Using a Miniature Sensor with Poly(3-Octyl-Thiophene) and Molybdenum Disulfide Nanocomposite ABSTRACT: There is an unmet need for improved fertilizer management in agriculture. Continuous monitoring of soil nitrate would address this need. This paper reports an all-solid-state miniature potentiometric soil sensor that works in direct contact with soils to monitor nitrate-nitrogen ($NO_3^-$—N) in soil solution with parts-per-million (ppm) resolution. A working electrode is formed from a novel nanocomposite of poly(3-octyl-thiophene) and molybdenum disulfide (POT-$MoS_2$) coated on a patterned Au electrode and covered with a nitrate-selective membrane using a robotic dispenser. The POT-$MoS_2$ layer acts as an ion-to-electron transducing layer with high hydrophobicity and redox properties. The modification of the POT chain with $MoS_2$ increases both conductivity and anion exchange, while minimizing the formation of a thin water layer at the interface between the Au electrode and the ion-selective membrane, which is notorious for solid-state potentiometric ion sensors. Therefore, the use of POT-$MoS_2$ results in an improved sensitivity and selectivity of the working electrode. The reference electrode comprises a screen-printed silver/silver chloride (Ag/AgCl) electrode covered by a protonated Nafion layer to prevent chloride ($Cl^-$) leaching in long-term measurements. This sensor was calibrated using both standard and extracted soil solutions, exhibiting a dynamic range that includes all concentrations relevant for agricultural applications (1-1500 ppm $NO_3^-$—N). With the POT-$MoS_2$ nanocomposite, the sensor offers a sensitivity of 64 mV/decade for nitrate detection, compared to 48 mV/decade for POT and 38 mV/decade for $MoS_2$. The sensor was embedded into soil slurries where it accurately monitored nitrate for a duration of 27 days.

Introduction

Low-cost, high-performance nutrient sensors that continuously monitor soil conditions for precision agriculture,[1,2] plantphenotyping,[3] and environmental quality[2] are in high demand. Soil is the primary source of nutrients for plant growth.[4-7] Biologically available soil nitrogen (N) is one of the key limiting factors in plant growth, and crop productivity relies heavily on the application of supplemental N in the form of fertilizers. Yet, the proper amount of N fertilizer input can vary within fields by >100% per year because of the variation in the soil N supply that is mostly caused by interannual weather variability. Insufficient N fertilizer input reduces crop production and excessive N input harms the environment. Farmer income suffers from both.

Continuous monitoring of N dynamics in agricultural fields would help maximize control over fertilizer management. Several laboratory-based soil N measurement methods are widely used, such as gas chromatography-mass spectrometry (GC-MS), ultraviolet-visible (UV-vis) spectrophotometry, ion chromatography, and chemiluminescence.[8-12] Although these methods are highly sensitive and selective and exhibit superior performance, they are known to have instrumentation complexity and need laborious and time-consuming tasks. Colorimetric determination of nitrate relies on the reduction of nitrate by vanadium(III), combined with detection by the Griess reaction, and needs extraction of nitrate ions from soil samples using a high-concentration (e.g., 2 M) KCl solution, which limits its practical operation in fields.[7] With an increasing demand for on-site nitrate monitoring, mobile vehicle-based nitrate sensors[13] have been reported but still require significant labor and are relatively expensive. Satellite remote sensing[14] provides an indirect measure of plant N dynamics and does not currently provide high accuracy or spatial resolution. The development of field-deployable soil nitrate sensors is an attractive solution to better manage N fertilizers. Noteworthy in-field nitrate sensing methods include electrochemical sensors,[5,6,15] ion-selective electrodes (ISEs),[16,17] and microfluidic electrophoresis.[18] However, these miniature sensor methods need further development or remain challenging mainly because of the suboptimal sensitivity, relatively high signal drift, and material instability.[19]

Ion-selective membrane (ISM)-based sensors are considered a promising approach to detecting soil nutrients. Many ISEs are manufactured by simply coating thin metal wires with ISMs. However, redox-active charged species are difficult to be transferred to metal wires, leading to a capacitive interface with the wire.[20] Conversely, nonmetal wire-based ISEs often require an inner filling solution between the ISM and a conductive metal layer substrate;[21-25] the main drawbacks, however, include easy contamination of the filling solution with interfering ions, gradual evaporation of the solution, variations in both osmolality and ionic strength, membrane delamination, poor adhesion, and difficulty in device miniaturization.[23,26]

Although ISEs that do not use inner filling solutions are an attractive option, a thin water layer that often forms at the interface between the conducting metal layer and the ISM has created a major challenge to the development of these sensors. Usually, this thin water layer presents an interfacial barrier to fast electron transfer and negatively impacts the selectivity of the sensor to specific ions because different ions are trapped inside 4.[27,28] Therefore, significant attempts have been made to replace the inner filling solutions with solid-contact materials as ion-to-electron transducing layers, with the objective of realizing an all-solid-state miniature ionsensor.[29-33] Many solid-contact candidate materials have been investigated, including hydrogel,[34] carbon nanotubes (CNTs),[35,36] graphene,[32] polymer-carbon composites,[37] metallic nanostructures,[38] macroporous carbon,[39] and conjugated conducting polymers such as polyaniline,[19] poly(3,4-ethylenedioxythiophene) (PEDOT),[40] and poly(3-octyl-thiophene-2,5-diyl) (POT).[27,41,42] Of these, PEDOT has a strong ability to oxidize to PEDOT⁺ and thus has been extensively used as a solid-contact material 30 to attract lipophilic ions from the ISM to the conducting metal layer to establish a potential equilibrium. As another promising candidate, electropolymerized,[41,42] drop-casted,[43] and Langmuir-Blodgett[44] POT is redox-sensitive and can be oxidized reversibly in anion solutes with a low ohmic voltage drop; in addition, the high hydrophobicity of POT restricts the formation of a water layer between POT and the ISM. Recently, the incorporation of 7,7,8,8-tetracyanoquinodimethane (TCNQ) into a POT matrix contributed to reducing the potential drift by more than one order of magnitude because of the introduction of a TCNQ/TCNQ⁻ redox couple.[45] Despite its high redoxproperty,41 POT has a relatively low conductivity (approximately $10^{-6}$ S/cm)[28] and is also sensitive to light,[36] which negatively impacts the efficiency of charge transport through POT to the conducting metal substrates.

Here, we report a miniature solid-state potentiometric sensor for the continuous monitoring of soil nitrate. The sensor uses a nanocomposite of POT and transition-metal dichalcogenides of molybdenum disulfide ($MoS_2$) nanosheets[46] as a solid-contact ion-to-electron transducing layer. $MoS_2$ nanosheets provide large surface area, high conductivity,[47] insensitivity to light and pH, and absence of any side reactions. The working electrode (WE) was built on top of a copper pad of a printed circuit board (PCB) covered by a thin, patterned gold (Au) layer, a $MoS_2$ (POT-$MoS_2$) nanocomposite-based solid-contact layer, and a nitrate-specific ISM. The incorporation of $MoS_2$ into POT not only increases the redox properties of POT[48] but also maintains high hydrophobicity to minimize the formation of a thin water layer between the ISM and the Au layers. The use of POT-$MoS_2$ remedies the issue of the trapped water layer, thus contributing to the increased charge transfer and ion selectivity of the WE.[49-51] The reference electrode (RE) of this nitrate sensor includes a silver/silver chloride (Ag/AgCl) electrode covered by a proton exchange membrane to reduce the redox reaction induced chloride leaching from the RE, thus minimizing the drift of the reference potential. The sensor features an all-solidstate design that incorporates the POT-$MoS_2$ nanocomposite for improved device performance. The sensor can also be directly embedded in soil slurries for continuous measurement of nitrate dynamics for approximately 4 weeks. Furthermore, all the sensor materials (except for the screen-printed Ag/AgCl and evaporated Au) are deposited and patterned using a high resolution dispensing robot with good control over the uniformity of material thickness.

Materials, Manufacturing, and Circuits

Materials. Methyltriphenylphosphonium bromide, polyvinylchloride, Nafion, nitrocellulose, 2-nitrophenyl octyl ether, tetrahydrofuran (THF), and tridodecylmethylammonium nitrate were purchased from Sigma-Aldrich, MO. Polyvinyl butyral, regioregular POT, and Ag/AgCl ink (composed of finely dispersed chloritized silver flakes) were obtained from Fisher Scientific, MA. Ultrafine powders of $MoS_2$ nanosheets were obtained from Graphene Supermarket, NY. Deionized water with a resistivity of 18.2 M Ω cm was obtained using a purification system from Millipore, Mass. Potassium nitrate ($KNO_3$), calcium sulfate ($CaSO_4$), sodium chloride (NaCl), sodium bicarbonate ($NaHCO_3$), and sodium phosphate monobasic ($NaH_2PO_4$) were also obtained from Fisher Scientific, MA. The PCB was manufactured by OHS PARK, OR.

The $NO_3^-$ ISM cocktail contained methyltriphenylphosphoniumbromide (0.25 wt %), nitrocellulose (moistened with 2-propanol (35%); 1.93 wt %), 2-nitrophenyl octyl ether (16.25 wt %), polyvinylchloride (5.75 wt %), THF (74.3 wt %), and tridodecylmethylammonium nitrate (1.50 wt %). This solution was sealed and stored at −20° C.[52]

Nanocomposites of POT-$MoS_2$. The weight ratio of POT to $MoS_2$ was varied from 1:1 to 1:10 to study the influence of material composition on the redox properties of different POT-$MoS_2$ nanocomposites. In each case, the concentration of the POT solution was fixed at 2.6 mg/mL. For example, to prepare a POT-$MoS_2$ sample with a 1:4 weight ratio of POT to $MoS_2$, 2.6 mg of POT powder was dissolved in 1 mL of THF solvent. A 10.4 mg $MoS_2$ was added to the POT solution and sonicated for 4 h. Because of the attraction between the opposite charges of $MoS_2$ and POT, a homogeneous solution of POT-$MoS_2$ nanocomposite was formed.

Electronic Circuitry. A homemade data logger with an embedded readout circuitry was used to detect and record potential variations between the WE and RE. The voltage potential provided by the sensor was first isolated from other parts of the readout circuit using two buffer amplifiers. Then, the output signal from the buffer amplifiers was fed to a differential amplifier to obtain a single output voltage, which could be further enhanced fivefold by using an inverting amplifier. Further, a voltage lifter circuit was introduced to obtain both negative and positive data from the sensor using a microcontroller. A two-order filter with 1 Hz cutoff frequency was then used to reduce the noise signal at the output. Finally, an Adafruit Feather 32u4 microcontroller was used to realize the analogue-to digital signal conversion.

Device Fabrication. The sensor had two 5 mm diameter, round shaped electrodes formed on the PCB that served as WE 30 and RE 40. The rectangular pads on the PCB allowed for connecting the WE and RE to an external data logger. The base material of the WE and RE was copper. With the help of a shadow mask, a 5.2 mm diameter and 100 nm thick Au layer was deposited on top of one of the base electrodes using electron beam evaporation. The same approach was used to form a 5.2 mm diameter and 500 nm thick Ag layer on top of the other base electrode. FIG. 21*a* shows a wafer-scale PCB containing arrays of RE 40 and WE 30. To form the POT-$MoS_2$ nanocomposite and nitrate-selective ISM layers, a high-precision, automated fluid dispensing robot (Nordson EFD, RI) was used to dispense the prepared POT-$MoS_2$ and ISM solutions, respectively, on top of the Au surface (FIG. 21*c*). During this process, the POT-$MoS_2$ solution was first dispensed out of a syringe (size 10 cc) under an air pressure of 2 psi, followed by thermal treatment on a hot plate at 65° C. for 1 h. After the ISM solution was dispensed, the WE was dried at room temperature for 10 h. The same material coating technique was applied to make other WEs using POT or $MoS_2$ alone as the solid contact ion-to-electron transducing layer for comparison with the proposed WE with the POT-$MoS_2$ nanocomposite. To form the RE of the sensor, the round-shaped Ag electrode was further screen printed with Ag/AgCl paste using a stencil mask placed on top of the PCB. The 200 μm thick Ag/AgCl paste was dried at 110° C. for 2 h. To prevent the leaching of chloride ions as a result of the redox reaction of Ag/AgCl during long-term measurements,[53] a 15 nm thick perfluorinated polymer layer, or Nafion, was coated on the surface of Ag/AgCl using the above-mentioned fluid-dispensing robot and was then dried at 90° C. for 1 h. In addition, the Nafion layer could also block anions entering the RE from the surrounding environment. Finally, a 1.2 mm thick waterproof insulating epoxy (CircuitWorks, CW2500) was used to cover the PCB, except for the regions of the WE, RE, and contact pads. This insulation layer impedes water penetration from the sidewalls of the coated materials when the sensor is embedded in soil slurries. The sensor was preconditioned by dipping it into 1500 ppm $NO^-_3$—N solution for 24 h. FIG. 21*c* shows the fabricated solid-state nitrate sensor.

Working Principle. As the ion-to-electron transducing layer, the POT-$MoS_2$ nanocomposite layer undergoes a redox reaction during sensing. The mechanism of anion (or cation) exchange through POT is demonstrated in the previously reported literature.[27] Si and Bakker demonstrated a cyclic voltammetric experiment for the anion (lipophilic) exchange process in a POT electrode-based ion-selective membrane.[27] Kim and Amemiya also explained the anion exchange in a POT film coated with ISM using ion-transfer stripping voltammetry.[42] FIG. 22 shows the oxidation and reduction associated with the sensing mechanism. The mechanism for extracting electrochemically mediated anions ($NO_3^-$) into the ISM involves three phases,[27] including (1) oxidizing POT-$MoS_2$ (or P) to (POT-$MoS)^+$ (or $P^+$); (2) triggering the extraction of $NO_3^-$ from the test sample; and (3) redistributing lipophilic anions ($R^-$) from the ISM to the POT-$MoS_2$ layer. The corresponding redox reaction accompanied by $NO_3^-$ transfer at the ISM is given by

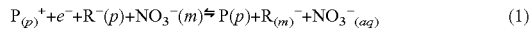

$$P_{(p)}^+ + e^- + R^-(p) + NO_3^-(m) \rightleftharpoons P(p) + R_{(m)}^- + NO_3^-_{(aq)} \quad (1)$$

where m, p, and aq represent the ISM phase, POT-$MoS_2$ nanocomposite phase, and aqueous phase, respectively, and $P_{(p)}$ and $P_{(p)}^+$ represent a few monomeric units of the POT chain in the neutral insulating state and the oxidized state with polaronic sites, respectively. Owing to the oxidation process (FIG. 22a), POT-$MoS_2$ extracts the sample anions $NO_3^-_{(aq)}$ into the ISM and forces their distribution of the lipophilic anions ($R^-$) into the POT-$MoS_2$ layer. In the reduction process (FIG. 22b), (POT-$MoS_2$)+becomes neutral POT-$MoS_2$, releasing the lipophilic anions $R^-$ (p) into the ISM, which in turn leads to a release of $NO_3^-_{(aq)}$ from the outer membrane ($NO_3^-_{(m)}$) into the test solution. Therefore, by combining the redox and ion-exchange processes at the WE, an equilibrium is established at the aqueous—nanocomposite—ISM interfaces, leading to charge separation at each interface, thus generating a phase boundary potential.12 This phase-boundary potential $E_1$ is given by $E_1$= (RT/zF)×ln $a_I$, where R, T, z, F, and $a_I$ represent the gas constant, temperature, charge of the target ion, the Faraday constant, and the primary ion activity without interfering ions, respectively. On the other hand, the RE of the sensor also undergoes a redox reaction, providing a constant potential ($E_0$).[54] The Nafion layer coated on the surface of Ag/AgCl not only minimizes the leaching of the chloride ion from Ag/AgCl but also blocks the other anions in the external environment from entering the RE. As the anions or cations move from high to low regions of concentration, a potential difference is produced during the ion exchange. Therefore, the potential (E) is dependent on the logarithm of the ion activity and is described by the Nernst equation[55]

$$E = E_0 + E_1 = E_0 + (RT/zF)\ln a_I \quad (2)$$

To determine the ion selectivity of the sensor, according to Nikolskii-Eisenman formalism,[56] the logarithm term in eq 2 can be replaced by a sum of selectivity-weighted activities given by $$E = E_0 + (RT/nF)\ln(a_I + K_{I,J}^P a_J^{Z_I/Z_J}) \quad (3)$$

where $K_{I,J}^P$ is the selectivity coefficient, $a_I$ and $a_J$ are the activities of I and J, respectively, in the test solution, and $Z_I$ and $Z_J$ are the charges of the primary and interfering ions, respectively.

Results and Discussion

Surface Morphology and Water-Repellent Properties. FIG. 23 shows the scanning electron microscopy (SEM) images for different ion-to-electron transducing layers formed on the Au surface, including $MoS_2$, POT, and POT-$MoS_2$ nanocomposites. The $MoS_2$ layer is seen as a mixture of $MoS_2$ sheets of different sizes (FIG. 23a). The POT film exhibits continuous distribution and microtexture (FIG. 23b). In the POT-$MoS_2$ nanocomposite, $MoS_2$ sheets are embedded with POT because of the electrostatic interactions between them (FIG. 23c,d). In addition, FIG. 23e-g shows the measured water contact angles of the $MoS_2$ (Θ=68°), POT (Θ=86°), and POT-$MoS_2$ (Θ=107°) surfaces. With $MoS_2$, the nanocomposite remains hydrophobic, which may contribute to minimizing the formation of a thin water layer between the ISM and Au layers.

XPS Analysis. X-ray photoelectron spectroscopy (XPS) was conducted to confirm the chemical structures of $MoS_2$, POT-$MoS_2$, and ISM/POT-$MoS_2$. FIG. 24a-c shows the carbon is spectra of the $MoS_2$, POT-$MoS_2$, and ISM/POT-$MoS_2$ layers coated on the Au surface. After deconvolution into characteristic peaks, the C is peaks of $MoS_2$ are found at 284.9, 285.9, and 289.5 eV, indicating the presence of C—C, C—OH, and O—C═O groups, respectively.[57] The presence of carbon may be because of the impurity of the $MoS_2$ sheets. The incorporation of $MoS_2$ into the POT matrix leads to a shift in the peak location from 284.9 to 285.3 eV with a full width half maximum of 2.5 eV (FIG. 24b), perhaps because of the POT hydrocarbons. A peak at 285.8 eV can be ascribed to the C—S bond, indicating the formation of a strong chemical bonding at the interface between $MoS_2$ and POT. After the ISM was coated on the POT-$MoS_2$ layer, the peak for the C—C bond was found to be at 284.3 eV (FIG. 24c). Another peak at 286.1 eV was obtained on the surface of ISM because of the C—O group present in the ISM.

FIG. 24d shows the $MoS_2$ layer with two S 2p core-level peaks of $MoS_2$ at the binding energies of 165.5 and 164.9 eV, corresponding to the S $2p_{1/2}$ and S $2p_{3/2}$ orbitals of divalent sulfide ions ($S^{2-}$). In FIG. 24e, two S 2p peaks appear at 162.7 and 163.9 eV because of the formation of S*—Mo and C—S*—C groups, respectively,[58] indicating the incorporation of POT into $MoS_2$, and another peak found at 169.2 eV is associated with S in sulfone. Furthermore, the S peaks were observed to shift toward higher energies of 1.6 and 1.2 eV because of the ISM coating on the POT-$MoS_2$ film (FIG. 24f).

In the Mo 3d spectrum of $MoS_2$, a peak at 227.2 eV corresponds to S 2s with a chemical state of $S^2$, whereas other peaks at 229.9, 233.1, and 236.4 eV are ascribed to $Mo^{4+}3d_{5/2}$, $Mo^{4+}3d_{3/2}$, and $Mo^{6+}3d_{3/2}$, respectively (FIG. 24g). For POT-$MoS_2$ (FIG. 24h), two additional peaks appear at 233.1 and 231 eV because of $Mo^{6+}3d_{5/2}$ and $Mo^{5+}3d$, respectively. In the N is spectrum of ISM/POT-$MoS_2$ (FIG. 24i), the peaks seen at 402.7 and 408.4 eV correspond to the —$NH_2$ and nitrooxy (—N—$NO_2$) groups because of the presence of nitrocellulose in the ISM. Therefore, the formation of a composite between POT and $MoS_2$ because of the appearance of the chemical C—S bond is confirmed. Further, the presence of the —$NH_2$ and nitrooxy (—N—$NO_2$) groups at ISM/POT-$MoS_2$ indicates the ISM coating on the surface of the POT-$MoS_2$ matrix.

Electrochemical Characterizations. Cyclic voltammetry (CV) was conducted at room temperate to investigate the redox properties of the $MoS_2$, POT, POT-$MoS_2$, and ISM/POT-$MoS_2$ layers coated on the Au electrodes (FIG. 25a), and the POT to $MoS_2$ ratio of the composite was set to 1:4. The cyclic voltammograms for the $MoS_2$-, POT-, and POT-$MoS_2$-based electrodes exhibited clear reversible oxidation and reduction reactions for the $[Fe(CN)_6]^{3-/4-}$ redox probes. The oxidation current for the POT-$MoS_2$-based electrode was higher (115 µA) than that for the $MoS_2$-based electrode (90 µA) and the POT-based electrode (65 µA) because the incorporation of high-conductivity $MoS_2$ facilitates an improved electron transfer from POT-$MoS_2$ to the Au current conductor. Also, the values of peak-to-peak potential difference (4E) for the POT- and POT-$MoS_2$-based electrodes were found to be 0.127 and 0.38 V, respectively. After modification with the ISM, the POT-$MoS_2$-based electrode exhibited reduced oxidation and reduction peaks for the $[Fe(CN)_6]^{3-/4-}$ redox probes, perhaps because of sluggish ion exchanges or a high selectivity of ISM that rejected [Fe(CN)$_6$]$^{3-/4-}$ ions (inset of FIG. 25a).

To optimize the weight ratio of POT to MoS$_2$ in composite formation, CV measurements were taken for composites at varying weight ratios with the objective of obtaining the composite that offered the largest value of ΔE. FIG. 25b shows that as the weight ratio of POT to MoS$_2$ changes from 1:1 to 1:10, the obtained ΔE increases at lower weight ratios, reaches a maximum ΔE=0.345 V at a 1:4 weight ratio, and then deceases at higher weight ratios. Further, FIG. 25c shows that the oxidation current decreases with increasing POT-to-MoS$_2$ weight ratios from 1:1 to 1:3 because of a reduction in the free POT in the POT-MoS$_2$ matrix. At a weight ratio between 1:4 and 1:6, the oxidation current is observed to be relatively stable at a low value because of the full bond formation. With a further increase in the MoS$_2$ component, the free MoS$_2$ in the matrix prompts the oxidation current because of the inherent electroactivity of MoS$_2$ (FIG. 25c). Therefore, for potentiometric measurements, the optimum POT-to-MoS$_2$ weight ratio was chosen to be 1:4.

FIG. 25d presents the redox activity studies of the POT-MoS$_2$-based electrode (POT-to-MoS$_2$ weight ratio, 1:4). The POT-MoS$_2$-based electrode shows a good redox behavior for the oxidation and reduction of ferro-/ferricyanide redox species. The difference between the oxidation and reduction potentials is found to increase with an increase in the scan rate. The peak current is proportional to the square root of the scan rate (inset of FIG. 25d), indicating a diffusion-controlled process on this redox-sensitive material.

For open-circuit potential (OCP) measurements, the MoS$_2$, POT, and POT-MoS$_2$ layers were coated with nitrate-specific ISM. FIG. 25e shows the output voltage signals of the fabricated sensors in response to 1000 ppm NO$_3^-$—N. The magnitude of the potential for the POT-MoS$_2$-based electrode exhibits a maximum value of 325 mV, higher than the counterpart electrodes using POT (255 mV) and MoS$_2$ (66 mV). As is evident in the CV studies (FIG. 25a), compared to POT alone, the POT-MoS$_2$ nanocomposite offers a better redox property and functions as a good electroactive mediator to allow selective interaction with NO$_3$— ions in the surrounding solutions (FIG. 23a,b), thus providing an increased OCP.

The potential stability of the electrodes and the electrical capacitance of the solid contact were evaluated using chronopotentiometry[19] (FIG. 26f). The characteristic chronopotentiometric curves present the change in potential overtime measured in a 500 ppm NO$_3^-$—N solution. The obtained results are shown in FIG. 26. The potential drift of electrode was calculated as ΔE/Δt. The ΔE/Δt values for the POT-, MoS$_2$-, and POT-MoS$_2$-based nitrate-selective electrodes were found to be 115.4, 213.3, and 95 μV s$^{-1}$, respectively. Similarly, the low-frequency capacitances C of the POT-, MoS$_2$-, and POT-MoS$_2$-based electrodes were estimated to be 433, 234, and 526 μF, respectively, according to the equation ΔE/Δt=I/C. These results indicate that the POT-MoS$_2$-based electrode has a larger capacitance and a lower potential drift compared to the electrode using POT or MoS$_2$ (see, infra, Table S1, Supporting Information).

Quantification of Nitrate-Nitrogen. Nitrate detection by the sensors using MoS$_2$, POT, and POT-MoS$_2$ as the solid contact ion-to-electron transfer layer materials was investigated. FIG. 26a shows the calibration curves, that is, the OCP values of the sensors as a function of nitrate concentration ranging from 1 to 1500 ppm (NO$_3^-$—N). The slope of the voltage response versus logarithm concentration for the POT-MoS$_2$-based sensor is 64 mV/decade (10-1500 ppm), which is higher than that of POT (approximately 48 mV/decade, 10-1500 ppm) and MoS$_2$ (approximately 38 mV/decade, 10-1500 ppm). The high electroactivity and redox property of the POT-MoS$_2$ layer is believed to contribute to improved sensitivity in nitrate detection. In addition, the high hydrophobicity of the POT-MoS$_2$ layer could minimize water accumulation between the ISM and the Au current collector, lowering the barrier of charge transfer to the Au layer and thus improving the sensor sensitivity. Although the MoS$_2$-based sensor also provides a wide dynamic range up to 1000 ppm (NO$_3^-$—N), the output voltage was found to be unstable (particularly during the detection of high nitrate concentrations), possibly because of poor adhesion of the MoS$_2$ layer to the ISM layer, leading to membrane delamination. Following the method described by Buck and Lindner,[59] we calculated the limit of detection (LOD) as 0.84, 1.3, and 1.4 ppm for the three sensors using MoS$_2$, POT, and POT-MoS$_2$, respectively, according to the obtained calibration plots (FIG. 26a). Table 1 below compares nitrate monitoring using different nanostructured materials. The laboratory-based nitrate measurement methods based on Griess assay, UV-Vis spectrophotometry, GC-MS, and chemiluminescence for nitrate monitoring in different media showed higher performance in terms of their LOD compared to the POT-MoS$_2$-based sensor. However, our sensor can perform long-term measurements, exhibit a wider detection range, and have considerable performances suitable for field applications.[8-12] In addition, our sensor uses an integrated solid-state RE, thus offering the possibility of miniaturization and mass production, whereas the above-mentioned counterpart sensors require commercial large-sized REs. The sensor is used in direct and long-term contact with soil particles across a range of wetness for nitrate quantification.

Selectivity, Repeatability, and Stability Studies. FIG. 26b shows the selectivity of the sensors using MoS$_2$, POT, and POT-MoS$_2$ as the ion-to-electron transducing layers in the presence of interfering anions such as chloride (Cl$^-$), phosphate (PO$_4^{3-}$), bicarbonate (HCO$_3^-$), sulfate (SO$_4^{2-}$), and nitrite (NO$_2^-$). The selectivity coefficient, $K_{I,J}^P$, described in eq 4, is a numerical measure of how adequately the sensor is able to discriminate against the interfering ions.

$$K_{I,J}^P = a_I/(a_J^{Z_I/Z_J}) \tag{4}$$

where $a_I$, $a_J$, $Z_I$, and $Z_J$ are the activity of primary ions, activity of interfering ions, charge of the primary ions, and charge of the interfering ions, respectively. According to IUPAC recommendations, a matched potential method, including the separate solution method (SSM), is practical and unique for estimating $K_{I,J}^P$, which does not depend on the Nikolskii-Eisenman equation.[70,71] In the SSM method, the potential of the sensor is adjusted by introducing two different concentration solutions separately, wherein one contains the ion I with activity $a_I$ (no J) and the other one contains the ion J with the same activity $a_J$ (no I) to attain the same measured potential. To calculate the value of $K_{I,J}^P$, $a_I$ was calculated from the extrapolated calibration graph where the potential of the interfering ion concentration ($a_J$) is equal. The result demonstrates that the POT-MoS$_2$-based sensor shows less susceptibility to PO$_4^{3-}$ and SO$_4^{2-}$ than the sensor using POT or MoS$_2$ alone as the transducing layer, perhaps because of the improved hydrophobicity of the POT-MoS$_2$ layer, whereas the influence of HCO$_3^-$ and Cl$^-$ on the output potential is comparable among all the sensors. For NO$_2^-$, the sensors based on POT or MoS$_2$ showed more negative selectivity coefficients compared to the POT-MoS$_2$-based sensor.

TABLE 1

Comparison of $NO_3$—N Monitoring Using Different Nanomaterials and Techniques

| electrode materials or transducers | methods | test range (ppm) | detection limit (ppm) | sensitivity (mV/dec) | test period and environment | refs |
|---|---|---|---|---|---|---|
| CNTs | OCP | $0.14 \times 10^{-3}$ to 14.02 | 0.0014 | 58.9 | NA | 60 |
| polypyrrole | OCP | 0.14-1400.6 | 0.42 | 53.9 | 7 d in water | 61 |
| graphene | OCP | 0.14-1400.6 | 0.3 | 54.8 ± 2.5 | not tested | 62 |
| polypyrrole | OCP | 1.4-56.1 | 1.68 | 51.6 | not tested | 63 |
| POT | OCP | 0.14-1400.6 | NA | 53 | ~90 d in water | 64 |
| poly(aniline) | OCP | 0.14-1400.6 | NA | 51.5 | ~90 d in water | 64 |
| PEDOT | OCP | 0.011-63.34 | 0.25 | NA | NA | 65 |
| ionic liquid | OCP | 0.044-442.8 | 0.012 | 60.1 | NA | 66 |
| graphene-tetrathiafulvalene | OCP | 0.004-442.8 | ~0.004 | 59.14 | NA | 67 |
| carbon black | OCP | 0.044-442.8 | 0.1 | 60 | NA | 68 |
| tetrathiafulvalene | OCP | 0.044-442.8 | 0.01 | 58.8 | NA | 69 |
| spectroscopic | VCl3/Griess | 0.02-5 | 0.016 | NA | NA | 8 |
| optical | Greiss | 0-9.3 | 0.027 | NA | sea water | 9 |
| optical | V | 0.3-3.1 | 0.007 | NA | waste water | 10 |
| optical | chemiluminescence | 0.001-0.9 | 0.001 | NA | atmospheric | 11 |
| gas chromatography | nitration | 0.062-6.2 | 0.1 | NA | ~3 d in | 12 |
| POT —MoS2 | OCP | 1-1500 | 1.3 | 64 | 25 d in soil | this work |

FIG. 26c shows the stability of fabricated Nafion-modified Ag/AgCl RE with respect to commercial RE by varying the KCl concentration from 0.01 to 3 M KCl. Without the Nafion coating, the Ag/AgCl electrode shows a stable OCP with 0.01 and 0.05 M of KCl concentration; however, with a higher concentration of KCl, such as 1 and 3 M, the electrode shows a significant potential change. This change of potential is due to the considerable electrochemical reaction in the AgCl layer, which may leach Cl⁻ ions from the AgCl layer, resulting in an unstable OCP. With increasing KCl concentration, the Nafion modified Ag/AgCl electrode does not show a change in OCP. The pronated Nafion layer on the Ag/AgCl surface acts as a protective layer that does not allow Cl⁻ ions to leach out and rejects Cl⁻ from outside the Nafion. FIG. 26d shows the long term stability (approximately 32 days) of the fabricated solidstate Ag/AgCl electrode with and without a Nafion layer in the presence of 0.01 M of KCl. With no Nafion coating on the Ag/AgCl surface, the OCP was not constant in long-term measurements because of Cl⁻ leaching. However, blocking the Ag/AgCl surface with Nafion resulted in an almost constant OCP for 32 days with a minimum drift. This indicates that Nafion-coated Ag/AgCl is not externally influenced by Cl⁻ ions and is more stable for long-term measurements.

To investigate the repeatability of the sensor, we repeatedly measured OCP as the sensor was transferred between 1 and 1300 ppm $NO_3^-$—N(FIG. 29C, Supporting Information). For 12 repeated measurements, the sensor was dipped in a high nitrate-nitrogen (1300 ppm) concentration for 2 min, and the OCP was recorded. Then, the sensor was immediately dipped in a low concentration of nitrate-nitrogen (1 ppm) and then washed with DI water for another 2 min, and the OCP was recorded. The sensor responded in less than 5 s when switching from a high to low concentration, or vice versa. With the high concentration of $NO_3^-$—N(1300 ppm), the percentage of relative standard deviation for the output voltage was calculated as ±3.0%, whereas with the low concentration, the sensor showed a deviation of ±5.0% over six repeated measurements. This result indicates high repeatability of the test.

For the interference study in the presence of $CO_2$, the POT-$MoS_2$-based sensor was tested in a closed chamber with a controlled $CO_2$ environment (FIG. 26e). Before the measurement, the $CO_2$ gas (saturated) was injected into a nitrate solution for 15 min to ensure satirized dissolution of $CO_2$ in the solution. The test result shows that the introduction of $CO_2$ into the solution led to a ±5% relative deviation from the initial signal of the sensor. This may be caused by a pH change induced by the dissolved $CO_2$ in the solution. Also, we found that the introduction of $N_2$ into the solution had almost no influence on the sensor readout. Nevertheless, the sensor exhibited a good potential stability in the $CO_2$ environment.

We studied the reproducibility of the POT-$MoS_2$-based nitrate electrode (FIG. 29A, Supporting Information). The concentration of $NO_3^-$—N was set to 100 ppm in DI water, and the measurement was performed for 2 min for each POT-$MoS_2$ electrode. The results show that the variation in potential among these electrodes is negligibly small, as evident by its low relative standard deviation (RSD=~3.5%) because of the uniform coating of the electrode materials (i.e., POT-$MoS_2$ and ISM) using a high-resolution robotic dispensing machine.

We carried out potential stability measurements for the POT-$MoS_2$-based nitrate sensor over ~10 days (FIG. 29B, Supporting Information). The electrode was preconditioned in a 1500 ppm $NO_3^-$—N solution for 3 days. The result of the continuous measurement shows that the potential at day 10 (~−184 mV) remained almost unchanged from the initial potential (~−186 mV). Therefore, the preconditioned electrode was found relatively stable.

Nitrate Measurement in Extracted Soil Solution. To demonstrate the nitrate measurement in extracted soil water, soil water was extracted from three locations at the Iowa State BioCentury Research Farm (Ames, Iowa) using a suction lysimeter. The suction head of the lysimeter was inserted to a depth of 25 cm from the soil surface. As the POT-$MoS_2$-based sensor was dipped into different test solutions, the sensor responded by providing different voltage signals (FIG. 27a). The inset of FIG. 27a shows the converted nitrate concentration using the calibration curve of the sensor (FIG. 26a). For comparison, a commercial sensor (LaQua Horiba nitrate sensor) was used to measure the same sample solutions. Our sensor and the commercial sensor showed comparable readings.

Short-Term Nitrate Measurement in Soil Column. To demonstrate the short-term nitrate measurement in a soil column, two identical POT-MoS$_2$ based sensors were fixed on the walls of two column beakers filled with soil slurries (FIG. 27c). The column beakers were 6 cm in diameter and 10 cm in height and loaded with soils to a height of 9 cm from the bottom of the beaker. Several 3 mm diameter holes were created at the bottom of the beaker to flush out the water. Each sensor was located 7 cm from the bottom, as shown in FIG. 27b. The soil used here was collected from the soil surface at the research farm mentioned above. During the demonstration, the soil in one beaker was flushed with alternating solutions of 0 and 50 ppm $NO_3^-$—N at different time points, each time lasting 2 min, whereas the soil in the other beaker was flushed with 0 and 100 ppm $NO_3^-$—N. FIG. 27d shows the voltage outputs of the two sensors installed in the two beakers. When the soil was flushed with DI water (0 ppm), the output voltage of the sensor reached a baseline voltage of approximately −110 mV. When the soil was treated with 50 or 100 ppm nitrate solution, the sensor 1 and sensor 2 outputs went down to approximately −123 mV or approximately −150 mV, respectively. FIG. 27e shows the nitrate concentrations converted from the voltage outputs of the sensors. It should be noted that the converted concentrations are evidently lower than the known input nitrate concentrations. The nitrate solution was flushed out of the soil slurries immediately after introducing the solution, and the prewetted soil particles already had water content that may have diluted the external original concentration of nitrate in the testing soil slurries, resulting in reduced ppm levels compared with the original input concentration of nitrate. Alternatively, when we introduced the external nitrate concentration into the soil, as nitrate has a low charge density compared to other common pre-existing anions in soil solution and they always occupy the few positively charges sites, in turn, the nitrate ions may have failed to bind with soil particles within a short period of time or denitrification of nitrate ions, thus, both sensors showed reduced ppm nitrate levels. However, the sensor response returned to the baseline ppm level immediately as we flushed with DI water.

For long-term measurements, two identical sensors (sensor 1 and sensor 2) were deployed directly into the soil slurries in column beakers over approximately 4 weeks with different rates of nitrate concentration (50 and 100 ppm $NO_3^-$—N), and OCP was measured continuously (FIG. 28a,b). For this measurement, the beaker dimensions were the same, and the sensors were fixed at the same location as for the short-term measurement. However, unlike the previous design of the beakers for the short-term measurement, there were no holes at the bottom of the beakers to promote denitrification of nitrate ions in the soil slurries before evaporation.

The long-term monitoring of nitrates in soil slurries using sensor 1 and sensor 2 is shown in FIG. 28c-e. For sensor 1, when the soil beaker was treated with DI water, the $NO_3^-$—N level was found to be approximately 14-23 ppm (FIG. 28c, marked with box), which is similar to that observed in the short-term measurement. Because of the slow diffusion of preoccurring nitrate ions from the soil slurry into water, the nitrate level slowly increased after water was poured, until it reached a maximum concentration. Further, the sensor showed a slow decrease in $NO_3^-$—N concentration to the range of 2-5 ppm because of the denitrification at room temperature (25° C.). In this parched soil condition, the nitrate ppm was found to be almost constant. Upon further repeating the experiment two times, the sensor showed similar results.

Interestingly, when the 50 ppm $NO_3^-$—N was poured into the soil beaker, sensor 1 began to show a slow increase in $NO_3^-$—N and reached a maximum value of 53 ppm $NO_3^-$—N. With the addition of external nitrate into the soil, the sensor took approximately 3 h to reach a maximum nitrate level, indicating a slow diffusion of nitrate ions into the soil. This is because when the soil particles at the sensor interface are completely wet, nitrate ions may diffuse slowly from the external nitrate solution (as we filled the beaker) because of the concentration gradient. The $NO_3^-$—N concentration was further decreased to a low value of 2-5 ppm when the soil particles became parched because of water evaporation, which restricted the mobility of the nitrate ions. Sensor 1 showed an almost similar performance of $NO_3^-$—N, whereas the sensor was further flushed with 50 ppm $NO_3^-$—N concentration another three times. When more water containing $NO_3^-$—N(see the last two repeated measurements, FIG. 28c) was poured, the sensor showed a longer nitrate response at 50 ppm, as the evaporation of water from the soil takes time.

Similarly, for sensor 2, the sensor performance was investigated in the presence of DI water and 100 ppm of $NO_3^-$—N concentration for 2 weeks (FIG. 28d), and the sensor was kept in parched soil conditions for another 2 weeks (FIG. 28e). With DI water filling, the sensor exhibited a concentration of approximately 20-25 ppm of $NO_3^-$—N because of the pre-existing nitrate ions in the soil. Further, the soil water content dried slowly, and the soil became parched under this condition. The sensor showed a similar $NO_3^-$—N response as was observed in the case of sensor 1. When the soil slurry was flushed with 100 ppm $NO_3^-$—N solution, the output of the sensor reached a maximum value of $NO_3^-$—N(approximately 104 ppm), after which the sensor response began to decay to less than 10 ppm of $NO_3^-$—N because of water evaporation. Further, sensor 2 was kept in the same soil without the addition of water for approximately 2 weeks, and the concentration variability was investigated (FIG. 28e). The soil became parched without the addition of water and $NO_3^-$—N solution. Under this condition, however, the sensor still exhibited a low ppm of nitrate (approximately 10-2 ppm). Interestingly, the sensor response decreased from approximately 10 to 3 ppm over a long period of time (13 days), but the sensor response was found to be irregular, perhaps because of the changing room temperature or humidity level. The sensor deployed into soil slurries can monitor nitrate-nitrogen accurately for at least a duration of 27 days.

Conclusions

In this manuscript, a novel all-solid-state miniature sensor designed for long-term use in continuous monitoring of soil nitrate was presented. The sensor was fabricated on a PCB using patterned WE and RE. To characterize the sensor materials, solid-state components using MoS$_2$, POT, and POT-MoS$_2$ were directly coated on the patterned PCB and functionalized with an ISM using a high-precision robotic-armed auto-dispenser machine. The electroactivity property of the POT-MoS$_2$ composite was found to be excellent, and the material was used as an ion-to-electron transducing layer for nitrate detection in the sensor. The POT-MoS$_2$ composite material produced superior sensor performance in terms of selectivity and sensitivity compared with MoS$_2$ and POT and the reported nitrate sensors shown in Table 1. This may be the result of the high hydrophobicity and high redox properties of the POT-MoS$_2$ layer. The solid-state sensor is selective to nitrate ions even when other anions are present at significant concentrations and offers long-term stability. This sensor can be deployed into the soil for long-term nitrate monitoring (about 4 weeks). In the future, by replacing the ion-selective membrane, the sensor could be adapted to detect other soil nutrients, including potassium, phosphate, and sulfate. These other nutrients are also essential to plant growth and agricultural productivity. Continuous measurements of these nutrients thus have significant potential applications in plant biology, plant breeding, environmental science, and production agriculture.

Associated Content

*S Supporting Information

The Supporting Information is available free of charge on the ACS Publications website at DOI: 10.1021/acsami.9b07120. Reproducibility, repeatability studies, and potential stability of the sensor (PDF), and incorporated by reference herein.

With respect to Specific Example 3, supporting information referenced above can be found at FIGS. 29A, 29B, and 29C and Table S1 below.

TABLE S1

Values of potential drifts per second ($\Delta E/\Delta t$) and capacitate for different electrode materials (POT, MoS$_2$ and POT-MoS$_2$)

| Nitrate Selective Electrode materials | $\Delta E/\Delta t$ ($\mu V/s$) | C ($\mu F$) |
| --- | --- | --- |
| POT | 115.4 | 433 |
| MoS$_2$ | 213.3 | 234 |
| POT-MoS$_2$ | 95.0 | 526 |

REFERENCES REGARDING EXAMPLE 3

(1) Lipper, L.; Thornton, P.; Campbell, B. M.; Baedeker, T.; Braimoh, A.; Bwalya, M.; Caron, P.; Cattaneo, A.; Garrity, D.; Henry, K.; Hottle, R.; Jackson, L.; Jarvis, A.; Kossam, F.; Mann, W.; McCarthy, N.; Meybeck, A.; Neufeldt, H.; Remington, T.; Sen, P. T.; Sessa, R.; Shula, R.; Tibu, A.; Torquebiau, E. F. Climate-Smart Agriculture for Food Security. Nat. Clim. Change 2014, 4, 1068.

(2) Walter, A.; Finger, R.; Huber, R.; Buchmann, N. Opinion: Smart Farming is Key to Developing Sustainable Agriculture. Proc. Natl. Acad. Sci. U.S.A. 2017, 114, 6148-6150.

(3) White, J. W.; Andrade-Sanchez, P.; Gore, M. A.; Bronson, K. F.; Coffelt, T. A.; Conley, M. M.; Feldmann, K. A.; French, A. N.; Heun, J. T.; Hunsaker, D. J.; Jenks, M. A.; Kimball, B. A.; Roth, R. L.; Strand, R. J.; Thorp, K. R.; Wall, G. W.; Wang, G. Field-based Phenomics for Plant Genetics Research. Field Crop. Res. 2012, 133, 101-112.

(4) Adamchuk, V. I.; Hummel, J. W.; Morgan, M. T.; Upadhyaya, S. K. On-The-Go Soil Sensors for Precision Agriculture. Comput. Electron. Agric. 2004, 44, 71-91.

(5) Ali, M. A.; Jiang, H.; Mahal, N. K.; Weber, R. J.; Kumar, R.; Castellano, M. J.; Dong, L. Microfluidic Impedimetric Sensor for Soil Nitrate Detection using Graphene Oxide and Conductive Nanofibers Enabled Sensing Interface. Sens. Actuators, B 2017, 239, 1289-1299.

(6) Ali, M. A.; Mondal, K.; Wang, Y.; Jiang, H.; Mahal, N. K.; Castellano, M. J.; Sharma, A.; Dong, L. In situ integration of graphene foam-titanium nitride based bio-scaffolds and microfluidic structures for soil nutrient sensors. Lab Chip 2017, 17, 274-285.

(7) Dalal, R. C.; Henry, R. J. Simultaneous Determination of Moisture, Organic Carbon, and Total Nitrogen by Near Infrared Reflectance Spectrophotometryl. Soil Sci. Soc. Am. J. 1986, 50, 120-123.

(8) Hood-Nowotny, R.; Umana, N. H.-N.; Inselbacher, E.; OswaldLachouani, P.; Wanek, W. Alternative methods for measuring inorganic, organic, and total dissolved nitrogen in soil. Soil Sci. Soc. Am. J. 2010, 74, 1018-1027.

(9) Daniel, A.; Birot, D.; Lehaitre, M.; Poncin, J. Characterization and reduction of interferences in flow-injection analysis for the in situ determination of nitrate and nitrite in sea water. Anal. Chim. Acta 1995, 308, 413-424.

(10) Schroeder, D. C. The analysis of nitrate in environmental samples by reversed-phase HPLC. J. Chromatogr. Sci. 1987, 25, 405-408.

(11) Yoshizumi, K.; Aoki, K.; Matsuoka, T.; Asakura, S. Determination of nitrate by a flow system with a chemiluminescent nitrogen oxide (NOx) analyzer. Anal. Chem. 1985, 57, 737-740.

(12) Englmaier, P. Nitrate analysis by gas-liquid chromatography using the nitration of 2,4-dimethylphenol in sulphuric acid. J. Chromatogr. A 1983, 270, 243-251.

(13) Zhang, C.; Kovacs, J. M. The Application of Small Unmanned Aerial Systems for Precision Agriculture: A Review. Precis. Agric. 2012, 13, 693-712.

(14) Mills, H. A.; Jones, J. B., Jr Nutrient Deficiencies and Toxicities in Plants: Nitrogen. J. Plant Nutr. Soil Sci. 1979, 1, 101-122.

(15) Ali, M. A.; Hong, W.; Oren, S.; Wang, Q.; Wang, Y.; Jiang, H.; Dong, L. Tunable Bioelectrodes with Wrinkled-Ridged Graphene Oxide Surfaces for Electrochemical Nitrate Sensors. RSC Adv. 2016, 6, 67184-67195.

(16) Schazmann, B.; Diamond, D. Improved nitrate sensing using ion selective electrodes based on urea-calixarene ionophores. New J. Chem. 2007, 31, 587-592.

(17) Jiang, H.; Ali, Md. A.; Jiao, Y.; Yang, B.; Dong, L. In-situ, Realtime Monitoring of Nutrient Uptake on Plant Chip Integrated with Nutrient Sensor. Proceedings of the 2017 19th International Conference on Solid-State Sensors, Actuators and Microsystems (TRANSDUCERS), Kaohsiung, Taiwan; IEEE, 2017; pp 289-292.

(18) Xu, Z.; Wang, X.; Weber, R. J.; Kumar, R.; Dong, L. Nutrient Sensing using Chip Scale Electrophoresis and In situ Soil Solution Extraction. IEEE Sens. J. 2017, 17, 4330-4339.

(19) Bobacka, J. Potential Stability of All-Solid-State Ion-Selective Electrodes using Conducting Polymers as Ion-to-Electron Transducers. Anal. Chem. 1999, 71, 4932.

(20) Cattrall, R. W.; Freiser, H. Coated Wire Ion-Selective Electrodes. Anal. Chem. 1971, 43, 1905-1906.

(21) Bobacka, J.; Ivaska, A.; Lewenstam, A. Potentiometric Ion Sensors. Chem. Rev. 2008, 108, 329-351.

(22) Silvester, D. S. Recent Advances in the Use of Ionic Liquids for Electrochemical Sensing. Analyst 2011, 136, 4871-4882.

(23) Hu, J.; Stein, A.; Balmann, P. Rational Design of All-SolidState Ion-Selective Electrodes and Reference Electrodes. TrAC, Trends Anal. Chem. 2016, 76, 102-114.

(24) Cadogan, A.; Gao, Z.; Lewenstam, A.; Ivaska, A.; Diamond, D. All-solid-state sodium-selective electrode based on a calixarene ionophore in a poly(vinyl chloride) membrane with a polypyrrole solid contact. Anal. Chem. 1992, 64, 2496-2501.

(25) McQuade, D. T.; Pullen, A. E.; Swager, T. M. Conjugated Polymer-based Chemical Sensors. Chem. Rev. 2000, 100, 2537-2574.

(26) Lindner, E.; Gyurcsanyi, R. E. Quality Control Criteria for Solid-Contact, Solvent Polymeric Membrane Ion-Selective Electrodes. J. Solid State Electrochem. 2009, 13, 51-68.

(27) Si, P.; Bakker, E. Thin Layer Electrochemical Extraction of Non-Redoxactive Cations with an Anion-Exchanging Conducting Polymer Overlaid with a Selective Membrane. Chem. Commun. 2009, 5260-5262.

(28) Vazquez, M.; Bobacka, J.; Ivaska, A. Potentiometric sensors for Ag+ based on poly(3-octylthiophene) (POT). J. Solid StateElectrochem. 2005, 9, 865-873.

(29) Gao, W.; Emaminejad, S.; Nyein, H. Y. Y.; Challa, S.; Chen, K.; Peck, A.; Fahad, H. M.; Ota, H.; Shiraki, H.; Kiriya, D.; Lien, D.-H.; Brooks, G. A.; Davis, R. W.; Javey, A. Fully Integrated Wearable Sensor Arrays for Multiplexed in situ Perspiration Analysis. Nature 2016, 529, 509-514.

(30) Bobacka, J. Potential Stability of All-Solid-State Ion-Selective Electrodes using Conducting Polymers as Ion-to-Electron Transducers. Anal. Chem. 1999, 71, 4932 4937.

(31) Fibbioli, M.; Morf, W. E.; Badertscher, M.; de Rooij, N. F.; Pretsch, E. Potential Drifts of Solid-Contacted Ion-Selective Electrodes Due to Zero-Current Ion Fluxes Through the Sensor Membrane. Electroanalysis 2000, 12, 1286-1292.

(32) Ping, J.; Wang, Y.; Wu, J.; Ying, Y. Development of an All-SolidState Potassium Ion-Selective Electrode using Graphene as the SolidContact Transducer. Electrochem. Commun. 2011, 13, 1529-1532.

(33) Anastasova-Ivanova, S.; Mattinen, U.; Radu, A.; Bobacka, J.; Lewenstam, A.; Migdalski, J.; Danielewski, M.; Diamond, D. Development of Miniature All-Solid-State Potentiometric Sensing System. Sens. Actuators, B 2010, 146, 199-205.

(34) Dam, V. A. T.; Zevenbergen, M. A. G.; Van Schaijk, R. Toward Wearable Patch for Sweat Analysis. Sens. Actuators, B 2016, 236, 834-838.

(35) Athavale, R.; Dinkel, C.; Wehrli, B.; Bakker, E.; Crespo, G. A.; Brand, A. Robust Solid-Contact Ion Selective Electrodes for High Resolution In Situ Measurements in Fresh Water Systems. Environ. Sci. Technol. Lett. 2017, 4, 286-291.

(36) Yuan, D.; Anthis, A. H. C.; Ghahraman Afshar, M.; Pankratova, N.; Cuartero, M.; Crespo, G. A.; Bakker, E. All-Solid-State Potentiometric Sensors with a Multi-walled Carbon Nanotube Inner Transducing Layer for Anion Detection in Environmental Samples. Anal. Chem. 2015, 87, 8640-8645.

(37) Zhu, J.; Li, X.; Qin, Y.; Zhang, Y. Single-piece solid-contact ionselective electrodes with polymer-carbon nanotube composites. Sen. Actuators, B 2010, 148, 166-172.

(38) Criscuolo, F.; Taurino, I.; Stradolini, F.; Carrara, S.; DeMicheli, G. Highly-Stable Li+ Ion-Selective Electrodes based on Noble Metal Nanostructured Layers as Solid-Contacts. Anal. Chim. Acta 2018, 1027, 22-32.

(39) Lai, C.-Z.; Fierke, M. A.; Stein, A.; Bühlmann, P. Ion-Selective Electrodes with Three-Dimensionally Ordered Macroporous Carbon as the Solid Contact. Anal. Chem. 2007, 79, 4621-4626.

(40) Bobacka, J. Conducting Polymer-Based Solid-State IonSelective Electrodes. Electroanalysis 2006, 18, 7-18.

(41) Guo, J.; Amemiya, S. Voltammetric Heparin-Selective Electrode based on Thin Liquid Membrane with Conducting Polymer-Modified Solid Support. Anal. Chem. 2006, 78, 6893-6902.

(42) Kim, Y.; Amemiya, S. Stripping Analysis of Nanomolar Perchlorate in Drinking Water with a Voltammetric Ion-Selective Electrode based on Thin-Layer Liquid Membrane. Anal. Chem. 2008, 80, 6056-6065.

(43) Veder, J.-P.; De Marco, R.; Clarke, G.; Chester, R.; Nelson, A.; Prince, K.; Pretsch, E.; Bakker, E. Elimination of Undesirable Water Layers in Solid-Contact Polymeric Ion-Selective Electrodes. Anal. Chem. 2008, 80, 6731-6740.

(44) da Silva, E. A.; Oliveira, V. J. R. d.; Braunger, M. L.; Constantino, C. J. L.; Olivati, C. d. A. Poly(3-octylthiophene)/stearic Acid Langmuir and Langmuir-Blodgett films: Preparation and characterization. Mater. Res. 2014, 17, 1442-1448.

(45) Jarvis, J. M.; Guzinski, M.; Pendley, B. D.; Lindner, E. Poly(3-Octylthiophene) as Solid Contact for Ion-Selective Electrodes: Contradictions and Possibilities. J. Solid State Electrochem. 2016, 20, 3033-3041.

(46) Yang, L.; Wang, S.; Mao, J.; Deng, J.; Gao, Q.; Tang, Y.; Schmidt, 0. G. Hiearchical $MoS_2$/Polyaniline Nanowires with Excellent Electrochemical Performance for Lithium-Ion Batteries. Adv. Mater. 2013, 25, 1180-1184.

(47) El Beqqali, O.; Zorkani, I.; Rogemond, F.; Chermette, H.; Chaabane, R. B.; Gamoudi, M.; Guillaud, G. Electrical Properties of Molybdenum Disulfide MoS2. Experimental Study and Density Functional Calculation Results. Synth. Met. 1997, 90, 165-172.

(48) Wu, S.; Zeng, Z.; He, Q.; Wang, Z.; Wang, S. J.; Du, Y.; Yin, Z.; Sun, X.; Chen, W.; Zhang, H. Electrochemically Reduced Single-Layer MoS2 Nanosheets: Characterization, Properties, and Sensing Applications. Small 2012, 8, 2264-2270.

(49) Barua, S.; Dutta, H. S.; Gogoi, S.; Devi, R.; Khan, R. Nanostructured MoS2-Based Advanced Biosensors: A Review. ACS Appl. Nano Mater. 2018, 1, 2-25.

(50) Yang, T.; Meng, L.; Chen, H.; Luo, S.; Li, W.; Jiao, K. Synthesis of Thin-Layered Molybdenum Disulfide-Based Polyaniline Nanointerfaces for Enhanced Direct Electrochemical DNA Detection. Adv. Mater. Interfaces 2016, 3, 1500700.

(51) Wang, J.; Wu, Z.; Yin, H.; Li, W.; Jiang, Y. Poly (3, 4-ethylenedioxythiophene)/MoS2 Nanocomposites with Enhanced Electrochemical Capacitance Performance. RSC Adv. 2014, 4, 56926-56932.

(52) Jang, A.; Zou, Z.; Lee, K. K.; Ahn, C. H.; Bishop, P. L. Potentiometric and voltammetric polymer lab chip sensors for determination of nitrate, pH and Cd(II) in water. Talanta 2010, 83, 1-8. (53) Nolan, M. A.; Tan, S. H.; Kounaves, S. P. Fabrication and Characterization of a Solid State Reference Electrode for Electroanalysis of Natural Waters with Ultramicroelectrodes. Anal. Chem. 1997, 69, 1244-1247.

(54) Bates, R. G.; Macaskill, J. B. Standard Potential of the SilverSilver Chloride Electrode. Pure Appl. Chem. 1978, 50, 1701-1706.

(55) Bakker, E.; Pretsch, E. Potentiometric Sensors for Trace-Level Analysis. Trends Anal. Chem. 2005, 24, 199-207.

(56) Bakker, E. Selectivity of Carrier-based Ion-Selective Electrodes: is the Problem Solved? Trends Anal. Chem. 1997, 16, 252-260.

(57) Baker, M. A.; Gilmore, R.; Lenardi, C.; Gissler, W. XPS Investigation of Preferential Sputtering of S from $MoS_2$

(58) Wang, F.; Mori, K.; Oishi, Y. Electrochemical Polymerization of 6-(N-Allyl-1,1,2,2-tetrahydroperfluorodecyl)amino-1,3,5-triazine-2,4-dithiol Monosodium on Aluminum. Polym. J. 2006, 38, 484.

(59) Buck, R. P.; Lindner, E. Recommendations for Nomenclature of Ionselective Electrodes (IUPAC Recommendations 1994). PureAppl. Chem. 1994, 66, 2527-2536.

(60) Cuartero, M.; Crespo, G. A.; Bakker, E. Tandem Electrochemical Desalination-Potentiometric Nitrate Sensing for Seawater Analysis. Anal. Chem. 2015, 87, 8084-8089.

(61) Bendikov, T. A.; Kim, J.; Harmon, T. C. Development and Environmental Application of a Nitrate Selective Microsensor based on Doped Polypyrrole Films. Sens. Actuators, B 2005, 106, 512-517.

(62) Garland, N. T.; McLamore, E. S.; Cavallaro, N. D.; MendivelsoPerez, D.; Smith, E. A.; Jing, D.; Claussen, J. C. Flexible Laser Induced Graphene for Nitrogen Sensing in Soil. ACS Appl. Mater. Interfaces 2018, 10, 39124-39133.

(63) Chaneam, S.; Taweetong, W.; Kaewyai, K.; Thienwong, P.; Takaew, A.; Chaisuksant, R. Fabrication of a Nitrate Selective Electrode for Determination of Nitrate in Fertilizers by using Flow Injection Analysis System. Procedia Chem. 2016, 20, 73-75.

(64) Khripoun, G. A.; Volkova, E. A.; Liseenkov, A. V.; Mikhelson, K. N. Nitrate-Selective Solid Contact Electrodes with Poly(3-octylthiophene) and Poly(aniline) as Ion-to-Electron Transducers Buffered with Electron-Ion-Exchanging Resin. Electroanalysis 2006, 18, 1322-1328.

(65) Rudd, S.; Dalton, M.; Buss, P.; Treijs, A.; Portmann, M.; Ktoris, N.; Evans, D. Selective Uptake and Sensing of Nitrate in Poly (3, 4-ethylenedioxythiophene). Sci. Rep. 2017, 29, 16581.

(66) Wardak, C. Solid Contact Nitrate Ion-Selective Electrode Based on Ionic Liquid with Stable and Reproducible Potential. Electroanalysis 2014, 26, 864-872.

(67) Pick, M.; Piech, R.; Paczosa-Bator, B. All-solid-state nitrate selective electrode with graphene/tetrathiafulvalene nanocomposite as high redox and double layer capacitance solid contact. Electrochim. Acta 2016, 210, 407-414.

(68) Paczosa-Bator, B. Effects of type of nanosized carbon black on the performance of an all-solid-state potentiometric electrode for nitrate. Microchim. Acta 2014, 181, 1093-1099.

(69) Pick, M.; Piech, R.; Paczosa-Bator, B. Improved nitrate sensing using solid contact ion selective electrodes based on TTF and its radical salt. J. Electrochem. Soc. 2015, 162, B257-B263.

(70) Umezawa, Y.; Bühlmann, P.; Umezawa, K.; Tohda, K.; Amemiya, S. Potentiometric Selectivity Coefficients of Ion-Selective Electrodes. Part I. Inorganic cations (technical report). Pure Appl. Chem. 2000, 72, 1851-2082.

(71) Nagele, M.; Bakker, E.; Pretsch, E. General Description of the Simultaneous Response of Potentiometric Ionophore-based Sensors to Ions of Different Charge. Anal. Chem. 1999, 71, 1041-1048.

F. Example 3

With particular reference to FIGS. 30-35, an Example 3 showing methods, apparatus and systems according to the invention is shown and described below.

The following is additional and supplementing description of aspects of the invention taken from Md. Azahar Ali, Xinran Wang, Yuncong Chen, Yueyi Jiao, Michael J. Castellano, James C. Schnable, Patrick S. Schnable, and Liang Dong. Transducers 2019-EUROSENSORS XXXIII, Berlin, Germany, 23-27 Jun. 2019, and incorporated by reference herein in its entirety.

Novel all-Solid-State Soil Nutrient Sensor Using Nanocomposite of Poly(3-Octyl-Thiophene) and Molybdenum Sulfate Abstract Nitrate is a major macronutrient for plant growth. There is a high demand to develop robust, reliable, and maintenance-free soil sensors for long-term monitoring of nitrate variations in field. An ion-selective membrane-based solid-state nitrate sensor is developed using poly(3-octyl-thiophene)-molybdenum disulfide nanocomposite as an ion-to-electron transducing layer. The sensor offers a high sensitivity of 64 mV/decade, a dynamic range of 1-1500 ppm $NO_3^-$—N, and an improved selectivity for nitrate detection in soils. The sensor has demonstrated the ability to continuously monitor soil nitrate concentrations over a period of four weeks.

Introduction

After water, soil nitrogen (N) is the most limiting factor for plant growth. Crop productivity relies heavily on N fertilization [1]. At present N fertilizer is not efficiently assimilated by crops. Excess N fertilizer leaks into the environment, leading to significant negative environmental impacts on water quality, biodiversity, and atmospheric pollution. Continuous monitoring of nitrate dynamics in crop fields provides us maximum control over fertilizer management. Laboratory measurement of soil nitrogen is time-consuming and labor intensive. Remote sensors and on-the-go vehicle-based sensors have been used for in-field measurement of soil nitrate [1][2]. Accurate, long-term and field deployable nitrate sensors are still challenging.

Ion-selective membrane (ISM)-based potentiometric sensors are widely used to detect nitrate in water [3]. But, due to the necessity of using inner-filling solutions, conventional ISM-based nitrate sensors lack portability and long-term deployability [4]. Efforts have been made to develop all-state-solid sensors by introducing solid-contact ion-to-electron transducing materials, such as carbon nanotube [5], polypyrrole [6] and graphene [7], between the ISM and an electron conducting layer of the sensor. A desired solid-contact ion-to-electron transducing material requires both high redox property and hydrophobicity to increase stability, selectivity, and sensitivity.

This paper reports an all-solid-state potentiometric sensor for continuous monitoring of soil nitrate levels. The sensor uses a novel nanocomposite of poly(3-octyl-thiophene) (POT) and two-dimensional transition metal dichalcogenides of molybdenum disulfide ($MoS_2$) sheets as a solid-contact ion-to-electron transducing layer. POT has an excellent redox property but its electrical conductivity is low. $MoS_2$ sheets can provide a larger surface area, high conductivity, insensitivity to light or pH, and absence of possible side-reactions. The working electrode (WE) of the sensor is built on top of a copper pad of printed circuit board (PCB) covered by a patterned thin Au layer, a POT-$MoS_2$ nanocomposite-based solid-contact layer, and a nitrate-specific ISM. The incorporation of $MoS_2$ into POT can not only increase redox properties of POT, but also provide high hydrophobicity to minimize the formation of water thin layer between the ISM and metallic electron conduction layer. Generally, a notorious thin waterlayer is often formed at the interface between the ISM and conducting metal layer, acting as an interfacial barrier to fast electron transfer and negatively impacting selectivity of the sensor because different ions may be trapped inside this water layer. In our case, due to high hydrophobicity, the POT-MoS$_2$ can counter the issue with the trapped water layer, contributing to increasing charge transfer and ion selectivity of the sensor. The reference electrode (RE) of the sensor includes a silver/silver chloride (Ag/AgCl) electrode covered by a proton exchange membrane to reduce redox reaction-induced chloride leaching from the RE, contributing to minimizing drift of reference potential.

The presented sensor is featured with an all-solid-state design that incorporates the POT-MoS$_2$ nanocomposite for improved device performance. It should be noted that the sensor is embedded in soil for continuous monitoring of nitrate dynamics for about four weeks.

Device Fabrication

This sensor was made on a PCB with two electrodes wherein one served as a WE 30 and the other as a RE 40. To functionalize the WE 30, POT and MoS$_2$ with a weight ratio of 1:4 (concentration of POT: 2.6 mg/mL) were dispersed in tetrahydrofuran. This composite solution was coated on a 4 mm-diameter circular Au using a high-precision liquid dispensing machine (FIG. 30a), and then dried at room temperature. After that, a nitrate-specific ISM was coated on the POT-MoS$_2$ layer and then conditioned in a 1500 ppm NO$_3^-$—N solution for 24 hr.

For the RE 40, Ag/AgCl paste was screen-printed on a silver layer and then dried at 110° C. for 2 hr. A perfluorinated polymer, Nafion, was then coated on the surface of Ag/AgCl. The Nafion layer was dried at 90° C. for 1 hr. The role of Nafion is to prevent redox reaction-induced chloride leaching from the Ag/AgCl material to increase potential stability at the RE.

FIG. 31 shows the scanning electron microscopic (SEM) images for MoS$_2$ sheets (a), POT (b), and POT-MoS$_2$ (c) with schematics of different structural layers. Image (a) shows MoS$_2$ sheets with a combination of large (>1 µm) and small (<1 µm) sheets. The observed porous morphology of POT is useful for forming a composite with MoS$_2$ (image b). In the POT-MoS$_2$ composite, MoS$_2$ is covered by POT maybe due to the oppositely charged interactions. A morphological transition of POT and MoS$_2$ indicate the formation of POT-MoS$_2$ composite (image c). The POT-MoS$_2$ is ~1 µm thick (image d). FIG. 31e shows a schematic presentation and molecular structure of both POT and MoS$_2$.

FIG. 31f shows the ion exchange mechanism of the sensor for nitrate detection. The redox reaction is given by:

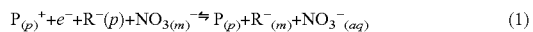

$$P_{(p)}^+ + e^- + R^-_{(p)} + NO_{3(m)}^- \rightleftharpoons P_{(p)} + R^-_{(m)} + NO_3^-_{(aq)} \quad (1)$$

where m, p, and aq represent the ISM phase, POT-MoS$_2$ nanocomposite phase, and aqueous phase, respectively, and P$_{(p)}$ and P$^+_{(p)}$ represent a few monomeric units of the POT-MoS$_2$ in the neutral insulating state, and the oxidized state with polaronic sites, respectively. The movement of anions or cations, with the help of specific binding sites, produces a potential difference. E depends on the logarithm of the ion activity and described by Nernst equation, $$E = E_0 + E_1 = E_0 + (RT/zF) \ln a_f(I) \quad (2)$$

where $a_f(I)$, R, T, z and F are the primary ion activity without any interfering, ions gas constant, temperature, charge in target ion, and Faraday constant, respectively. $E_0$ and $E_1$ are the constant potential at the RE and the potential devolved at the WE, respectively.

Experimental Results

Electrochemical Studies

The cyclic voltammetry (CV) studies (FIG. 32a) show that the POT-MoS$_2$-based sensor exhibited a higher redox current and peak-to-peak potential, compared to the POT-based electrode. The conductive nature of MoS$_2$ results in an increase in electron transfer. When incorporating the ISM, the redox current of the POT-MoS$_2$ decreased due to the insulating nature of ISM. The negatively charged ISM may repel ferro/ferricyanide molecules, thus reducing electron transfer.

The weight ratio of POT and MoS$_2$ was optimized (FIG. 32b) using the CV method wherein the peak-to-peak potential ($\Delta E$) was calculated for the POT-MoS$_2$ electrode by varying MoS$_2$ concentration in the composite. At 1:4 weight ratio of POT and MoS$_2$, the $\Delta E$ was found to reach maximum. Measurement results for open circuit potential (OCP) of three electrodes (coated with MoS$_2$, POT or POT-MOS$_2$ and a nitrate-specific ISM) are shown in the inset of FIG. 32b. The OCP for the POT-MOS$_2$-based electrode (−327 mV) was shown higher than that for the POT- (−263 mV) and the MOS$_2$-based (−63 mV) electrodes. As evident in the CV studies, the POT-MoS$_2$ electrode shows a high redox capacitance property and redox electroactivity, allowing selective uptaking or release of hydrophilic NO$_3^-$ ions.

Nitrate Detection in Standard Solution

Nitrate detection was investigated for all the sensors using MoS$_2$, POT and POT-MoS$_2$ as different solid-contact materials. A home-made circuit was used to read out the OCP values as a function of concentration from 1 to 1500 ppm NO$_3^-$—N. As the concentration changed, OCP would change. FIG. 33a shows the output voltages for different WEs when responding to different nitrate concentrations. The corresponding calibration curves for the sensors are shown in FIG. 33b. The sensor using the POT-MoS$_2$ shows a higher sensitivity (64 mV/dec) with a wide dynamic range of 1 to 1500 ppm NO$_3^-$—N, compared to that using POT (48 mV/dec) or MoS$_2$ alone (38 mV/dec).

FIG. 33c shows the effect of environmental chloride ions on the ability of the POT-MoS$_2$-based sensor to detect nitrate ions. The result shows that the sensor was little affected by low-concentration ions (e.g., 0.01 M and 0.1 M) in the nitrate solution. However, with extreme high Cl— concentrations such as 0.5 M and 1 M, the sensor output was deviated by ±2.2% and ±4.0%, respectively, from the output without any interfering ions. The potential drift may be caused by the non-selective interaction of the sensor with ions in the ISM. Additional selectivity studies (FIG. 33d) of the different sensors were performed in presence of interfering anions such as phosphate (PO$_4^{3-}$), bicarbonate (HCO$_3^-$), and sulphate (SO$_4^{2-}$). The result shows that the POT-based or MoS$_2$-based sensor shows low selectivity, compared to the POT-MoS$_2$-based sensor.

Nitrate Detection in Soil

The POT-MoS$_2$-based nitrate sensor was applied to measure nitrate concentrations in extracted soil solutions collected from a corn field in Ames, Iowa. The readings from this sensor were compared with those from a commercial nitrate sensor (Lague Horiba). Our sensor measurement results agreed well with those obtained using the commercial sensor (FIG. 34a).

Two POT-MoS$_2$-based sensors were fixed on the walls of two column beakers filled with soil slurries (FIG. 34b-c). The beaker was 6 cm in diameter and 10 cm in height, and was loaded with mineral soils till 9 cm height from the bottom of the beaker. Small drain holes were created at the bottom. Each sensor was located at 7 cm from the bottom.

During the measurement, the soil in one beaker was flushed with alternating solutions of 0 and 50 ppm $NO_3^-$—N at different times, each time lasting 2 minutes, while the soil in the other beaker was flushed with 0 and 100 ppm $NO_3^-$—N. FIG. 34d shows the outputs of the two sensors. When the soil was flushed with water (0 ppm), the output voltage of the sensor reached the −110 mV voltage baseline. When the soil was treated with the 50 ppm and 100 ppm $NO_3^-$—N solutions, one sensor output went down to −123 mV, while the other to −150 mV, respectively. FIG. 34e shows the nitrate levels converted from the output voltages of the sensors.

For long-term measurement, two sensors (sensor 1 and sensor 2) were deployed directly in soil slurries for ~27 days with different rates of nitrate concentration (50 and 100 ppm $NO_3$-N) (FIG. 35a-b). For the sensor 1, when the beaker (without holes at the bottom) was treated with water, $NO_3^-$—N was found to be ~14-23 ppm (FIG. 35c). Due to the slow diffusion of pre-occurrence nitrate ions from the soil slurry into water, the nitrate concentration slowly increased until a maximum concentration was reached. Further, the sensor showed a gradual decrease in concentration in a range of 2-5 ppm $NO_3^-$—N due to slow evaporation. In this parched soil condition, the nitrate concentration was found to be almost constant. Upon further repeating the experiment two times, the sensor showed similar results.

Interestingly, when the 50 ppm of $NO_3^-$—N was poured into the soil beaker, sensor 1 began to show a slow increase in $NO_3^-$—N, and reached a maximum value of 53 ppm $NO_3^-$—N. With the addition of external nitrate into the soil, the sensor took approximately 3 h to reach a maximum nitrate level, indicating slow diffusion of nitrate ions into the soil. This is because when soil particles at the sensor interface are completely wet, nitrate ions may diffuse slowly from the external nitrate solution (as we filled the beaker) due to the concentration gradient. The $NO_3^-$—N concentration was further decreased to a low value of 2-5 ppm when the soil particles became parched due to water evaporation, which restricted the mobility of the nitrate ions. Sensor 1 showed an almost similar performance of $NO_3^-$—N, while the sensor was further flushed with 50 ppm $NO_3^-$—N concentration another three times. When more water containing $NO_3^-$—N(see the last two repeated measurements, FIG. 35c) was poured, the sensor showed a longer nitrate response at 50 ppm, as the evaporation of water from the soil takes time.

Similarly, for sensor 2, the performance was studied in the presence of 0 ppm (water) and 100 ppm of $NO_3^-$—N concentration for 2 weeks (FIG. 35d), and the sensor was kept in parched soil conditions for another 2 weeks (FIG. 35e). With water filling, the sensor exhibited a concentration of approximately 20-25 ppm of $NO_3^-$—N due to the pre-existing nitrate ions in the soil. Further, the soil water content dried slowly, and the soil became parched under this condition. The sensor showed a similar $NO_3^-$—N response as was observed in the case of sensor 1. When the soil slurry was flushed with 100 ppm $NO_3^-$—N solution, the output of the sensor reached a maximum value of $NO_3^-$—N(approximately 104 ppm), after which the sensor response began to decay to less than 10 ppm of $NO_3^-$—N due to water evaporation. Further, sensor 2 was kept in the same soil without the addition of water for approximately 2 weeks, and the concentration variability was investigated (FIG. 35e). The soil become parched without the addition of water and $NO_3^-$—N solution. Under this condition, however, the sensor still exhibited a low ppm of nitrate (approximately 10-2 ppm). Interestingly, the sensor response decreased from approximately 10 ppm to 3 ppm over a long period of time (13 days), but the sensor response was found to be irregular, perhaps because of the changing room temperature or humidity level.

Conclusions

An all-solid-state miniature sensor designed for long-term use in continuous monitoring of soil nitrate was presented. The electro-activity properties of POT-MoS$_2$ composite were found to be excellent, and the material was used as an ion-to-electron transducing layer for nitrate detection in the sensor. The POT-MoS$_2$ composite material produced excellent sensor performance in terms of selectivity and sensitivity compared with MoS$_2$ and POT, and the reported nitrate sensors. This may be the result of the high lipophilicity and high redox properties of the POT-MoS$_2$ layer. The sensor is highly selectable with other anions and offers long-term stability. This sensor can be deployed into the soil for long-term nitrate monitoring. In the future, by replacing the ion selective membrane, the sensor can work to detect other soil nutrients, including potassium, phosphate, and sulfate, which will also help the phenotypic activity and nutrient uptake of plants [8]. With this evidence of sensor performance, the nitrate sensor may detect the variation in nitrate concentration in an agricultural setting [9]. This solid-state sensor may help farmers manage nitrogen fertilizer levels in fields to enhance crop yield.

REFERENCES RELATING TO EXAMPLE 3

[1] M. A. Ali, et al. "In situ integration of graphene foam-titanium nitride based bio-scaffolds and microfluidic structures for soil nutrient sensors." *Lab On A Chip*, 17.2 (2018): 274-285.

[2] V. I. Adamchuk, et al. "On-the-go soil sensors for precision agriculture." Computers and *Electronics in Agriculture*, 44.1 (2004): 71-91.

[3] P. SjoEberg, et al. "All-solid-state chloride-selective electrode based on poly (3-octylthiophene) and tridodecylmethylammonium chloride." *Electroanalysis*, 11.10-11 (1999): 821-824.

[4] J. Hu, et al. "Rational design of all-solid-state ion-selective electrodes and reference electrodes." *Trends in Analytical Chemistry* 76 (2016) 102-114.

[5] M. Cuartero, et al. "Tandem electrochemical desalination-potentiometric nitrate sensing for seawater analysis." *Analytical Chemistry*, 87.16 (2015) 8084-8089.

[6] T. A. Bendikov, et al. "Development and environmental application of a nitrate selective microsensor based on doped polypyrrole films." *Sensors and Actuators B. Chemical*, 106.2 (2005) 512-517.

[7] N. T. Garland, et al. "Flexible laser-induced graphene for nitrogen sensing in soil." *ACS Applied Materials Interfaces*, 10.45 (2018) 39124-39133.

[8] M. A. Ali, et al. "Microfluidic impedimetric sensor for soil nitrate detection using graphene oxide and conductive nanofibers enabled sensing interface." *Sensors and Actuators B. Chemical*, 239 (2017): 1289-1299.

[9] M. A. Ali, et al. "Tunable bioelectrodes with wrinkled-ridged graphene oxide surfaces for electrochemical nitrate sensors." *RSC Advances* 6.71 (2016): 67184-67195.

What is claimed is:

1. A system for self-contained, long term monitoring of soil and water nutrients in fields comprising:
   (a) a soil sampling head, the sampling head comprising:
      (i) a tube having at least a portion of its sidewall between opposite open ends which is gas/fluid permeable;

(ii) fluid connectors sealed at the opposite open ends of the tube;
(iii) the tube and connectors adapted to be placed in situ into soil or water at a measuring depth;
(b) a ruggedized housing including:
  (i) a biochemical detection subsystem comprising:
    (1) a sealed detection cell;
    (2) at least one electrochemical sensor in the detection cell;
  (ii) a fluid manipulation subsystem comprising:
    (1) a soil water extraction and delivery fluid circuit comprising:
      a. a vacuum pump in fluid communication with the detection cell;
      b. a fluid conduit from a connector at one end of the tube in the soil water sampling head to the detection cell in the housing;
      c. wherein selective operation of the vacuum pump during a sampling and detection cycle promotes collection of soil water/air in the soil sampling head and flow to the detection cell for biochemical sensing through the said connector at one end of the tube;
    (2) a system reset/reconditioning/recalibrating fluid circuit comprising:
      (a) a cleaning liquid reservoir and actuator to move cleaning fluid to the detection cell;
      (b) a waste liquid reservoir and actuator to move fluid in the tube to the waste liquid reservoir;
      (c) a recalibration liquid reservoir and actuators to move fluid to the detection cell and the waste liquid reservoir;
      (d) wherein selective operation of the actuators during a cleaning/reset/reconditioning cycle moves cleaning fluid through the system and removes all fluid to the waste reservoir to reset for the next sampling and detection cycle;
  (iii) a power source in operative connection to the electrodes, pump, and actuators; and
  (iv) a programmable microprocessor in operative connection to the electrodes, pump and actuators and including data storage for data from the detector.

2. The system of claim 1 wherein the electrochemical detector comprises:
(a) an ion selective electrode based chemical sensor;
(b) an ion selective field-effect transistor based chemical sensor;
(c) an enzymatic electrochemical chemical sensor;
(d) an optical chemical sensor with a chemically selective layer;
(e) a microwave based chemical sensor with a chemically selective layer; or
(f) extended gate field-effect transistor based chemical sensor.

3. The system of claim 1 wherein the electrochemical sensor comprises:
(a) a detection cell including a fluid-level sensor;
(b) an ion selective electrochemical sensor in the detection cell comprising:
  (i) a reference electrode comprising a sandwiched structure comprising:
    (1) a conducting layer;
    (2) a protection layer; and
    (3) a chemical storage layer between the conducting and protection layers; and
  (ii) a working electrode comprising a sandwiched structure comprising;
    (1) a conducting layer;
    (2) an ion-selective membrane; and
    (3) an ion-to-electron transducing layer between the ion-selective membrane and the conducting layer.

4. The system of claim 3 wherein:
(a) the ion-to-electron transducing layer of the working electrode comprises a polymeric composite of poly(3-octyl-thiophene) and molybdenum sulfate (POT-$MoS_2$) dissolved in THF solution printed or coated on a patterned said conducting layer;
(b) the chemical storage layer of the reference electrode comprises PVB/KCl;
(c) the protective layer of the reference layer comprises Nafion or polyurethane; and
(d) the conducting layer comprises an Ag/AgCl layer over a metallic conducting layer.

5. The system of claim 1 wherein the fluid manipulation subsystem is implemented with microfluidic components and actuators comprise peristaltic movement pumps.

6. The system of claim 1 wherein the electrochemical sensor comprises a soil nitrate detector.

7. A method of monitoring of soil or water nutrients in fields comprising:
(a) collecting soil water/air in situ into a porous tube placed at a selected depth in a field;
(b) pulling the collected soil water/air to an ion-selective detector comprising an ion-selective membrane at a working electrode comprising a sandwiched conducting layer, an ion-selective membrane, and an ion-to-electron transducing layer of a polymeric composite integrated with $MoS_2$ between the ion-selective membrane and the conducting layer;
(c) passing the collected soil water/air by the ion-to-electron transfer layer of the polymeric composite integrated with $MoS_2$ between the ion-selective membrane and the conducting layer of the working electrode to increase interfacial conductivity and minimize or prevent formation of an aqueous layer;
(d) passing the collected soil water/air by a reference electrode comprising a sandwiched conducting bottom layer, a middle layer with saturated chloride, and a protective top layer, to reduce chloride leaching-induced signal drift at the reference electrode;
(e) supplying electrical power to the electrochemical detector subsystem for ion-selective electrochemical detection related to the ion-selective membrane; and
(f) storing data regarding the detection.

8. The method of claim 7 wherein the porous tube is permeable to air and soil water through its sidewall, but allows fluid flow between open opposite ends; and comprises:
(a) a length in the approximate range of 1 cm to 20 cm;
(b) an outer diameter in the approximate range of 0.2 cm to 5 cm;
(c) an inner diameter in the approximate range of 0.1 cm to 0.2 cm;
(d) a porosity comprising an average pore size in the approximate range of 10 nanometers to 1 micrometer.

9. The method of claim 7 wherein the ion-selective membrane has selectivity for at least one of a set of soil nutrients comprising nitrate, phosphate, sulfate, and potassium.

10. The method of claim 7 wherein:
(a) the bottom conducting layer of the reference electrode comprises Ag/AgCl;
(b) the middle layer of the reference electrode comprises a polymeric membrane of polyvinyl butyral (PVB) with saturated chloride;
(c) the protective top layer of the reference electrode comprises a fluorinated top protective layer comprising Nafion or polyurethane.

11. The method of claim 7 further comprising purging and cleaning the sampled soil water/air at the detector and in the porous tube to recondition and reset for a next sampling and detection wherein the purging and cleaning are effectuated by peristaltic moving of fluid from a cleaning fluid supply to the detector and through the porous tube to a waste location.

12. The method of claim 7 wherein the polymeric composite comprises:
(a) poly(3-octyl-thiophene) and molybdenum sulfate (POT-MoS$_2$) dissolved in THF solution which is printed or coated on a patterned gold circular-shaped electrode to provide amphiphilic and redox properties resulting in reduction of sensor drift; and
(b) MoS$_2$ and one of poly(3,4-ethylenedioxythiophene)-polystyrene sulfonate, polyaniline, and polypyrrole.

13. The method of claim 7 wherein the ion-selective membrane comprises:
propanol (1.93 wt. %), 2-nitrophenyl octyl ether (16.25 wt. %), polyvinyl chloride (5.75 wt. %), tetrahydrofuran (74.3 wt. %), tridodecylmethylammonium nitrate (1.50 wt. %), and methyltriphenylphosphonium bromide (0.25 wt. %).

14. The method of claim 7 applied to:
ion-selective sensing of one or more water or soil nutrients.

15. An improved ion-selective electrode-based chemical detector comprising:
(a) a reference electrode comprising an Ag/AgCl bottom layer, a middle polymeric membrane of polyvinyl butyral (PVB) with saturated chloride, and a protonated Nafion top layer;
(b) a working electrode;
(c) an ion-selective membrane at the working electrode; and
(d) an ion-to-electron transducing interface between the ion-selective membrane and the working electrode, wherein the ion-to-electron transducing interface comprises a poly(3-octyl-thiophene)-molybdenum sulfate (POT-MoS$_2$) nanocomposite.

16. The detector of claim 15 wherein the POT-MoS$_2$ nanocomposite is:
printed or coated on the working electrode.

17. A method of fabricating a sensor for nutrient sensing in soil and water comprising:
(a) providing a reference electrode on a substrate, the reference electrode comprising:
(i) an Ag/AgCl electrode on the substrate;
(ii) a polymeric membrane of polyvinyl butyral (PVB) with saturated chloride on top of the Ag/AgCl electrode;
(iii) a protonated Nafion on top of the PVB layer; and
(b) providing a working electrode on a substrate, the working electrode comprising:
(i) an ion-to-electron transducing layer comprising a polymeric composite of poly(3-octyl-thiophene) and molybdenum sulfate (POT-MoS$_2$) and formed on a patterned metallic conducting electrode;
(ii) a covering layer of an ion-selective membrane; and (iii) a side-wall coating with waterproof epoxy to block water penetration.

18. The method of claim 17 wherein the composite of POT-MoS$_2$ is produced by:
(a) dissolving POT black powder in THF to provide a POT solution;
(b) adding ultrafine powder MoS$_2$ sheets to the POT solution and sonicating, wherein the weight ratio of POT to MoS2 is 1:4.

19. The method of claim 17 wherein the ion-selective membrane comprises:
nitrocellulose 2 nitrophenyl octyl ether, polyvinyl chloride, tetrahydrofuran, tridodecylmethylammonium nitrate, and methyltriphenylphosphonium bromide.

20. The method of claim 17 wherein providing the reference electrode comprises:
(a) treating a patterned silver electrode with a mixture of 0.1 M FeCl3 and 0.001 mM HCl solutions for 30 s to form Ag/AgCl;
(b) coating the Ag/AgCl with a polymer solution of 395 mg of PVB and 250 mg of KCl dissolved in 5 mL in tetrahydrofuran or methanol solvent;
(c) coating a 15 nm thick perfluorinated polymer or polyurethane on the PVB layer.

21. A system for self-contained, long term monitoring of chemicals in fields comprising:
(a) a soil sampling head, the sampling head comprising:
(i) a tube having at least a portion of its sidewall between opposite open ends which is gas/fluid permeable;
(ii) fluid connectors sealed at the opposite open ends of the tube;
(iii) the tube and connectors adapted to be placed in situ into soil or water at a measuring depth;
(b) a ruggedized housing including:
(i) a biochemical detection subsystem comprising:
(1) a sealed detection cell;
(2) at least one electrochemical sensor in the detection cell;
(ii) a fluid manipulation subsystem comprising:
(1) a soil water extraction and delivery fluid circuit comprising:
a. a vacuum pump in fluid communication with the detection cell;
b. a fluid conduit from a connector at one end of the tube in the soil water sampling head to the detection cell in the housing;
c. wherein selective operation of the vacuum pump during a sampling and detection cycle promotes collection of soil water/air in the soil sampling head and flow to the detection cell for chemical sensing through the said connector at one end of the tube;
(2) a system reset/reconditioning/recalibrating fluid circuit comprising:
(a) a cleaning liquid reservoir and actuator to move cleaning fluid to the detection cell;
(b) a waste liquid reservoir and actuator to move fluid in the tube to the waste liquid reservoir;
(c) a recalibration liquid reservoir and actuators to move fluid to the detection cell and the waste liquid reservoir;
(d) wherein selective operation of the actuators during a cleaning/reset/reconditioning cycle moves cleaning fluid through the system and removes all fluid to the waste reservoir to reset for the next sampling and detection cycle;

(iii) a power source in operative connection to the electrodes, pump, and actuators; and (iv) a programmable microprocessor in operative connection to the electrodes, pump and actuators and including data storage for data from the detector.

22. The apparatus of claim 21 wherein the chemicals comprise one or more of:

(a) one or more soil or water nutrients;

(b) one or more pesticides; and (c) one or more water pollutants.

* * * * *